(12) United States Patent
Hauel et al.

(10) Patent No.: US 7,109,192 B2
(45) Date of Patent: Sep. 19, 2006

(54) SUBSTITUTED IMIDAZO-PYRIDINONES AND IMIDAZO-PYRIDAZINONES, THE PREPARATION THEREOF AND THEIR USE AS PHARMACEUTICAL COMPOSITIONS

(75) Inventors: Norbert Hauel, Schemmerhofen (DE); Frank Himmelsbach, Mittelbiberach (DE); Elke Langkopf, Warthausen (DE); Matthias Eckhardt, Biberach (DE); Roland Maier, Biberach (DE); Michael Mark, Biberach (DE); Mohammad Tadayyon, Ulm (DE); Iris Kauffmann-Hefner, Attenweiler (DE)

(73) Assignee: Boehringer Ingelheim Pharma GmbH & Co KG, Ingelheim (DE)

( * ) Notice: Subject to any disclaimer, the term of this patent is extended or adjusted under 35 U.S.C. 154(b) by 294 days.

(21) Appl. No.: 10/726,214

(22) Filed: Dec. 2, 2003

(65) Prior Publication Data

US 2005/0020574 A1    Jan. 27, 2005

Related U.S. Application Data

(60) Provisional application No. 60/456,598, filed on Mar. 21, 2003, provisional application No. 60/437,438, filed on Dec. 30, 2002.

(30) Foreign Application Priority Data

Dec. 3, 2002 (DE) .............................. 102 56 264
Mar. 7, 2003 (DE) .............................. 103 09 927

(51) Int. Cl.
C07D 487/04 (2006.01)
C07D 471/04 (2006.01)
A61K 31/5025 (2006.01)
A61K 31/437 (2006.01)

(52) U.S. Cl. ................ 514/218; 544/236; 540/575; 514/248; 514/303; 546/118

(58) Field of Classification Search ............. 540/575; 544/236; 514/218, 248
See application file for complete search history.

(56) References Cited

U.S. PATENT DOCUMENTS

| 2002/0198205 A1 | 12/2002 | Himmelsbach et al. |
| 2004/0087587 A1 | 5/2004 | Himmelsbach et al. |
| 2004/0116328 A1 * | 6/2004 | Yoshikawa et al. ............ 514/2 |

FOREIGN PATENT DOCUMENTS

| CA | 2418656 A1 | 2/2002 |
| WO | WO 02/02560 | 1/2002 |
| WO | WO 02/14271 A | 2/2002 |
| WO | WO 02/068420 | 9/2002 |
| WO | WO 03/104229 A1 | 12/2003 |

OTHER PUBLICATIONS

English Abstract of Belijean-Leymarie et al. Canadian Journal of Chemistry (1983), 61(11), 2563-6 (one page).*

* cited by examiner

*Primary Examiner*—Kahsay Habte
(74) *Attorney, Agent, or Firm*—Thomas C. Blankinship; Michael P. Morris; Timothy X. Witkowski

(57) ABSTRACT

The present invention relates to substituted imidazo-pyridinones and imidazo-pyridazinones of general formula

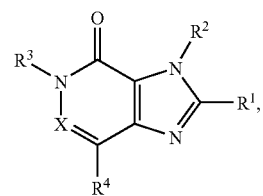

(I)

wherein $R^1$ to $R^4$ are defined as in claim 1, the tautomers, the stereoisomers, the mixtures thereof and the salts thereof, which have valuable pharmacological properties, particularly an inhibitory effect on the activity of the enzyme dipeptidylpeptidase-IV (DPP-IV).

9 Claims, No Drawings

SUBSTITUTED IMIDAZO-PYRIDINONES AND IMIDAZO-PYRIDAZINONES, THE PREPARATION THEREOF AND THEIR USE AS PHARMACEUTICAL COMPOSITIONS

APPLICATION DATA

This application claims benefit of U.S. Provisional Application No. 60/437,438 filed Dec. 30, 2002 which claims priority to German Application Number DE 10256264.4 and to U.S. Provisional Application No. 60/456,598 filed Mar. 21, 2003 which claims priority to German Application Number DE 10309927.1 each of which is incorporated by reference in its entirety.

DESCRIPTION OF THE INVENTION

The present invention relates to new substituted imidazo-pyridinones and imidazo-pyridazinones of general formula

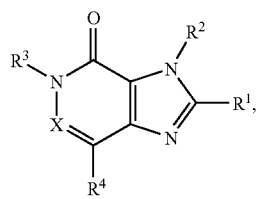

(I)

the tautomers, the enantiomers, the diastereomers, the mixtures thereof and the salts thereof, particularly the physiologically acceptable salts thereof with inorganic or organic acids or bases which have valuable pharmacological properties, particularly an inhibiting effect on the activity of the enzyme dipeptidylpeptidase-IV (DPP-IV), the preparation thereof, the use thereof for the prevention or treatment of diseases or conditions associated with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof as well as processes for the preparation thereof.

The present invention thus relates to the above compounds of general formula I which have valuable pharmacological properties, the tautomers, the enantiomers, the diastereomers, the mixtures thereof and the salts thereof, the pharmaceutical compositions containing the pharmacologically effective compounds, the use thereof and processes for the preparation thereof.

In the above general formula I

X denotes a nitrogen atom or a group of formula C—$R^5$,
  while $R^5$ denotes a hydrogen atom or a methyl group, $R^1$ denotes a 5- to 7-membered cycloalkyleneimino group which is substituted by an amino group in the carbon skeleton and may be substituted by a $C_{1-3}$-alkyl group,
a 6- to 7-membered cycloalkyleneimino group wherein the methylene group is replaced by a —NH— group in the 4 position,
or an amino group substituted by a $C_{5-7}$-cycloalkyl group,
  while the $C_{5-7}$-cycloalkyl group is substituted by an amino group or a carbon atom in the 3 position of the $C_{5-7}$-cycloalkyl group is replaced by an —NH— group, $R^2$ denotes a benzyl group wherein the phenyl group may be substituted by one or two fluorine, chlorine or bromine atoms or by a cyano group,
a straight-chain or branched $C_{3-8}$-alkenyl group,
a $C_{3-5}$-alkynyl group,
a $C_{3-7}$-cycloalkylmethyl group,
a $C_{5-7}$-cycloalkenylmethyl group,
or a furylmethyl, thienylmethyl, pyrrolylmethyl, thiazolylmethyl, imidazolylmethyl, pyridinylmethyl, pyrimidinylmethyl, pyridazinylmethyl or pyrazinylmethyl group, $R^3$ denotes a straight-chain or branched $C_{1-6}$-alkyl group,
a phenyl-$C_{1-3}$-alkyl or naphthyl-$C_{1-3}$-alkyl group optionally substituted in the aryl moiety by a halogen atom, a cyano, a $C_{1-3}$-alkyl or a methoxy group,
a 2-phenyl-2-hydroxy-ethyl group,
a phenylcarbonylmethyl group,
  wherein the phenyl group may be substituted by a hydroxy, $C_{1-3}$-alkyloxy, amino-carbonyl-$C_{1-3}$-alkoxy, ($C_{1-3}$-alkylamino)-carbonyl-$C_{1-3}$-alkoxy, [di-($C_{1-3}$-alkyl)-amino]-carbonyl-$C_{1-3}$-alkoxy, amino, $C_{1-3}$-alkyl-carbonylamino, $C_{3-6}$-cycloalkyl-carbonylamino, $C_{1-3}$-alkoxy-carbonylamino, $C_{1-3}$-alkylsulphonylamino or aminocarbonyl group,
a (3-methyl-2-oxo-2,3-dihydro-benzoxazolyl)-carbonylmethyl group,
a thienylcarbonylmethyl group,
a heteroaryl-$C_{1-3}$-alkyl group,
  while by the phrase "heteroaryl group" is meant a monocyclic 5- or 6-membered heteroaryl group optionally substituted by one or two $C_{1-3}$-alkyl groups or by a morpholin-4-yl, pyridyl or phenyl group, while
  the 6-membered heteroaryl group contains one, two or three nitrogen atoms and
  the 5-membered heteroaryl group contains an imino group optionally substituted by a $C_{1-3}$-alkyl or phenyl-$C_{1-3}$-alkyl group, or an oxygen or sulphur atom or
  an imino group optionally substituted by a $C_{1-3}$-alkyl or phenyl-$C_{1-3}$-alkyl group or an oxygen or sulphur atom and additionally contains a nitrogen atom or
  an imino group optionally substituted by a $C_{1-3}$-alkyl or phenyl-$C_{1-3}$-alkyl group or an oxygen or sulphur atom and additionally contains two or three nitrogen atoms,
  and additionally a phenyl ring, which may optionally be substituted by a halogen atom, by one or two $C_{1-3}$-alkyl groups or by a trifluoromethyl or methoxy group, may be fused to the above-mentioned monocyclic heteroaryl groups via two adjacent carbon atoms
  and the bond may be formed via an atom of the heterocyclic moiety or of the fused-on phenyl ring,
a bicyclic heteroarylmethyl group according to one of the formulae

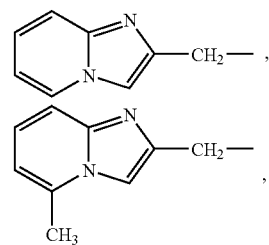

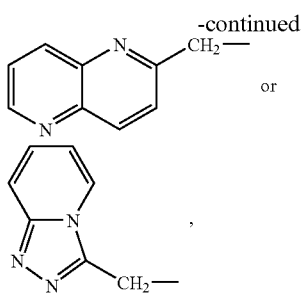

a group of formula

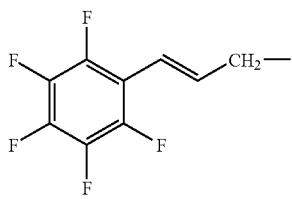

or a group of formulae

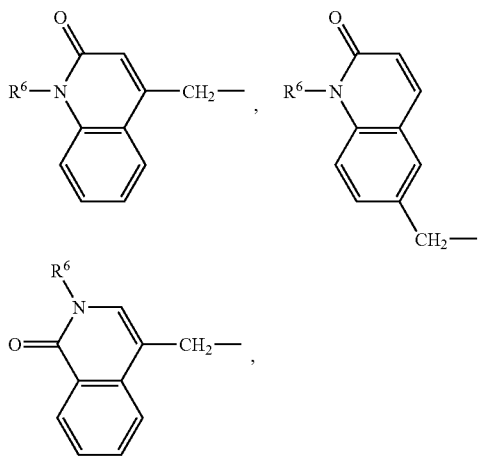

wherein R⁶ in each case denotes a hydrogen atom or a methyl group,
and R⁴ denotes a hydrogen atom or a $C_{1-3}$-alkyl group,
while unless otherwise stated the alkyl and alkoxy groups listed in the definitions which have more than two carbon atoms may be straight-chain or branched,
and the hydrogen atoms of the methyl or ethyl groups listed in the definitions may be wholly or partly replaced by fluorine atoms.

Preferred compounds of general formula I are those wherein
X denotes a nitrogen atom or a methyne group,
R¹ denotes a piperazin-1-yl, 3-amino-piperidin-1-yl, 3-amino-3-methyl-piperidin-1-yl, 3-amino-pyrrolidin-1-yl, 1,4-diazepan-1-yl, (2-amino-cyclohexyl)-amino or piperidin-3-yl-amino group,
R² denotes a benzyl group wherein the phenyl group may be substituted by one or two fluorine atoms, by a chlorine or bromine atom or by a cyano group, a straight-chain or branched $C_{3-8}$-alkenyl group,
a propyn-3-yl or but-2-yn-4-yl group,
a cyclopropylmethyl group,
a $C_{5-7}$-cycloalkenylmethyl group,
or a furylmethyl or thienylmethyl group,
R³ denotes a straight-chain or branched $C_{1-6}$-alkyl group,
a phenyl-$C_{1-2}$-alkyl or naphthyl-$C_{1-2}$-alkyl group optionally substituted in the aryl moiety by a fluorine, chlorine or bromine atom or by a cyano, $C_{1-3}$-alkyl or methoxy group,
a 2-phenyl-2-hydroxy-ethyl group,
a phenylcarbonylmethyl group,
wherein the phenyl group may be substituted by a hydroxy, $C_{1-3}$-alkyloxy, amino-carbonyl-$C_{1-3}$-alkoxy, ($C_{1-3}$-alkylamino)-carbonyl-$C_{1-3}$-alkoxy, [di-($C_{1-3}$-alkyl)-amino]-carbonyl-$C_{1-3}$-alkoxy, amino, $C_{1-3}$-alkyl-carbonylamino, $C_{3-6}$-cycloalkyl-carbonylamino, $C_{1-3}$-alkoxy-carbonylamino, $C_{1-3}$-alkylsulphonylamino or aminocarbonyl group,
a (3-methyl-2-oxo-2,3-dihydro-benzoxazolyl)-carbonylmethyl group,
a thienylcarbonylmethyl group,
a heteroaryl-methyl group,
while by the phrase a "heteroaryl group" is meant a pyridinyl, pyrimidinyl, pyridazinyl, pyrazinyl, thiazolyl, oxazolyl, isothiazolyl, isoxazolyl, pyrazolyl, imidazolyl, oxadiazolyl, thiadiazolyl or thienyl group optionally substituted by one or two methyl groups or by a pyridyl or phenyl group,
and while additionally a phenyl ring, which may optionally be substituted by a chlorine atom, by one or two methyl groups or by a trifluoromethyl or methoxy group, may be fused to the above-mentioned monocyclic heteroaryl groups via two adjacent carbon atoms
and the bond may be formed via an atom of the heterocyclic moiety or of the fused-on phenyl ring,
an imidazo[1,2-a]pyridin-2-yl-methyl group of formulae

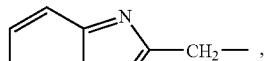

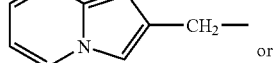

or

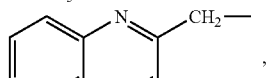

a 1,2,4-triazolo[4,3-a]pyridin-3-yl group of formula

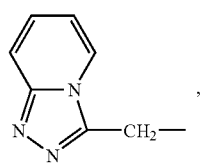

or a group of formulae

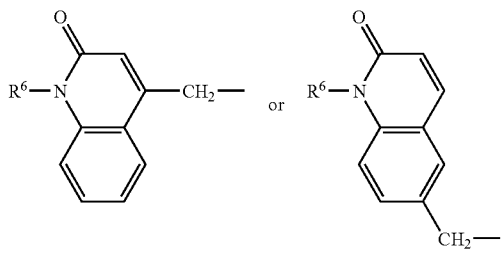

wherein R⁶ in each case denotes a hydrogen atom or a methyl group,
and R⁴ denotes a hydrogen atom or a methyl group,
while unless otherwise stated the alkyl and alkoxy groups listed in the definitions which have more than two carbon atoms may be straight-chain or branched,
and the hydrogen atoms of the methyl or ethyl groups listed in the definitions may be wholly or partly replaced by fluorine atoms,
the tautomers, the enantiomers, the diastereomers, the mixtures thereof and the salts thereof,
but particularly those compounds of general formula I wherein
X, R², R³ and R⁴ are as hereinbefore defined and
R¹ denotes a 3-amino-piperidin-1-yl group,
the tautomers, the enantiomers, the diastereomers, the mixtures thereof and the salts thereof.

A second sub-group of preferred compounds comprises those compounds of general formula I wherein
X, R¹, R³ and R⁴ are as hereinbefore defined and
R² denotes a 3-methylallyl, a 3,3-dimethylallyl or a but-2-yn-4-yl group,
the tautomers, the enantiomers, the diastereomers, the mixtures thereof and the salts thereof.

Particularly preferred are the following compounds of general formula I:

(1) 2-(3-amino-piperidin-1-yl)-3-(but-2-ynyl)-5-(naphthalen-1-ylmethyl)-3,5-dihydro-imidazo[4,5-d]pyridazin-4-one

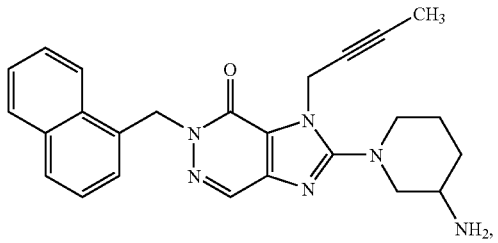

(2) 2-(3-amino-piperidin-1-yl)-3-but-2-ynyl-5-(3-methyl-isoquinolin-1-ylmethyl)-3,5-dihydro-imidazo[4,5-d]pyridazin-4-one,

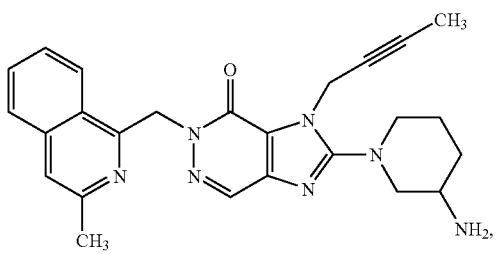

(3) 2-(3-amino-piperidin-1-yl)-3-(but-2-ynyl)-5-(quinazolin-2-ylmethyl)-3,5-dihydro-imidazo[4,5-d]pyridazin-4-one

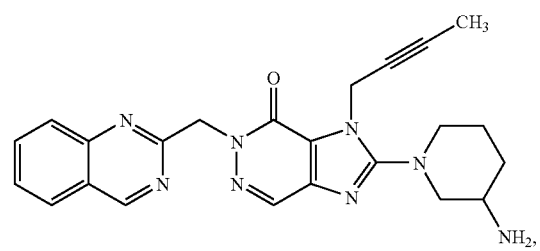

(4) 2-((R)-3-amino-piperidin-1-yl)-3-(but-2-ynyl)-5-(4-methyl-quinazolin-2-yl-methyl)-3,5-dihydro-imidazo[4,5-d]pyridazin-4-one

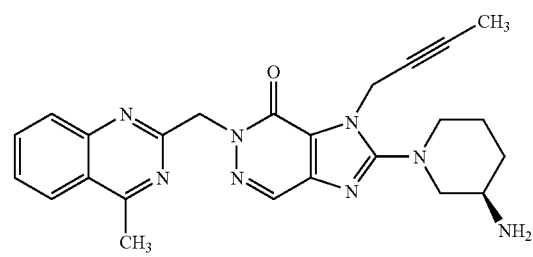

(5) 2-((R)-3-amino-piperidin-1-yl)-3-(but-2-ynyl)-5-(4-cyano-naphthalen-1-ylmethyl)-3,5-dihydro-imidazo[4,5-d]pyridazin-4-one

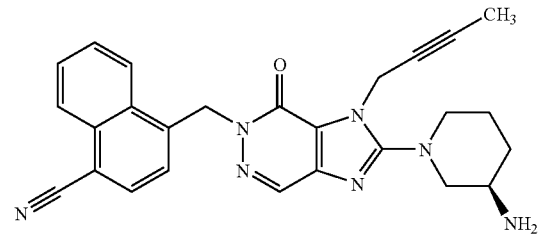

(6) 2-((R)-3-amino-piperidin-1-yl)-3-(but-2-ynyl)-5-(4-bromonaphth-1-ylmethyl)-3,5-dihydro-imidazo[4,5-d]pyridazin-4-one

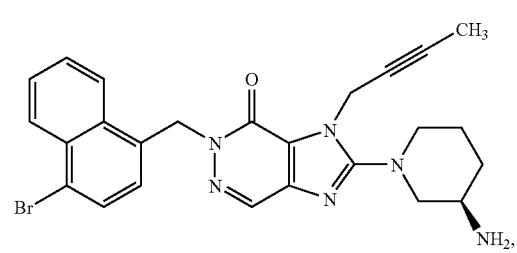

(7) 2-((R)-3-amino-piperidin-1-yl)-3-(but-2-ynyl)-5-(benzo[1,2,5]thiadiazol-5-yl-methyl)-3,5-dihydro-imidazo[4,5-d]pyridazin-4-one

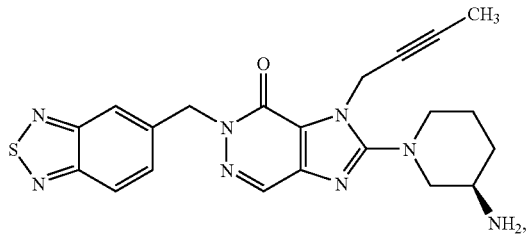

(8) 2-((R)-3-amino-piperidin-1-yl)-3-(2-chlorobenzyl)-5-(3-methyl-isoquinolin-1-ylmethyl)-3,5-dihydro-imidazo[4,5-d]pyridazin-4-one

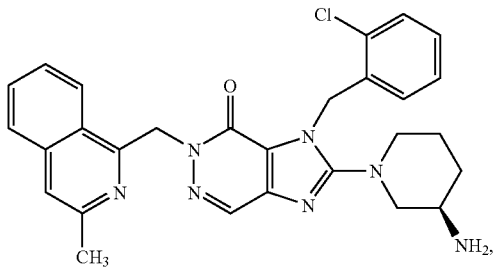

(9) 2-(3-amino-piperidin-1-yl)-3-(but-2-ynyl)-5-(quinoxalin-6-ylmethyl)-3,5-dihydro-imidazo[4,5-d]pyridazin-4-one

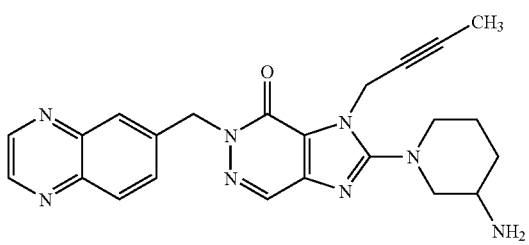

(10) 2-((R)-3-amino-piperidin-1-yl)-3-(but-2-ynyl)-5-(2,3-dimethyl-quinoxalin-6-yl-methyl)-3,5-dihydro-imidazo[4,5-d]pyridazin-4-one

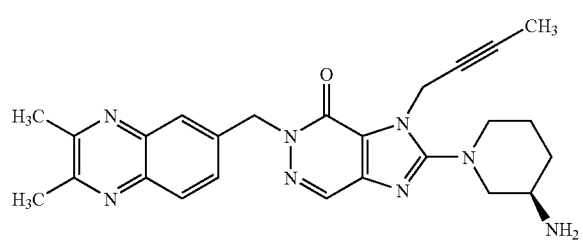

(11) 2-((R)-3-amino-piperidin-1-yl)-3-(but-2-ynyl)-5-(5-methyl-imidazo[1,2-a]pyridin-2-ylmethyl)-3,5-dihydro-imidazo[4,5-d]pyridazin-4-one

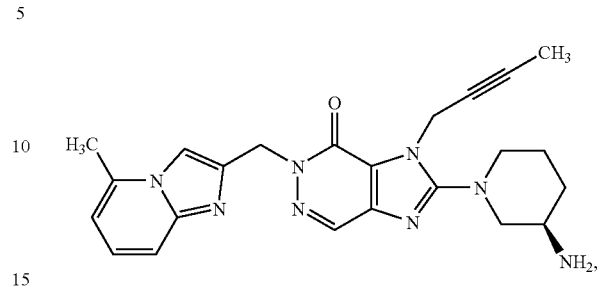

(12) 2-((R)-3-amino-piperidin-1-yl)-3-(but-2-ynyl)-5-(1-methyl-1H-quinolin-2-on-6-ylmethyl)-3,5-dihydro-imidazo[4,5-d]pyridazin-4-one

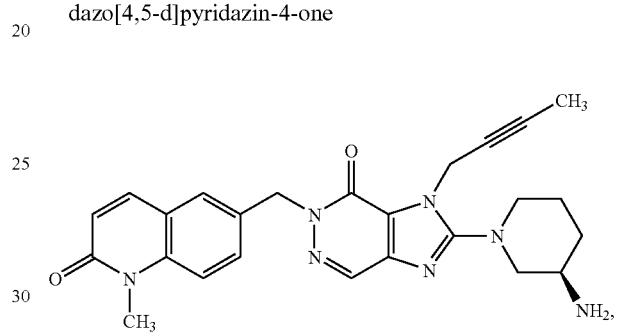

(13) 2-((R)-3-amino-piperidin-1-yl)-3-(but-2-ynyl)-5-(4-methyl-phthalazin-1-yl-methyl)-3,5-dihydro-imidazo[4,5-d]pyridazin-4-one

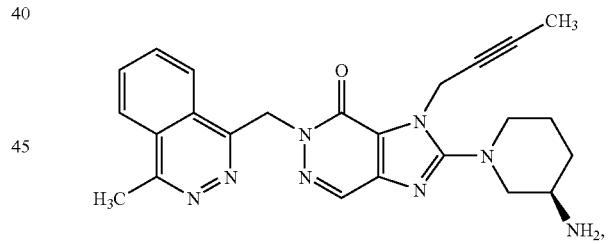

(14) 2-((R)-3-amino-piperidin-1-yl)-3-(but-2-ynyl)-5-([1,5]naphthyridin-2-ylmethyl)-3,5-dihydro-imidazo[4,5-d]pyridazin-4-one

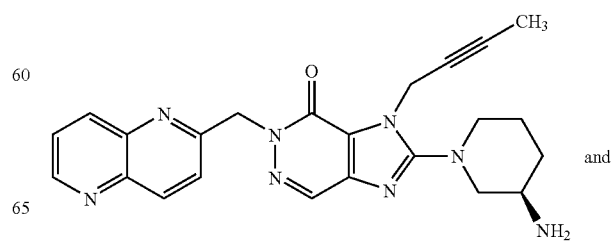

and

(15) 2-((R) -3-amino-piperidin-1-yl)-3-(but-2-ynyl)-5-(2,3, 8-trimethyl-quinoxalin-6-yl-methyl)-3,5-dihydro-imidazo[4,5-d]pyridazin-4-one

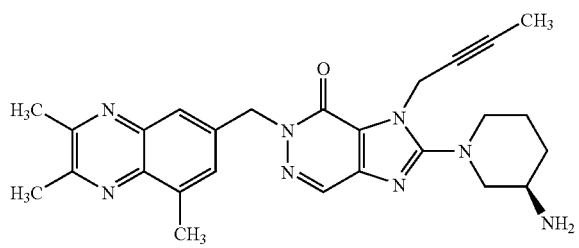

and the enantiomers and the salts thereof.

According to the invention the compounds of general formula I are obtained by methods known per se, for example by the following methods:

a) reacting a compound of general formula

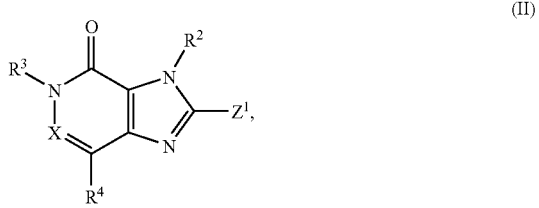

wherein X, $R^2$, $R^3$ and $R^4$ are as hereinbefore defined and $Z^1$ denotes a nucleofugic leaving group such as for example a chlorine or bromine atom or a $C_{1-3}$-alkylsulphanyl, $C_{1-3}$-alkylsulphinyl or $C_{1-3}$-alkylsulphonyl group, with an amine of general formula

wherein $R^1$ is as hereinbefore defined.

The reaction is expediently carried out in a solvent such as isopropanol, butanol, tetrahydrofuran, dioxane, dimethylformamide, dimethylsulphoxide, ethyleneglycol-monomethylether, ethyleneglycoldiethylether or sulpholane, optionally in the presence of an inorganic or tertiary organic base, e.g. sodium carbonate, potassium carbonate or potassium hydroxide, a tertiary organic base, e.g. triethylamine, or in the presence of N-ethyl-diisopropylamine (Hünig base), while these organic bases may simultaneously also serve as solvent, and optionally in the presence of a reaction accelerator such as an alkali metal halide or a palladium-based catalyst at temperatures between −20 and 180° C., but preferably at temperatures between −10 and 120° C. The reaction may however also be carried out without a solvent or in an excess of the amine of general formula $R^{4'}$—H.

b) deprotecting a compound of general formula

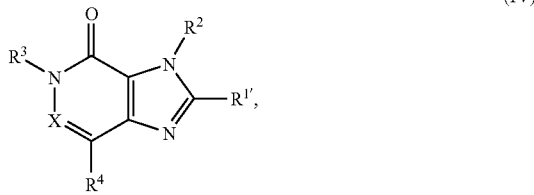

wherein $R^2$, $R^3$ and $R^4$ are as hereinbefore defined and $R^{1'}$ denotes one of the groups mentioned for $R^1$ hereinbefore, wherein the imino, amino or alkylamino group is substituted by a protective group.

The liberating of an amino group from a protected precursor is a standard reaction in synthetic organic chemistry. There are many examples of suitable protective groups. A summary of the chemistry of protective groups can be found in Theodora W. Greene and Peter G. M. Wuts, Protective Groups in Organic Synthesis, Second Edition, 1991, published by John Wiley and Sons, and in Philip J. Kocienski, Protecting Groups, published by Georg Thieme, 1994.

The following are examples of protective groups:

the tert.-butyloxycarbonyl group which can be cleaved by treating with an acid such as for example trifluoroacetic acid or hydrochloric acid or by treating with bromotrimethylsilane or iodotrimethylsilane, optionally using a solvent such as methylene chloride, ethyl acetate, dioxane, methanol, isopropanol or diethylether at temperatures between 0° C. and 80° C., the 2,2,2-trichloroethoxycarbonyl group which can be cleaved by treating with metals such as for example zinc or cadmium in a solvent such as acetic acid or a mixture of tetrahydrofuran and a weak aqueous acid at temperatures between 0° C. and the boiling temperature of the solvent used and the carbobenzyloxycarbonyl group which can be cleaved for example by hydrogenolysis in the presence of a noble metal catalyst such as for example palladium-charcoal and a solvent such as for example alcohols, ethyl acetate, dioxane, tetrahydrofuran or mixtures of these solvents at temperatures between 0° C. and the boiling point of the solvent, by treating with boron tribromide in methylene chloride at temperatures between −20° C. and ambient temperature, or by treating with aluminium chloride/anisol at temperatures between 0° C. and ambient temperature.

If desired any protecting group used to protect reactive groups during the reactions is subsequently cleaved and/or a compound of general formula I thus obtained is resolved into its stereoisomers and/or a compound of general formula I thus obtained is converted into the salts thereof, particularly for pharmaceutical use into the physiologically acceptable salts thereof with an inorganic or organic acid.

In the reactions described hereinbefore, any reactive groups present such as hydroxy, carboxy, phosphono, O-alkyl-phosphono, amino, alkylamino or imino groups may be protected during the reaction by conventional protecting groups which are cleaved again after the reaction.

For example, a protecting group for a hydroxy group may be a trimethylsilyl, acetyl, benzoyl, methyl, ethyl, tert.butyl, trityl, benzyl or tetrahydropyranyl group, protecting groups for a carboxy group may be a trimethylsilyl, methyl, ethyl, tert.butyl, benzyl or tetrahydropyranyl group, protecting groups for a phosphono group may be an alkyl group such as a methyl, ethyl, isopropyl or n-butyl group, a phenyl or benzyl group and protecting groups for an amino, alkylamino or imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example, hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid or by treating with iodotrimethylsilane, optionally using a solvent such as methylene chloride, dioxane, methanol or diethylether.

A trifluoroacetyl group is preferably cleaved by treating with an acid such as hydrochloric acid, optionally in the presence of a solvent such as acetic acid, at temperatures between 50 and 120° C. or by treating with sodium hydroxide solution, optionally in the presence of a solvent such as tetrahydrofuran at temperatures between 0 and 50° C.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

A single alkyl group may be cleaved from an O,O'-dialkylphosphono group with sodium iodide, for example, in a solvent such as acetone, methylethylketone, acetonitrile or dimethylformamide at temperatures between 40 and 150° C., but preferably at temperatures between 60 and 100° C.

Both alkyl groups may be cleaved from an O,O'-dialkylphosphono group with iodotrimethylsilane, bromotrimethylsilane or chlorotrimethylsilane/sodium iodide, for example, in a solvent such as methyl chloride, chloroform or acetonitrile at temperatures between 0° C. and the boiling temperature of the reaction mixture, but preferably at temperatures between 20 and 60° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-O-p-toluoyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formulae II to IV used as starting materials are either known from the literature or may be obtained by methods known from the literature, for example using the methods of synthesis illustrated in Diagrams 1 to 5. The method of synthesis shown in Diagram 4 is preferred.

Diagram 1:
Possible method of synthesising the substituted
3,5-dihydro-imidazo[4,5-c]pyridin-4-ones

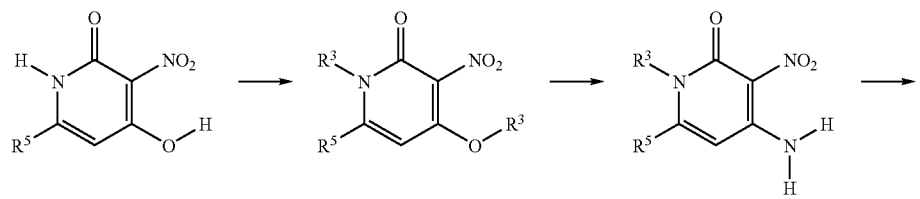

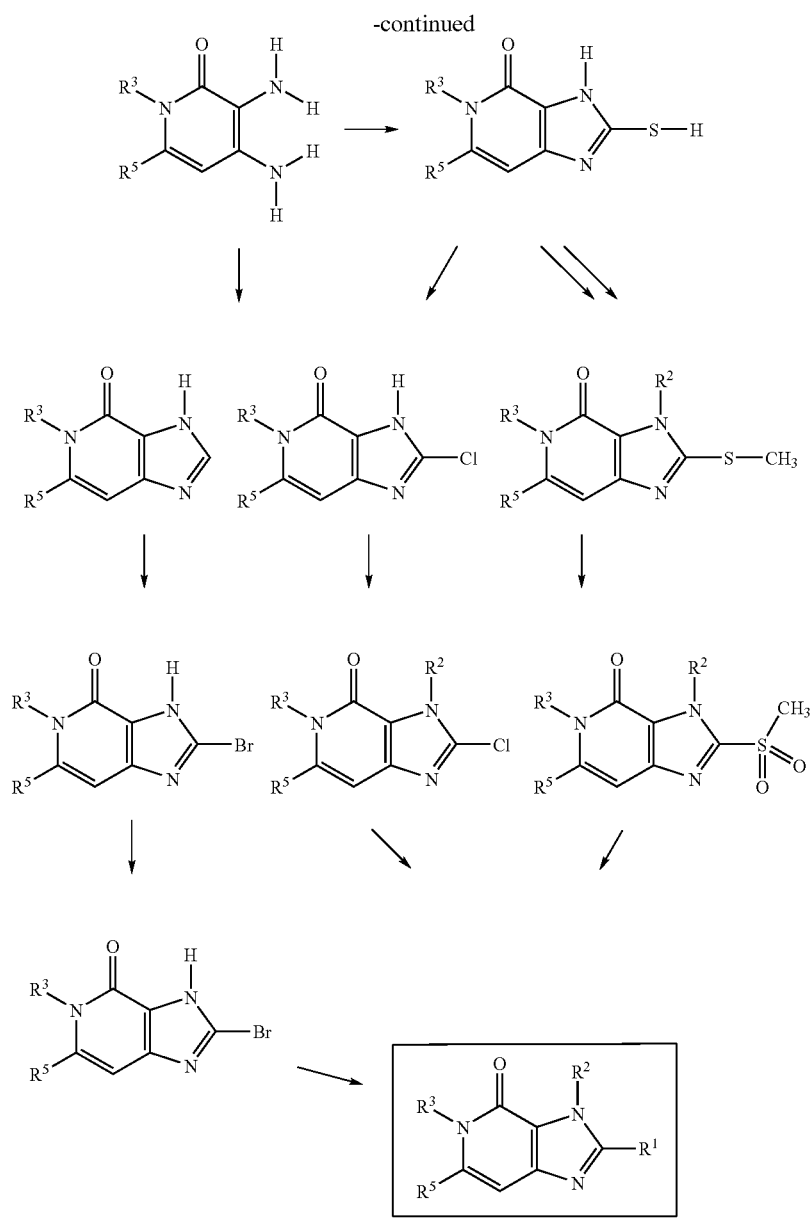
Diagram 2:
Possible alternative method of synthesising the substituted 3,5-dihydro-imidazo[4,5-c]pyridin-4-ones

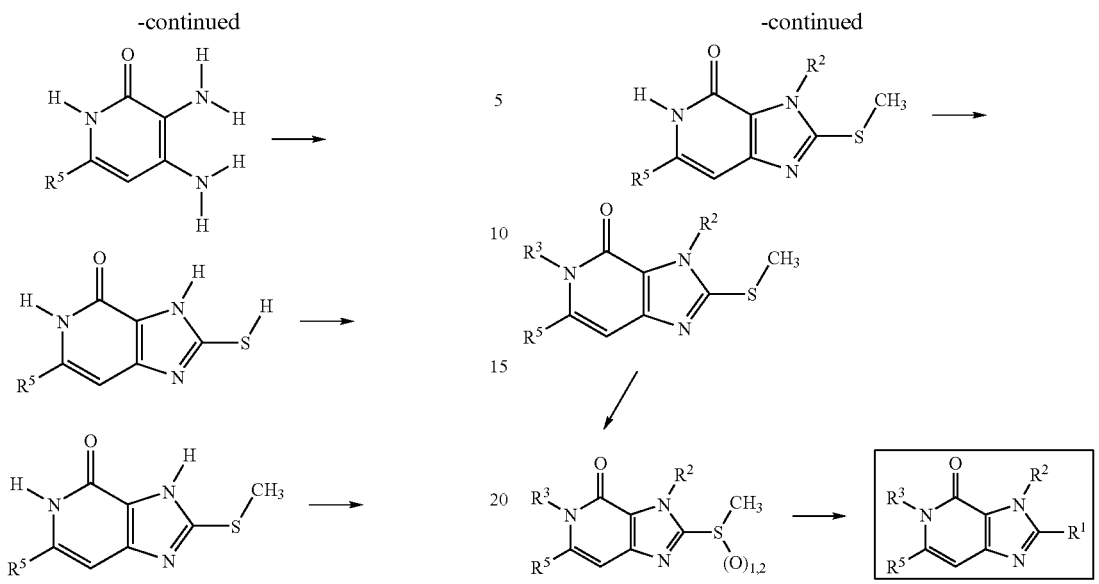
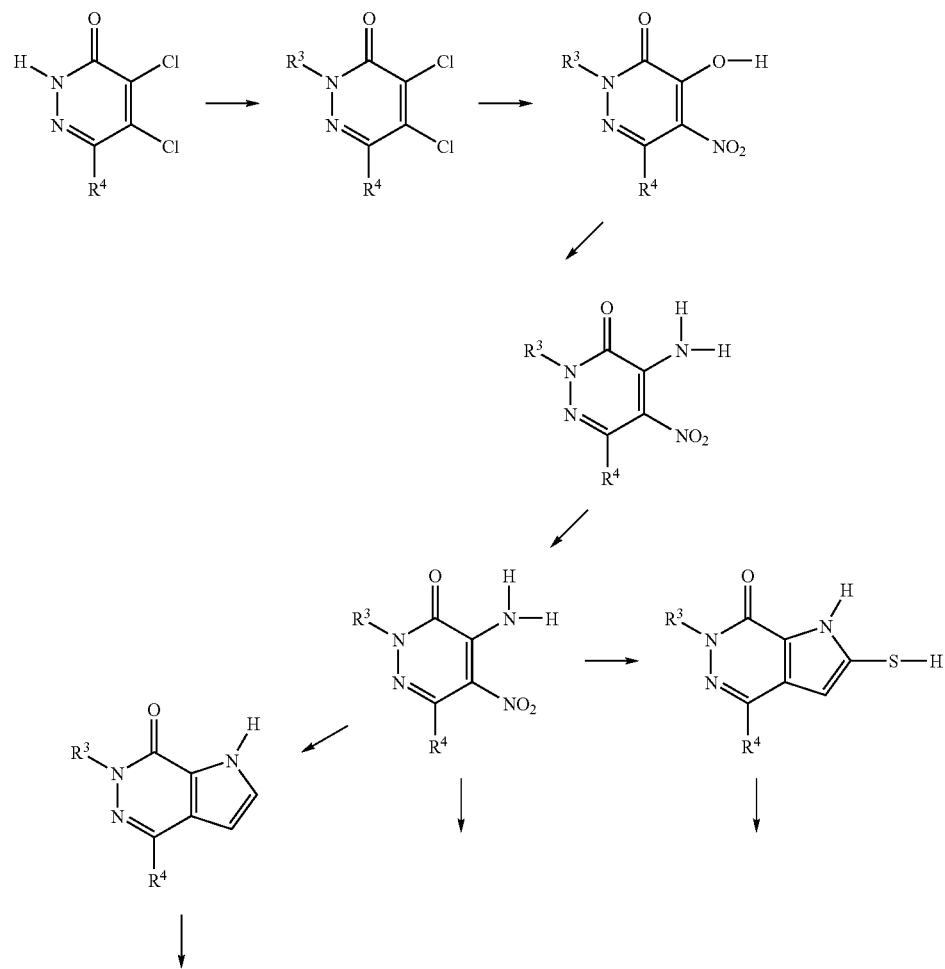
Diagram 3:
Possible method of synthesising the substituted
3,5-dihydro-imidazo[4,5-d]pyridazin-4-ones

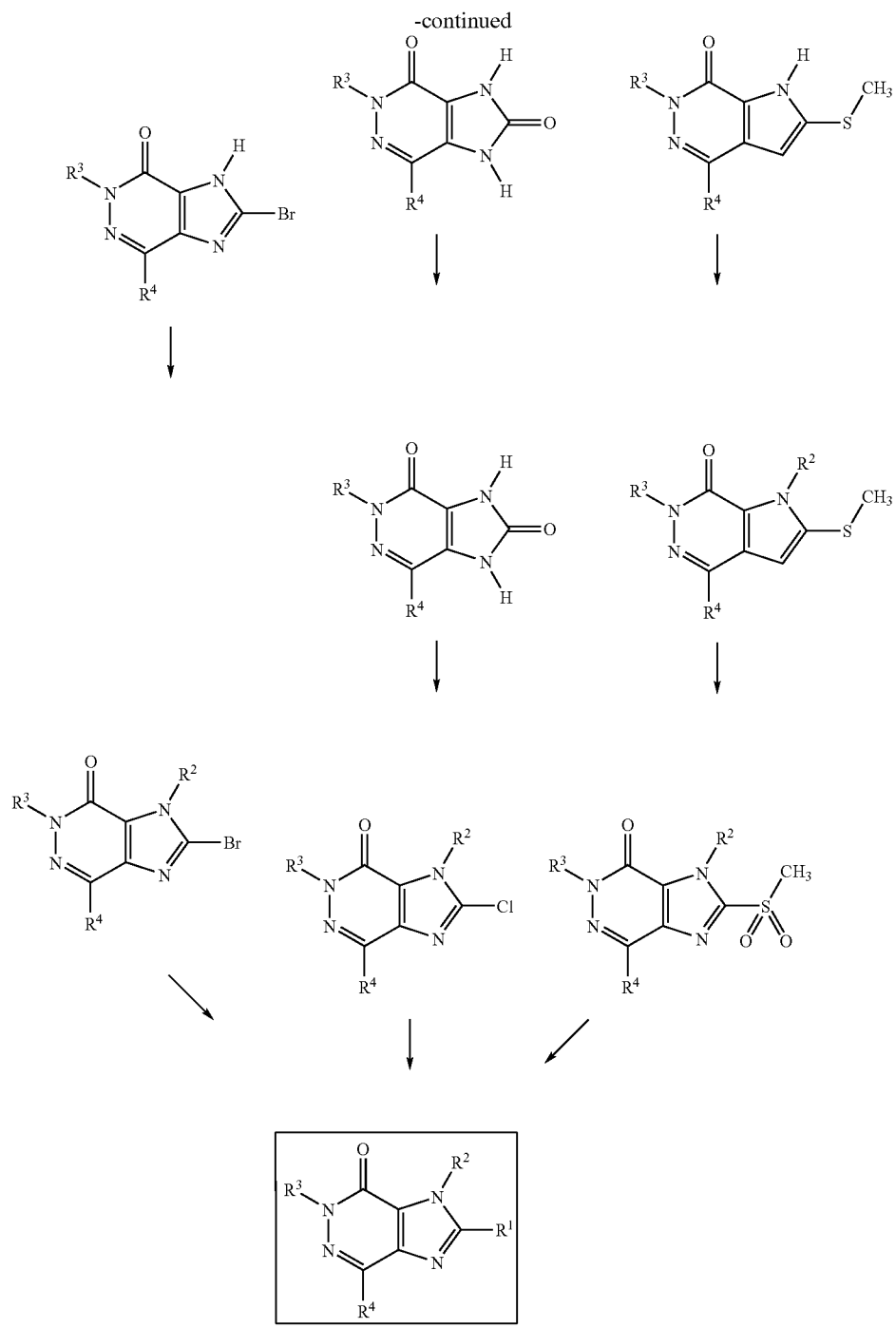
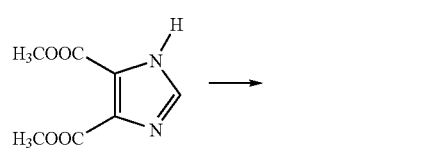
Diagram 4:
Possible alternative method of synthesising the substituted 3,5-dihydro-imidazo[4,5-d]pyridazin-4-ones
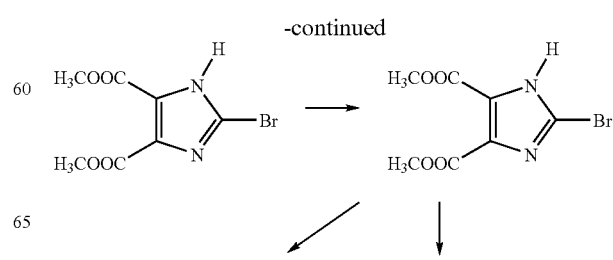

-continued

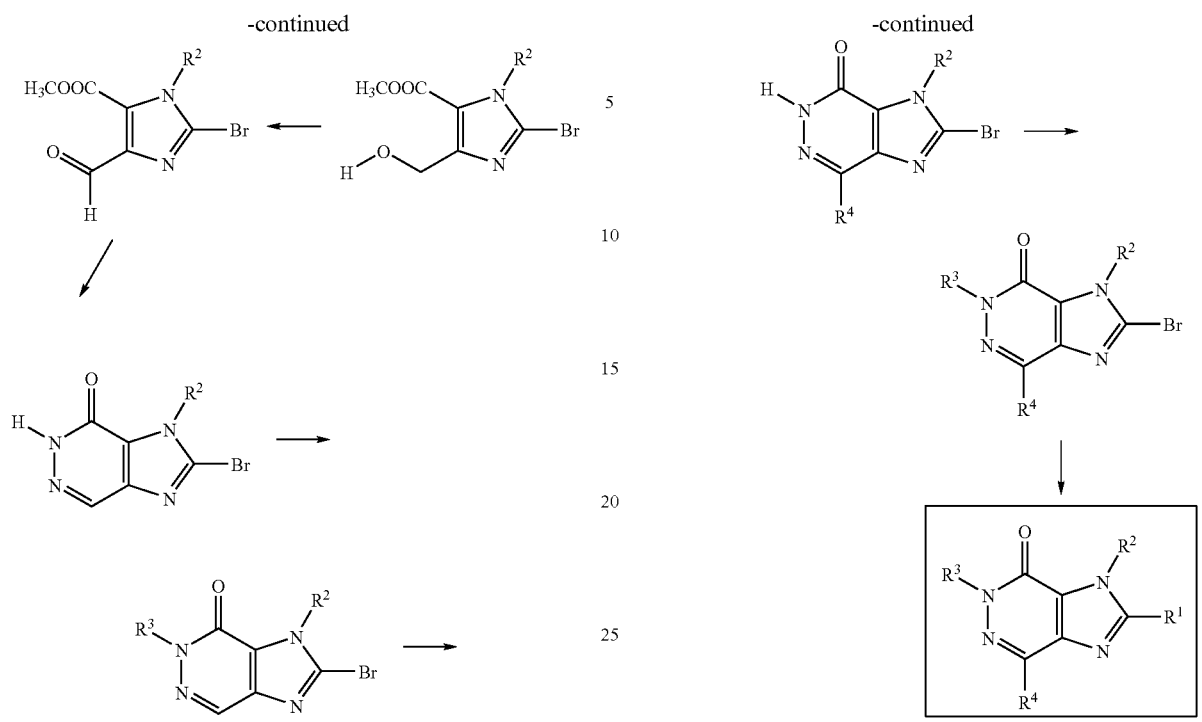

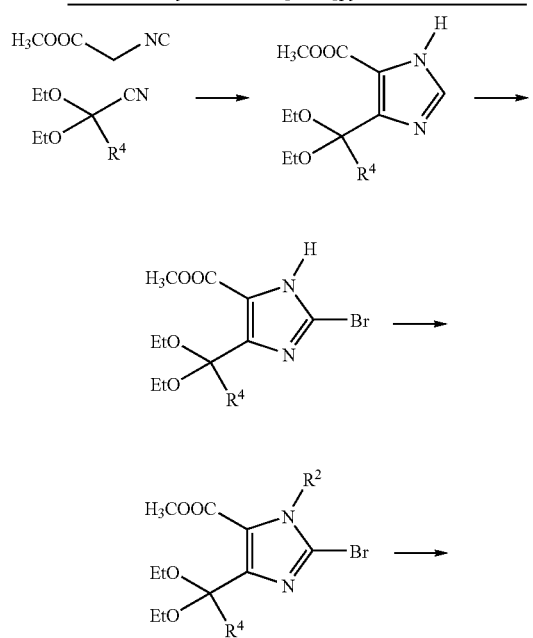

Diagram 5:
Another possible method of synthesising the substituted 3,5-dihydro-imidazo[4,5-d]pyridazin-4-ones As already mentioned hereinbefore, the compounds of general formula I according to the invention and the physiologically acceptable salts thereof have valuable pharmacological properties, particularly an inhibiting effect on the enzyme DPP-IV.

The biological properties of the new compounds were investigated as follows:

The ability of the substances and their corresponding salts to inhibit the DPP-IV activity can be demonstrated in a test set-up in which an extract of human colon carcinoma cell line Caco-2 is used as the DPP IV source. The differentiation of the cells in order to induce the DPP-IV expression was carried out as described by Reiher et al. in an article entitled "Increased expression of intestinal cell line Caco-2", which appeared in Proc. Natl. Acad. Sci. Vol. 90, pages 5757–5761 (1993). The cell extract was obtained from cells solubilised in a buffer (10 mM Tris HCl, 0.15 M NaCl, 0.04 t.i.u. aprotinin, 0.5% Nonidet-P40, pH 8.0) by centrifuging at 35,000 g for 30 minutes at 4° C. (to remove cell debris).

The DPP-IV assay was carried out as follows:

50 μl substrate solution (AFC; AFC is amido-4-trifluoromethylcoumarin), final concentration 100 μM, were placed in black microtitre plates. 20 μl of assay buffer (final concentrations 50 mM Tris HCl pH 7.8, 50 mM NaCl, 1% DMSO) was pipetted in. The reaction was started by adding 30 μl of solubilised Caco-2 protein (final concentration 0.14 μg of protein per well). The test substances to be investigated were typically added prediluted in 20 μl, and the volume of assay buffer was then reduced accordingly. The reaction was carried out at ambient temperature, incubating for 60 minutes. Then the fluorescence was measured in a Victor 1420 Multilabel Counter, the excitation wavelength being 405 nm and the emission wavelength being 535 nm. Blank readings (corresponding to 0% activity) were obtained in mixtures without any Caco-2 protein (volume replaced by assay buffer), control values (corresponding to 100% activity) were obtained in mixtures with no substance added. The potency of the test substances in question, expressed as $IC_{50}$ values, was calculated from dosage/activity curves consisting of 11 measuring points in each case. The following results were obtained:

| Compound (Example no.) | DPP-IV inhibition $IC_{50}$ [nM] |
|---|---|
| 2 | 13 |
| 7 | 5.4 |
| 182 | 1.2 |
| 191 | 14 |
| 195 | 17 |
| 202 | 9.8 |
| 205 | 5.4 |
| 217 | 10 |

The compounds prepared according to the invention are well tolerated, as for example when 10 mg/kg of the compound of Example 2 were administered to rats by oral route no changes in the animals' behaviour could be detected.

In view of their ability to inhibit DPP-IV activity, the compounds of general formula I according to the invention and the corresponding pharmaceutically acceptable salts thereof are suitable for treating all those conditions or illnesses which can be influenced by the inhibition of the DPP-IV activity. It is therefore to be expected that the compounds according to the invention will be suitable for the prevention or treatment of diseases or conditions such as type I and type II diabetes mellitus, diabetic complications, metabolic acidosis or ketosis, insulin resistance, dyslipidaemias of various origins, arthritis, atherosclerosis and related diseases, obesity, allograft transplantation and calcitonin-induced osteoporosis. In addition these substances are capable of preventing B-cell degeneration such as e.g. apoptosis or necrosis of pancreatic B-cells. The substances are also suitable for improving or restoring the function of pancreatic cells and also increasing the number and size of pancreatic B-cells. Additionally, and on the basis of the role of the Glucagon-Like Peptides, such as e.g. GLP-1 and GLP-2 and their link with DPP-IV inhibition, it is likely that the compounds according to the invention are suitable for achieving, inter alia, a sedative or anxiety-relieving effect and also of favourably affecting catabolic states after operations or hormonal stress responses or of reducing mortality or morbidity after myocardial infarct. They are also suitable for treating all conditions which are connected with the above-mentioned effects and which are mediated by GLP-1 or GLP-2. The compounds according to the invention may also be used as diuretics or antihypertensives and are suitable for preventing and treating acute renal failure. They are also suitable for the prevention and treatment of chronic inflammatory intestinal diseases. It is also expected that DPP-IV inhibitors and hence also the compounds according to the invention may be used to treat infertility or to improve fertility in humans or mammals, particularly when the infertility is connected with insulin resistance or polycystic ovary syndrome. The substances are also suitable for treating deficiencies of growth hormone which are associated with reduced stature.

The compounds according to the invention may also be used in conjunction with other active substances. Therapeutic agents which are suitable for such combinations include, for example, antidiabetics, such as metformin, sulphonylureas (e.g. glibenclamid, tolbutamide, glimepiride), nateglinide, repaglinide, thiazolidinedione (e.g. rosiglitazone, pioglitazone), PPAR-gamma agonists (e.g. GI 262570), alpha-glucosidase inhibitors (e.g. acarbose, voglibose), alpha2 antagonists, insulin and insulin analogues, GLP-1 and GLP-1 analogues (e.g. exendin-4) or amylin. Also, inhibitors of protein tyrosine phosphatase 1, substances which influence deregulated glucose production in the liver, such as e.g. inhibitors of glucose-6-phosphatase, or fructose-1,6-bisphosphatase, glycogen-phosphorylase, glucagon receptor antagonists and inhibitors of phosphoenol pyruvate carboxykinase, glycogen synthase kinase or pyruvate dehydrokinase, lipid lowering agents, such as HMG-CoA-reductase inhibitors (e.g. simvastatin, atorvastatin), fibrates (e.g. bezafibrate, fenofibrate), nicotinic acid and its derivatives, cholesterol absorption inhibitors such as for example ezetimibe, bile acid-binding substances such as for example cholestyramine, HDL-raising compounds such as for example inhibitors of CETP or regulators of ABC 1 or active substances for the treatment of obesity, such as e.g. sibutramine or tetrahydrolipostatin, or $\beta_3$-agonists such as SB-418790 or AD-9677. It is also possible to combine the compounds with drugs for treating high blood pressure such as e.g. AII antagonists or ACE inhibitors, diuretics, β-blockers, etc., or combinations thereof.

The dosage required to achieve such an effect is expediently, by intravenous route, 1 to 100 mg, preferably 1 to 30 mg, and by oral route 1 to 1000 mg, preferably 1 to 100 mg, in each case 1 to 4 times a day. For this purpose, the compounds of formula I prepared according to the invention, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The Examples that follow are intended to illustrate the invention:

To synthesise the compounds which contain a chiral 3-amino-piperidin-1-yl group, the corresponding chiral reagent, namely (R)-3-(tert.-butyloxycarbonylamino)-piperidine, was used as starting material. (R)-3-(tert.-butyloxycarbonylamino)-piperidine was obtained starting from (R)-1-benzyl-3-(tert.-butyloxycarbonylamino)-piperidine, which was prepared analogously to the (S)-enantiomer known from the literature (see Moon, Sung-Hwan; Lee, Sujin; Synth.Commun.; 28; 21; 1998; 3919–3926), as follows: About 2 g of (R)-1-benzyl-3-(tert.-butyloxycarbonylamino)-piperidine in 20 ml of methanol are hydrogenated for 24 hours at ambient temperature at a hydrogen pressure of 3 bar in the presence of 200 mg palladium on activated charcoal (10% Pd). Then the catalyst is removed by suction filtering and the filtrate is evaporated to dryness.

melting point: 119° C.

Mass spectrum (ESI+): m/z=201 [M+H]+

EXAMPLE 1

2-(3-Amino-piperidin-1-yl)-3-benzyl-5-(naphthalen-1-ylmethyl)-3,5-dihydro-imidazo[4,5-d]pyridazin-4-one

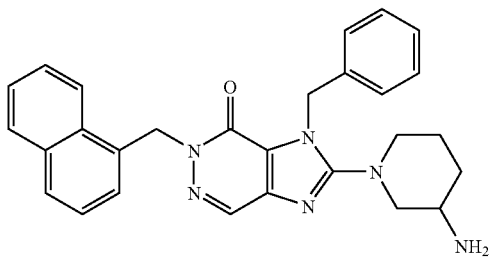

1a) 4,5-dichloro-2-naphthalen-1-ylmethyl-2H-pyridazin-3-one

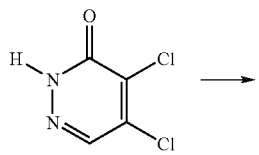

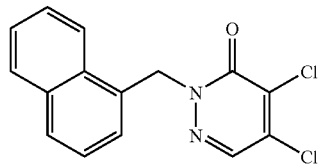

9.0 g (65 mmol) of potassium carbonate were added to a solution of 10.0 g (60.61 mmol) of 4,5-dichloro-3-hydroxy-pyridazine in 50 ml dimethylsulphoxide, then 9.42 g (63 mmol) of 1-(chloromethyl)-naphthalene were added and the mixture was stirred for 17 hours at 50° C. The dark solution was cooled and then combined with 300 ml of dist. water, then 300 ml dichloromethane were stirred in, the mixture was suction filtered through Celite, the aqueous phase was separated off and extracted another three times with 50 ml of dichloromethane. The combined organic phases were washed with water, dried over sodium sulphate and evaporated down. The crude product thus obtained was dissolved in 250 ml dichloromethane, the solution was filtered through silica gel and then evaporated down. The residue was triturated with petroleum ether, suction filtered and dried.

Yield: 67.6% of theory.
$C_{15}H_{10}Cl_2N_2O$ (305.17)
Rf value: 0.71 (silica gel, dichloromethane)
Mass spectrum: $(M+H)^+=305/7$ (Cl)

1b) 4-hydroxy-2-naphthalen-1-ylmethyl-5-nitro-2H-pyridazin-3-one

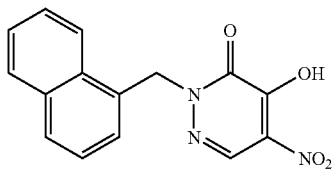

A solution of 11.04 g (160 mmol) of sodium nitrite in 40 ml of water was added to a solution of 12 g (39.3 mmol) of 4,5-dichloro-2-naphthalen-1-ylmethyl-2H-pyridazin-3-one in 120 ml of dimethylformamide and the mixture was stirred for 24 hours at 85° C.

Then it was evaporated down in vacuo and the residue was stirred with a mixture of 30 ml semiconcentrated hydrochloric acid and 30 ml of ethanol, during which time the product crystallised. It was suction filtered, washed with ethanol and dried.

Yield: 81.7% of theory
$C_{15}H_{11}N_3O_4$ (297.27)
Rf value: 0.32 (silica gel, dichloromethane/ethanol 19:1)

1c) 4-amino-2-naphthalen-1-ylmethyl-5-nitro-2H-pyridazin-3-one

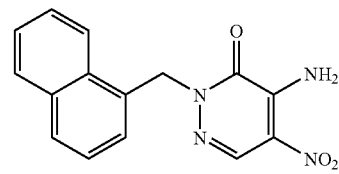

9.4 g (31.6 mmol) of 4-hydroxy-2-naphthalen-1-ylmethyl-5-nitro-2H-pyridazin-3-one were combined with 150 ml saturated methanolic ammonia solution and heated to 130° C. for 24 hours in a Roth bomb. The mixture was concentrated down to a volume of about 40 ml using the rotary evaporator, the product precipitated was suction filtered and recrystallised from tetrahydrofuran.

Yield: 53.4% of theory
$C_{15}H_{12}N_4O_3$ (296.29)
Rf value: 0.68 (silica gel, dichloromethane/ethanol 50:1)
Mass spectrum: $(M+H)^+=297$
$(M-H)^-=295$ 1d) 4,5-diamino-2-naphthalen-1-ylmethyl-2H-pyridazin-3-one

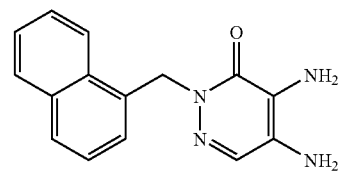

5 g (16.88 mmol) of 4-amino-2-naphthalen-1-ylmethyl-5-nitro-2H-pyridazin-3-one, dissolved in 150 ml of tetrahydrofuran, were reduced in a Parr apparatus with the addition of 250 mg of platinum oxide, at ambient temperature and under 2 atm $H_2$. The catalyst was filtered off, the filtrate was evaporated down and the crude product thus obtained was further processed without any more purification.

Yield: 99% of theory
$C_{15}H_{14}N_4O$ (266.3)
Rf value: 0.14 (silica gel, dichloromethane/ethanol 19:1)

1e) 2-mercapto-5-(naphthalen-1-ylmethyl)-3,5-dihydro-imidazo[4,5-d]pyridazin-4-one

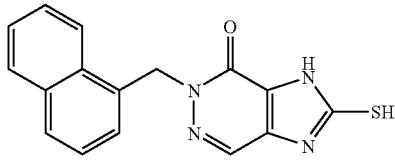

4.99 g (28.0 mmol) of N,N'-thiocarbonyldiimidazole were added to a solution of 4.4 g (16.5 mmol) of 4,5-diamino-2-naphthalen-1-ylmethyl-2H-pyridazin-3-one in 100 ml of tetrahydrofuran and stirred overnight at ambient temperature. Then the mixture was concentrated by evaporation in vacuo, the residue was combined with approx. 30 ml of water, made weakly acidic with hydrochloric acid, the product precipitated was suction filtered, washed with water and dried.

Yield: 98% of theory
$C_{16}H_{12}N_4OS$ (308.36)
Rf value: 0.22 (silica gel, dichloromethane/ethanol 19:1)
Mass spectrum: $(M-H)^-=307$ 1f) 2-methylsulphanyl-5-(naphthalen-1-ylmethyl)-3,5-dihydro-imidazo[4,5-d]pyridazin-4-one

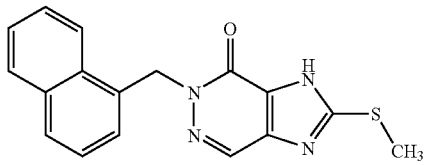

2.38 g (17.2 mmol) of potassium carbonate and 1.07 ml (17.20 mmol) of iodomethane were added to a suspension of 5.3 g (17.19 mmol) of 2-mercapto-5-(naphthalen-1-ylmethyl)-3,5-dihydro-imidazo[4,5-d]pyridazin-4-one in 100 ml of dichloromethane and 100 ml of methanol and stirred overnight at ambient temperature. Then the solvent was evaporated off, the residue was combined with approx. 30 ml of water, acidified with 2N hydrochloric acid, the product thus obtained was suction filtered, washed again with water and dried.

Yield: 54.1% of theory
$C_{17}H_{14}N_4OS$ (322.39)
Rf value: 0.70 (silica gel, dichloromethane/ethanol 50:1)
Mass spectrum: $(M+H)^+=323$
$^1$H-NMR spectrum ($d_6$-DMSO): δ=2.70 (s, 3H); 5.81 (s, 2H); 7.20 (dd, 1H); 7.43 (t, 1H); 7.57 (m, 2H); 7.86 (dd, 1H); 7.95 (dd, 1H); 8.29 (dd, 1H); 8.38 (s, 1H), 13.85 (broad s, 1H) ppm.

1g) 3-benzyl-2-methylsulphanyl-5-(naphthalen-1-ylmethyl)-3,5-dihydro-imidazo[4,5-d]pyridazin-4-one

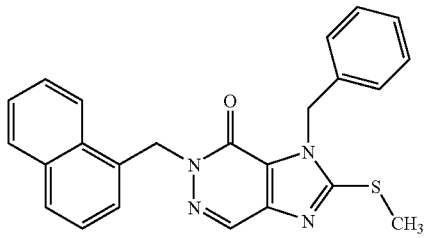

A solution of 1.0 g (3.10 mmol) of 2-methylsulphanyl-5-(naphthalen-1-ylmethyl)-3,5-dihydro-imidazo[4,5-d]pyridazin-4-one in 15 ml of dimethylformamide was combined with 547 mg (3.20 mmol) of benzylbromide and then with 442 mg (3.20 mmol) of potassium carbonate and stirred overnight at ambient temperature. Then it was diluted with approx. 40 ml of water and extracted three times with 15 ml of ethyl acetate. The organic extracts were washed with water, dried over sodium sulphate and evaporated down. The crude product thus obtained was purified by column chromatography (silica gel; eluant:petroleum ether with 10–20% ethyl acetate).

Yield: 54.7% of theory
$C_{24}H_{20}N_4OS$ (412.52)
Rf value: 0.77 (silica gel, petroleum ether/ethyl acetate 1:1)
Mass spectrum: $(M+H)^+=413$ 1h) 3-benzyl-2-methylsulphonyl-5-(naphthalen-1-ylmethyl)-3,5-dihydro-imidazo[4,5-d]pyridazin-4-one

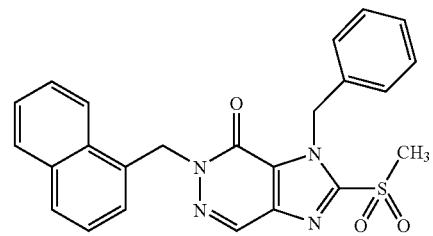

A solution of 395 mg (2.50 mmol) of potassium permanganate was added dropwise to a solution of 700 mg (1.70 mmol) of 3-benzyl-2-methylsulphanyl-5-(naphthalen-1-ylmethyl)-3,5-dihydro-imidazo[4,5-d]pyridazin-4-one in 30 ml concentrated acetic acid with stirring at ambient temperature and stirring was continued for a further two hours. As the oxidation was not yet complete, a further 150 mg potassium permanganate, dissolved in 5 ml of water, were added and the mixture was again stirred for two hours. The reaction solution was then combined with 0.5 g sodium hydrogen sulphite, then diluted with approx. 40 ml of water and extracted three times with 20 ml of dichloromethane. The organic extracts were washed with 5% sodium hydrogen sulphite solution, then with water and dried over sodium sulphate. The crude product obtained after evaporation was purified by column chromatography (silica gel; eluant: dichloromethane with 1% ethanol).

Yield: 55.7% of theory
$C_{24}H_{20}N_4O_3S$ (444.52)
Rf value: 0.41 (silica gel, petroleum ether/ethyl acetate 7:3)
Mass spectrum: $(M+H)^+=445$ 1i) tert.butyl [1-(1-benzyl-6-naphthalen-1-ylmethyl-7-oxo-6,7-dihydro-1H-imidazo[4 5-d]pyridazin-2-yl)-piperidin-3-yl]-carbaminate

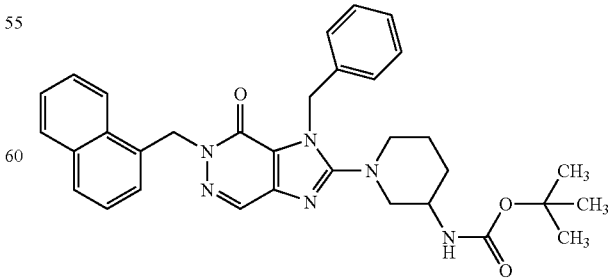

200 mg (0.45 mmol) of 3-benzyl-2-methylsulphonyl-5-(naphthalen-1-ylmethyl)-3,5-dihydro-imidazo[4,5-d]pyridazin-4-one and 600 mg (3.0 mmol) of tert.butyl piperidin-3-yl-carbaminate were stirred together for 16 hours at 150° C. under nitrogen. The reaction mixture was then dissolved in 30 ml dichloromethane, the solution was washed with 1N sodium hydroxide solution and dried over sodium sulphate. The crude product obtained after evaporation was purified by column chromatography (silica gel; eluant:dichloromethane with 1–2% ethanol).

Yield: 26.6% of theory $C_{33}H_{36}N_6O_3$ (564.69)

Rf value: 0.59 (silica gel, dichloromethane/ethanol 19:1)

Mass spectrum: $(M+H)^+=565$ 1j) 2-(3-amino-piperidin-1-yl)-3-benzyl-5-(naphthalen-1-ylmethyl)-3,5-dihydro-imidazo[4,5-d]pyridazin-4-one hydrochloride

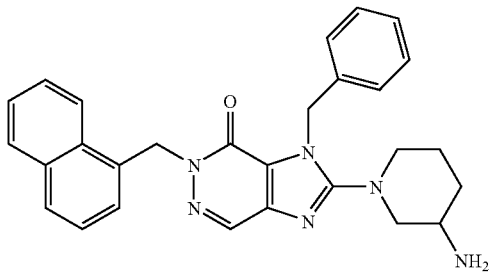

A solution of 60 mg (0.106 mmol) of tert.butyl [1-(1-benzyl-6-naphthalen-1-ylmethyl-7-oxo-6,7-dihydro-1H-imidazo[4,5-d]pyridazin-2-yl)-piperidin-3-yl]-carbaminate in 5 ml dichloromethane was combined with 0.5 ml trifluoroacetic acid and stirred for two hours at ambient temperature. The mixture was evaporated to dryness, the residue was dissolved in 5 ml dichloromethane and the solution was washed with 1N sodium hydroxide solution and water and then dried over sodium sulphate. It was again concentrated by evaporation, the residue was dissolved in a mixture of 3 ml each of diethyl ether and acetone and the hydrochloride of the product was precipitated by the dropwise addition of ethereal hydrochloric acid. This was suction filtered and dried.

Yield: 37.7% of theory $C_{28}H_{28}N_6O \times HCl$ (501.04)

Rf value: 0.22 (silica gel, dichloromethane/ethanol 19:1)

Mass spectrum: $(M+H)^+=465$

EXAMPLE 2

2-(3-amino-piperidin-1-yl)-3-(but-2-ynyl)-5-(naphthalen-1-ylmethyl)-3,5-dihydro-imidazo[4,5-d]pyridazin-4-one

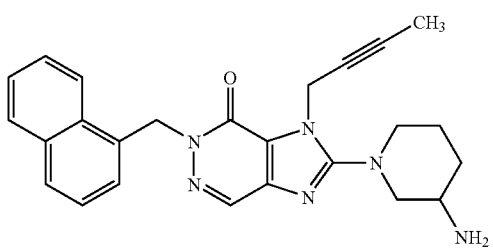

2a) 3-(but-2-ynyl)-2-methylsulphanyl-5-(naphthalen-1-ylmethyl)-3,5-dihydro-imidazo[4,5-d]pyridazin-4-one

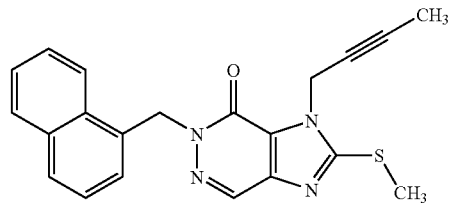

A solution of 900 mg (2.79 mmol) of 2-methylsulphanyl-5-(naphthalen-1-ylmethyl)-3,5-dihydro-imidazo[4,5-d]pyridazin-4-one (Example 1f) in 15 ml of dimethylformamide was combined with 415 mg (3.0 mmol) of potassium carbonate and 399 mg (3.0 mmol) of 1-bromo-2-butyne and stirred at ambient temperature for eight hours. Then the mixture was diluted with approx. 30 ml of water and saturated with sodium chloride, whereupon the reaction product crystallised out. It was suction filtered and purified by column chromatography (silica gel, eluant:petroleum ether with 10–50% ethyl acetate).

Yield: 71.7% of theory $C_{21}H_{18}N_4OS$ (374.47)

Rf value: 0.69 (silica gel, petroleum ether/ethyl acetate 1:1)

Mass spectrum: $(M+H)^+=375$ 2b) 3-(but-2-ynyl)-2-methylsulphonyl-5-(naphthalen-1-ylmethyl)-3,5-dihydro-imidazo[4,5-d]pyridazin-4-one

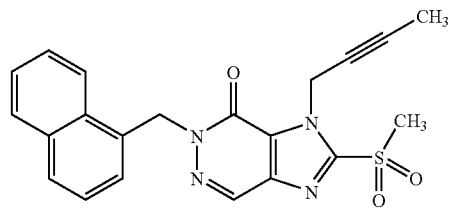

A solution of 500 mg of potassium permanganate in 20 ml of water was added dropwise to a solution of 600 mg (1.60 mmol) of 3-(but-2-ynyl)-2-methylsulphanyl-5-(naphthalen-1-ylmethyl)-3,5-dihydro-imidazo[4,5-d]pyridazin-4-one in 30 ml glacial acetic acid, with stirring, at ambient temperature. After three hours at ambient temperature a sodium hydrogen sulphite solution was added dropwise until the reaction mixture was virtually decolourised again. Then it was diluted with approx. 50 ml of water and saturated with sodium chloride. The crude product precipitated was suction filtered and purified by column chromatography (aluminium oxide; eluant:dichloromethane).

Yield: 43.0% of theory $C_{21}H_{18}N_4O_3S$ (406.47)

Rf value: 0.70 (silica gel, dichloromethane/ethanol 19:1)

Mass spectrum: $(M+H)^+=407$ $^1$H-NMR spectrum ($d_6$-DMSO): δ=1.80 (s, 3H); 3.60 (s, 3H); 5.61 (s, 2H); 5.85 (s, 2H); 7.30 (dd, 1H); 7.45 (t, 1H); 7.58 (m, 2H); 7.90 (dd, 1H); 7.96 (dd, 1H); 8.30 (dd, 1H); 8.64 (s, 1H) ppm.

2c) tert. butyl [1-(1-(but-2-ynyl)-6-naphthalen-1-ylmethyl-7-oxo-6,7-dihydro-1H-imidazo[4,5-d]pyridazin-2-yl)-piperidin-3-yl]-carbaminate

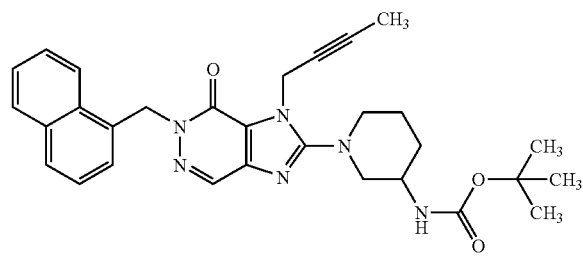

A mixture of 260 mg (0.64 mmol) of 3-(but-2-ynyl)-2-methylsulphonyl-5-(naphthalen-1-ylmethyl)-3,5-dihydro-imidazo[4,5-d]pyridazin-4-one and 800 mg (3.99 mmol) of tert.butyl piperidin-3-yl-carbaminate was stirred for two hours at 150° C. under nitrogen. After cooling it was dissolved in approx. 15 ml dichloromethane, washed with dilute ammonia solution and dried over sodium sulphate. The crude product obtained after the evaporation was purified by column chromatography (silica gel; eluant:dichloromethane with 1–5% ethanol).

Yield: 35.6% of theory
$C_{30}H_{34}N_6O_3$ (526.64)
Rf value: 0.53 (silica gel, dichloromethane/ethanol 19:1)
Mass spectrum: $(M+H)^+=527$ 2d) 2-(3-amino-piperidin-1-yl)-3-(but-2-ynyl)-5-(naphthalen-1-ylmethyl)-3,5-dihydro-imidazo[4,5-d]pyridazin-4-one hydrochloride

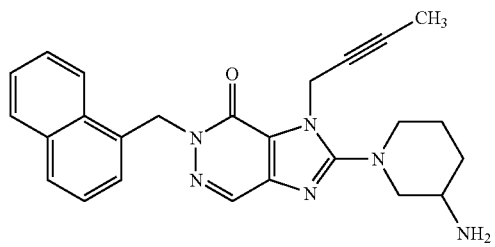

A solution of 120 mg (0.23 mmol) of tert.butyl [1-(1-(but-2-ynyl)-6-naphthalen-1-ylmethyl-7-oxo-6,7-dihydro-1H-imidazo[4,5-d]pyridazin-2-yl)-piperidin-3-yl]-carbaminate and 1.0 ml of trifluoroacetic acid in 10 ml dichloromethane was stirred for three hours at ambient temperature and then evaporated to dryness. The residue was dissolved in 15 ml dichloromethane, the solution was washed with 1N sodium hydroxide solution, dried over sodium sulphate and evaporated down. The crude product thus obtained was purified by column chromatography (silica gel; eluant:dichloromethane with 2–5% ethanol). The product was dissolved in 8 ml of ethyl acetate, and the hydrochloride was precipitated by the dropwise addition of ethereal hydrochloric acid, suction filtered and dried.

Yield: 66.3% of theory
$C_{25}H_{26}N_6O\times HCl$ (462.99)
Rf value: 0.22 (silica gel, dichloromethane/ethanol 9:1)
Mass spectrum: $(M+H)^+=427$
$^1$H-NMR spectrum ($d_6$-DMSO): δ=1.69 (m, 2H); 1.80 (s, 3H); 1.93 (m, 1H); 2.07 (m, 1H); 3.20 (m, 2H); 3.40 (m, 1H); 3.52 (m, 1H); 3.73 (m, 1H); 5.19 (m, 2H); 5.80 (s, 2H); 7.22 (d, 1H); 7.45 (t, 1H); 7.57 (m, 2H); 7.88 (dd, 1H); 7.96 (d, 1H); 8.29 (d, 1H); 8.31 (s, 1H); 8.40 (broad s, 3H) ppm.

EXAMPLE 3

3,5-Dibenzyl-2-(piperazin-1-yl)-3,5-dihydro-imidazo[4,5-c]pyridin-4-one

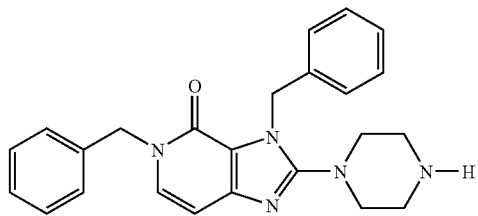

3a) 2,4-dichloro-3-nitropyridine

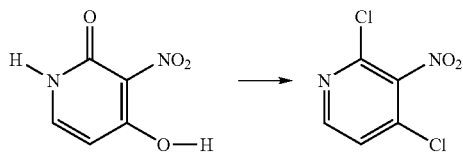

A solution of 30.0 g (0.192 mol) 2,4-dihydroxy-3-nitropyridine in 300 ml of phosphorus oxychloride was refluxed for 50 hours, then approx. 200 ml of phosphorus oxychloride was distilled off and the residue was decomposed with ice water (approx. 300 ml). The dark solution thus obtained was extracted twice with 150 ml of ethyl acetate, the organic phases were washed with saturated sodium chloride solution, dried and evaporated down. The crude product thus obtained was purified by column chromatography (silica gel, eluant:dichloromethane).

Yield: 75% of theory.
Rf value: 0.88 (silica gel, dichloromethane/ethanol=9:1)
Mass spectrum: $M^+=192/4/6$ 3b) 4-amino-2-chloro-3-nitropyridine

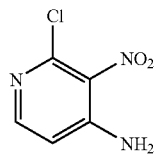

A solution of 28.0 g (0.193 mol) of 2,4-dichloro-3-nitropyridine in 300 ml of ammonia-saturated ethanol was stirred for four days at ambient temperature, then evaporated to dryness and the crude product thus obtained was purified by column chromatography (silica gel, eluant:dichloromethane with 0–5% ethanol).

Yield: 71% of theory.
$C_5H_4ClN_3O_2$ (173.56)
Mass spectrum: $(M+H)^+=174/6$ 3c) 4-amino-2-hydroxy-3-nitropyridine

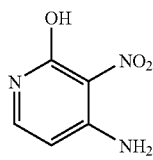

A solution of 18.0 g (104 mmol) of 4-amino-2-chloro-3-nitropyridine in 120 ml dimethylsulphoxide and 30 ml of water was stirred for four hours at 130° C. The solution was then cooled and left to stand overnight while cooling with ice. The product that crystallised out was suction filtered, washed with a little water and dried at 50° C.

Yield: 69% of theory.

$C_5H_5N_3O_3$ (155.11)

Mass spectrum: $(M+H)^+=156$ $(M-H)^-=154$ 3d) 3,4-diamino-2-hydroxypyridine

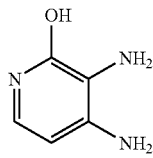

11.0 g (71 mmol) of 4-amino-2-hydroxy-3-nitropyridine were dissolved in 150 ml of dimethylformamide and reduced by catalytic hydrogenation at ambient temperature (Pd/C 10%).

Yield: 83% of theory.

$C_5H_7N_3O$ (125.13)

Mass spectrum: $(M+H)^+=126$ 3e) 2-Mercapto-3,5-dihydro-imidazo[4,5-c]pyridin-4-one

A suspension of 5.0 g (39.96 mmol) of 3,4-diamino-2-hydroxypyridine and 12.82 g (80.0 mmol) of potassium-ethyl xanthogenate in 100 ml of ethanol was refluxed for three hours. The mixture was then cooled to ambient temperature and combined with approx. 20 ml of diethyl ether. The precipitated product was filtered off, washed with approx. 10 ml of diethyl ether, dried, dissolved in approx. 30 ml of water and this solution was acidified with concentrated hydrochloric acid. The product precipitated was suction filtered, washed with 15 ml of water and dried at 50° C.

Yield: 82% of theory.

$C_6H_5N_3OS$ (167.19)

Mass spectrum: $(M+H)^+=168$ $(M-H)^-=166$ 3f) 2-methylmercapto-3,5-dihydro-imidazo[4,5-c]pyridin-4-one

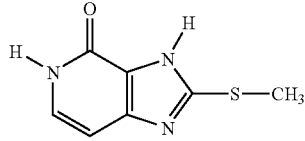

4.38 g (31.7 mmol) of potassium carbonate and 1.97 ml (31.7 mmol) of methyl iodide were added to a suspension of 5.30 g (31.7 mmol) of 2-mercapto-3,5-dihydro-imidazo[4,5-c]pyridin-4-one in 100 ml dichloromethane and 50 ml of methanol and the mixture was stirred overnight at ambient temperature. Then a further 15 ml of methanol were added and undissolved ingredients were filtered off. The filtrate was concentrated by evaporation and the crude product thus obtained was purified by column chromatography (silica gel, eluant:dichloromethane with 5–25% ethanol).

Yield: 96% of theory.

$C_7H_7N_3OS$ (181.22)

Rf value: 0.53 (silica gel, dichloromethane/ethanol 9:1)

Mass spectrum: $(M+H)^+=182$ $^1$H-NMR spectrum ($d_6$-DMSO): δ=2.62 (s, 3H); 6.40 (broad s, 1H); 7.03 (d, 1H); 11.12 (broad s, 1H); 12.95 (broad d, 1H) ppm.

3g) 3,5-dibenzyl-2-methylmercapto-3,5-dihydro-imidazo[4,5-c]pyridin-4-one

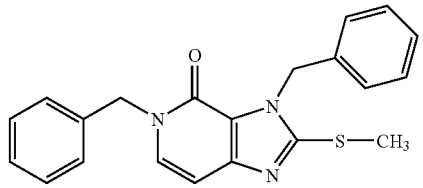

553 mg (4.0 mmol) of potassium carbonate and 0.48 ml (4.0 mmol) of benzyl bromide were added to a solution of 362 mg (2.0 mmol) of 2-methylmercapto-3,5-dihydro-imidazo[4,5-c]pyridin-4-one in 5.0 ml of dimethylformamide and this mixture was stirred for three hours at ambient temperature. Then it was diluted with 10 ml of water and extracted three times with 10 ml of ethyl acetate. The organic extracts were dried and evaporated down, the crude product thus obtained was purified by column chromatography (silica gel, eluant:dichloromethane with 0–3% ethanol).

Yield: 26% of theory.

$C_{21}H_{19}N_3OS$ (361.47)

Rf value: 0.62 (silica gel, dichloromethane/ethanol 19:1)

Mass spectrum: $(M+H)^+=362$ $^1$H-NMR spectrum ($d_6$-DMSO): δ=2.67 (s, 3H); 5.21 (s, 2H); 5.62 (s, 2H); 6.63 (d, 1H); 7.20–7.37 (m, 10 H); 7.56 (d, 1H) ppm.

3h) 3,5-dibenzyl-2-methanesulphonyl-3,5-dihydro-imidazo[4,5-c]pyridin-4-one

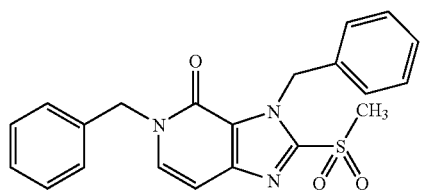

A solution of 190 mg (1.10 mmol) of 3-chloro-peroxybenzoic acid in 5 ml dichloromethane was added dropwise to a solution of 181 mg (0.50 mmol) of 3,5-dibenzyl-2-methylmercapto-3,5-dihydro-imidazo[4,5-c]pyridin-4-one in 10 ml of dichloromethane at ambient temperature with stirring. After the addition had ended the reaction mixture was stirred for a further 30 minutes, then extracted with approx. 25 ml of 5% sodium hydrogen carbonate solution, the organic phase was separated off, dried over sodium sulphate and concentrated by evaporation. The crude product thus obtained, which contained approx. 20% of the methanesulphinyl compound, was further processed without any more purification.

Yield: approx. 75% of theory $C_{21}H_{19}N_3O_3S$ (393.47)

Rf value: 0.66 (silica gel, dichloromethane/ethanol 19:1)

Mass spectrum: $(M+H)^+=394$ 3i) 3,5-Dibenzyl-2-(piperazin-1-yl)-3,5-dihydro-imidazo[4,5-c]pyridin-4-one

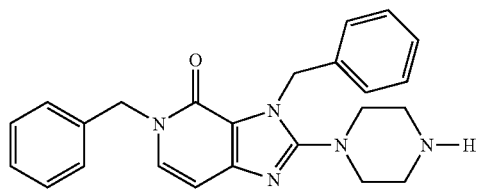

660 mg (11 mmol) of glacial acetic acid were added dropwise to 860 mg (10 mmol) of piperazine with cooling, then 180 mg of 3,5-dibenzyl-2-methanesulphonyl-3,5-dihydro-imidazo[4,5-c]pyridin-4-one (crude product from Example 3 h) were added and the mixture was stirred for 24 hours at 150° C. After cooling approx. 10 ml of water were added, the mixture was made alkaline with concentrated ammonia solution and the mixture was extracted three times with 5 ml of dichloromethane. The extracts were dried over sodium sulphate and concentrated by evaporation. The crude product thus obtained was purified by column chromatography (silica gel; eluant:petroleum ether with 20–60% ethyl acetate).

Yield: 5.5% of theory $C_{24}H_{25}N_5O$ (399.50)

Rf value: 0.28 (silica gel, petroleum ether/ethyl acetate 7:3)

Mass spectrum: $(M+H)^+=400$

EXAMPLE 4

2-(3-amino-piperidin-1-yl)-5-benzyl-3-(but-2-ynyl)-3,5-dihydro-imidazo[4,5-c]pyridin-4-one

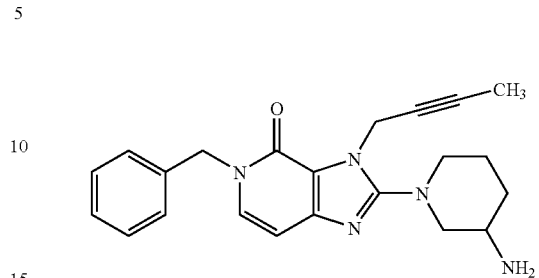

4a) 1-benzyl-4-benzyloxy-3-nitro-pyridin-2-one

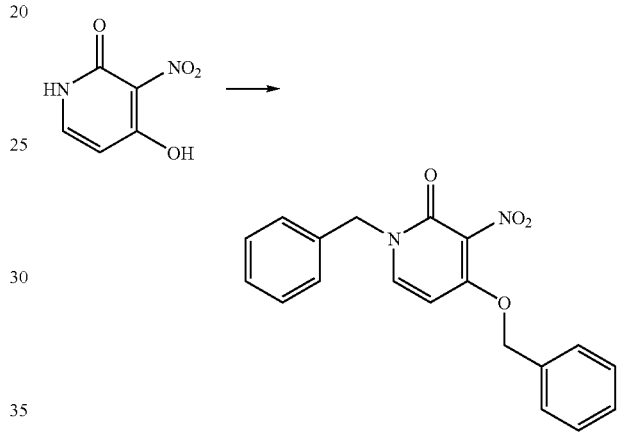

A solution of 4.68 g (30 mmol) of 2,4-dihydroxy-3-nitropyridine in 100 ml of dimethylformamide was combined batchwise at ambient temperature with 2.88 g (60 mmol) of a 50% suspension of sodium hydride in paraffin oil and stirred for 15 minutes. Then 8.91 ml (75 mmol) of benzylbromide were added and the mixture was stirred for 24 hours at 80° C. The solution was then carefully stirred into approx. 250 ml of water and extracted three times with 70 ml of ethyl acetate. The extracts were washed with saturated sodium chloride solution, dried and evaporated down in vacuo. The residue was triturated with diethyl ether, suction filtered and dried. The product thus obtained was further processed without any purification.

Yield: 59% of theory.

$C_{19}H_{16}N_2O_4$ (336.35)

Mass spectrum: $(M+H)^+=337$ 4b) 4-amino-1-benzyl-3-nitro-pyridin-2-one

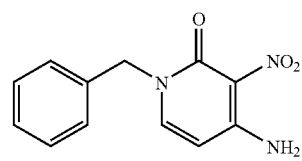

20 ml of a saturated ethanolic ammonia solution were added to a solution of 5.5 g (16.3 mmol) of 1-benzyl-4-benzyloxy-3-nitro-pyridin-2-one in 50 ml dichloromethane and stirred for 3 days at ambient temperature in the sealed flask. The solution was evaporated to dryness, the residue was triturated with diethyl ether, suction filtered and dried.

Yield: 97% of theory.
$C_{12}H_{11}N_3O_3$ (245.24)
Rf value: 0.31 (silica gel; dichloromethane/ethanol 19:1)

4c) 1-benzyl-3,4-diamino-pyridin-2-one

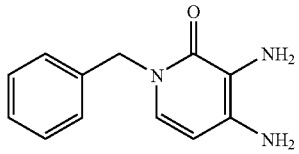

3.9 g (15.9 mmol) of 4-amino-1-benzyl-3-nitro-pyridin-2-one, dissolved in 250 ml of tetrahydrofuran, were hydrogenated over platinum oxide at 50 psi of $H_2$ pressure and at ambient temperature. After the catalyst had been filtered off the filtrate was concentrated by evaporation and the residue was further processed in crude form.

Yield: 99% of theory.
$C_{12}H_{13}N_3O$ (215.26)

4d) 5-benzyl-2-mercapto-3,5-dihydro-imidazo[4,5-c]pyridin-4-one

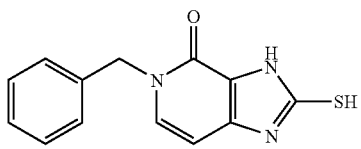

A solution of 3.40 g (15.8 mmol) of 1-benzyl-3,4-diamino-pyridin-2-one and 4.99 g (28.0 mmol) of N,N'-thiocarbonyl-diimidazole in 200 ml of tetrahydrofuran was stirred overnight at ambient temperature, then concentrated by evaporation, the residue was combined with approx. 50 ml of water, adjusted to pH 7 with 2N hydrochloric acid and this solution was stirred for approx. 30 minutes at ambient temperature. The product precipitated was suction filtered, washed with approx. 50 ml of water and dried at 50° C.

Yield: 98% of theory.
$C_{13}H_{11}N_3OS$ (257.32)
Rf value: 0.45 (silica gel; dichloromethane/ethanol 9:1)

4e) 5-benzyl-2-methylsulphanyl-3,5-dihydro-imidazo[4,5-c]pyridin-4-one

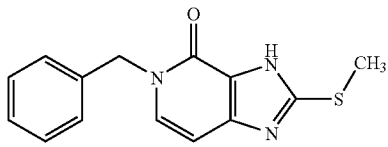

4.0 g (15.55 mmol) of 5-benzyl-2-mercapto-3,5-dihydro-imidazo[4,5-c]pyridin-4-one were suspended in a mixture of 100 ml of dichloromethane and 50 ml of methanol, then 2.15 g (15.55 mmol) of potassium carbonate and 0.97 ml (15.55 mmol) of iodomethane were added and the mixture was stirred for 1 hour at ambient temperature. Then it was filtered, the filtrate was evaporated down and the residue was further reacted in its crude form.

Yield: 94% of theory.
$C_{14}H_{13}N_3OS$ (271.34)
Rf value: 0.49 (silica gel; dichloromethane/ethanol 9:1)
Mass spectrum: $(M+H)^{30}$ =272

4f) 5-benzyl-3-(but-2-ynyl)-2-methylsulphanyl-3,5-dihydro-imidazo[4,5-c]pyridin-4-one

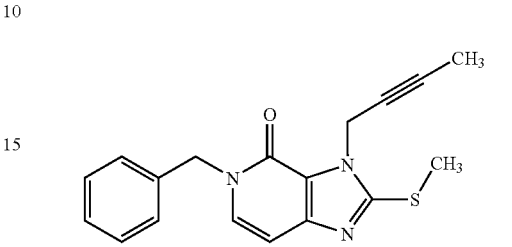

2.07 g (15.0 mmol) of potassium carbonate were added to a solution of 4.0 g (14.7 mmol) of 5-benzyl-2-methylsulphanyl-3,5-dihydro-imidazo[4,5-c]pyridin-4-one and 1.31 ml (15.0 mmol) of 1-bromo-2-butyne in 100 ml of dimethylformamide and stirred for one hour at ambient temperature. Then approx. 200 ml of saturated sodium chloride solution were added and the mixture was extracted three times with 50 ml of ethyl acetate. The extracts were washed with saturated sodium chloride solution, dried over sodium sulphate and evaporated down. The crude product thus obtained was purified by column chromatography (silica gel; eluant:dichloromethane with 0–2% ethanol).

Yield: 48% of theory.
$C_{18}H_{17}N_3OS$ (323.42)
Rf value: 0.71 (silica gel; dichloromethane/ethanol 9:1)
$^1$H-NMR spectrum ($d_6$-DMSO): δ=1.78 (s, 3H); 2.70 (s, 3H); 5.18 (s, 2H); 5.23 (s, 2H); 6.61 (d, 1H); 7.23–7.38 (m, 5H); 7.53 (d, 1H) ppm.
Mass spectrum: $(M+H)^+$=324

4g) 5-benzyl-3-(but-2-ynyl)-2-methylsulphonyl-3,5-dihydro-imidazo[4,5-c]pyridin-4-one

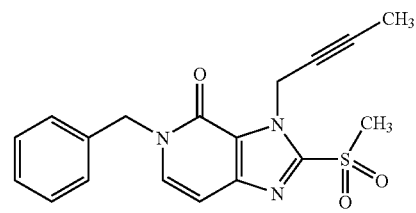

A solution of 316 mg (2.0 mmol) of potassium permanganate in 10 ml of water was slowly added dropwise with stirring to a solution of 400 mg (1.24 mmol) of 5-benzyl-3-(but-2-ynyl)-2-methylsulphanyl-3,5-dihydro-imidazo[4,5-c]pyridin-4-one in 10 ml of concentrated acetic acid. After three hours at ambient temperature 400 mg of sodium bisulphite ($Na_2S_2O_5$) were added and the mixture was diluted with approx. 30 ml of water. It was extracted five times with 30 ml of dichloromethane, the extracts were dried over sodium sulphate and evaporated down. The product thus obtained was further reacted without purification.

Yield: 50% of theory.
$C_{18}H_{17}N_3O_3S$ (355.42)
Rf value: 0.40 (silica gel; dichloromethane/ethanol 19:1)
Mass spectrum: $(M+H)^+$=356

4h) tert-butyl [1-(5-benzyl-3-(but-2-ynyl)-4-oxo-4,5-dihydro-3H-imidazo[4,5-c]pyridin-2-yl)-piperidin-3-yl]-carbaminate

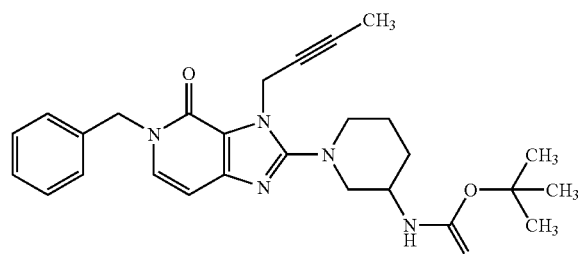

A mixture of 220 mg (0.62 mmol) of 5-benzyl-3-(but-2-ynyl)-2-methylsulphonyl-3,5-dihydro-imidazo[4,5-c]pyridin-4-one and 781.1 mg (3.90 mmol) of tert-butyl piperidin-3-yl-carbaminate was heated to 170° C. under nitrogen for 5 hours. After cooling to ambient temperature the crude product thus obtained was purified by column chromatography (silica gel; eluant:dichloromethane with 0–3% ethanol).

Yield: 23% of theory
$C_{27}H_{33}N_5O_3$ (475.60)
Rf value: 0.32 (silica gel; dichloromethane/ethanol 19:1)
Mass spectrum: $M^+=475$ $(M+H)^+=476$ 4i) 2-(3-amino-piperidin-1-yl)-5-benzyl-3-(but-2-ynyl)-3,5-dihydro-imidazo[4,5-c]pyridin-4-one

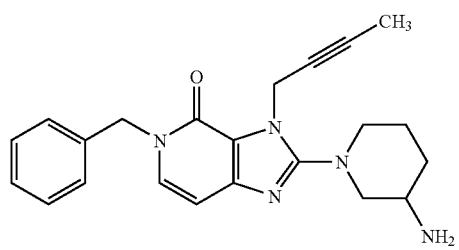

A solution of 70.0 mg (0.147 mmol) of tert-butyl [1-(5-benzyl-3-(but-2-ynyl)-4-oxo-4,5-dihydro-3H-imidazo[4,5-c]pyridin-2-yl)-piperidin-3-yl]-carbaminate and 0.5 ml trifluoroacetic acid in 3.0 ml dichloromethane was stirred for one hour at ambient temperature. The mixture was then concentrated by evaporation in vacuo and the residue was dissolved in approx. 5 ml dichloromethane. This solution was washed with approx. 5 ml of 1N sodium hydroxide solution, then dried over sodium sulphate and concentrated by evaporation. The residue was dissolved in approx. 3 ml of ethyl acetate, and the product was precipitated as the hydrochloride by the dropwise addition of ethereal hydrochloric acid, suction filtered and dried.

Yield: 41% of theory.
$C_{22}H_{25}N_5O \times HCl$ (411.94)
Rf value: 0.22 (silica gel; dichloromethane/ethanol 9:1)
Mass spectrum: $M^+=375$ $(M+H)^+=376$

EXAMPLE 6

2-((R)-3-amino-piperidin-1-yl)-3-(but-2-ynyl)-5-{[1,2,4]triazolo[4,3-a]pyridin-3-ylmethyl}-3,5-dihydro-imidazo[4,5-d]pyridazin-4-one hydrochloride

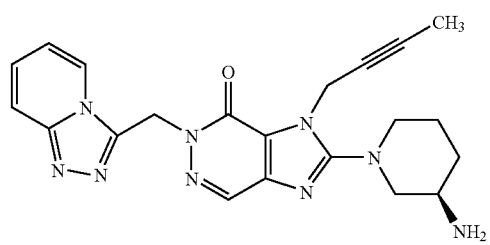

Prepared analogously to Example 1j by cleaving the Boc protective group with trifluoroacetic acid in dichloromethane.

Yield: 72% of theory.
$C_{21}H_{23}N_9O$ (417.48)
Mass spectrum: $(M+H)^+=418$
$^1$H-NMR spectrum ($d_6$-DMSO): δ=1.70 (m, 2H); 1.80 (s, 3H); 1.93 (m, 1H); 2.02 (m, 1H); 3.20 (m, 2H); 3.38 (m, 1H); 3.50 (m, 1H); 3.74 (m, 1H); 5.17 (m, 2H); 5.98 (s, 2H); 7.45 (t, 1H); 7.90 (dd, 1H); 8.02 (d, 1H); 8.33 (s, 1H); 8.50 (broad s, 3H); 8.98 (d, 1H) ppm.

EXAMPLE 7

2-(3-amino-piperidin-1-yl)-3-(but-2-ynyl)-5-(3-methyl-isoquinolin-1-ylmethyl)-3,5-dihydro-imidazo[4,5-d]pyridazin-4-one

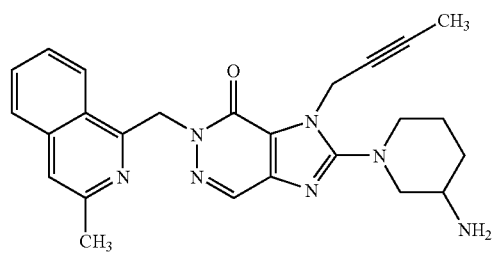

Prepared analogously to Example 1j from tert-butyl {1-[1-(but-2-ynyl)-6-(3-methyl-isoquinolin-1-ylmethyl)-7-oxo-6,7-dihydro-1H-imidazo[4,5-d]pyridazin-2-yl]-piperidin-3-yl}-carbaminate and trifluoroacetic acid in dichloromethane.

Yield: 57% of theory.
$C_{25}H_{27}N_7O \times HCl$ (477.99)
Rf value: 0.13 (silica gel; dichloromethane/ethanol 9:1)
Mass spectrum: $(M+H)^+=442$

EXAMPLE 35

2-(3-amino-piperidin-1-yl)-3-(but-2-ynyl)-5-(naphthalen-1-ylmethyl)-3,5-dihydro-imidazo[4,5-c]pyridin-4-one

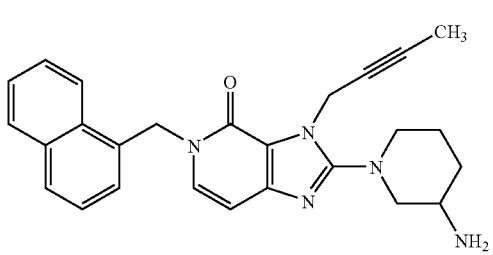

Prepared analogously to Example 1j by cleaving the Boc protective group with trifluoroacetic acid in dichloromethane.

Yield: 92% of theory.

$C_{26}H_{27}N_5O$ (425.54)

Mass spectrum: $(M+H)^+=426$

Rf value: 0.54 (silica gel; dichloromethane/methanol/conc. ammonia 8:2:0.1)

EXAMPLE 86

2-(3-amino-piperidin-1-yl)-3-(3-methyl-but-2-enyl)-5-(3-methyl-isoquinolin-1-ylmethyl)-3,5-dihydro-imidazo[4,5-c]pyridin-4-one

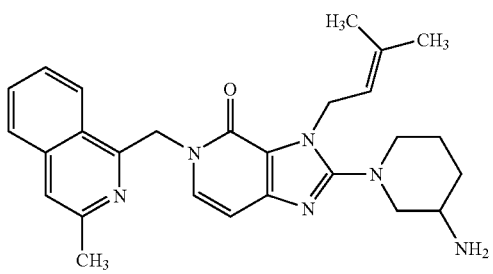

Prepared analogously to Example 1j by cleaving the Boc protective group with trifluoroacetic acid in dichloromethane.

Yield: 84% of theory.

$C_{27}H_{32}N_6O$ (456.59)

Mass spectrum: $(M+H)^+=457$ $^1$H-NMR spectrum ($d_6$-DMSO): δ=1.11–1.25 (m, 1H); 1.57–1.90 (m, 9H); 2.50–2.65 (m, 1H); 2.75–2.88 (m, 2H); 3.25–3.45 (m, 2H); 4.81 (d, 2H); 5.33 (t, 1H); 5.78 (s, 2H); 6,48 (d, 1H); 7.40 (d, 1H); 7.58–7.65 (m, 2H); 7.72 (t, 1H); 7.89 (d, 1H); 8.40 (d, 1H) ppm.

EXAMPLE 136

2-((R)-3-amino-piperidin-1-yl)-3-(but-2-ynyl)-5-(4-methyl-quinazolin-2-ylmethyl)-3,5-dihydro-imidazo[4,5-d]pyridazin-4-one

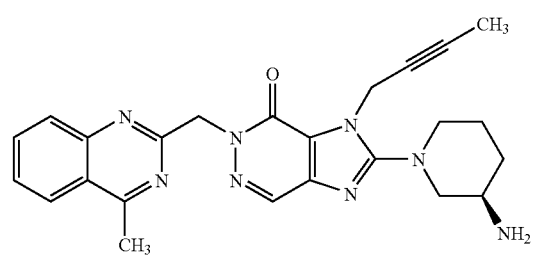

136a) dimethyl 2-bromo-1-(but-2-ynyl)-1H-imidazol-4,5-dicarboxylate

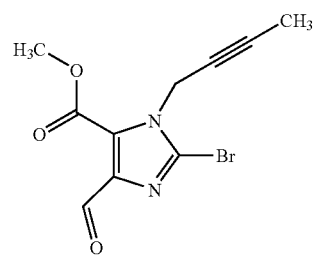

A solution of 15.0 g (57.0 mmol) of dimethyl 2-bromo-imidazole-4,5-dicarboxylate, 5.15 ml (57.0 mmol) of 1-bromo-2-butyne and 50 ml of N,N-diisopropylethylamine in 280 ml of tetrahydrofuran was refluxed for one hour. The mixture was concentrated by evaporation, the residue combined with approx. 100 ml of water and extracted three times with 70 ml of ethyl acetate. The extracts were washed with 50 ml of water, dried and evaporated down. The crude product thus obtained was purified by column chromatography (silica gel; eluant:dichloromethane with 0–2% ethanol).

Yield: 75% of theory.

$C_{11}H_{11}BrN_2O_4$ (315.13)

Rf value: 0.82 (silica gel; dichloromethane/ethanol 9:1)

Mass spectrum: $(M+H)^+=315/317$ 136b) methyl 2-bromo-3-(but-2-ynyl)-5-formyl-3H-imidazol-4-carboxylate 43 ml (43 mmol) of a 1 molar solution of diisobutyl-aluminium hydride in tetrahydrofuran within 20 minutes were added dropwise to a solution of 13.5 g (42.84 mmol) of dimethyl 2-bromo-1-(but-2-ynyl)-1H-imidazol-4,5-dicarboxylate in 220 ml of tetrahydrofuran under an argon atmosphere at −70° C. The mixture was stirred for a further 4 hours at −70° C., then 20 ml of a mixture of 1M hydrochloric acid and tetrahydrofuran were added dropwise. After heating to ambient temperature approx. 200 ml of water were added and the mixture was extracted three times with 70 ml of ethyl acetate. The extracts were dried and evaporated down, and the crude product thus obtained was purified by column chromatography (silica gel; eluant:petroleum ether with 20–50% ethyl acetate).

Yield: 52% of theory.

$C_{10}H_9BrN_2O_3$ (285.10)

Mass spectrum: $(M+H)^+=285/287$ $^1$H-NMR spectrum ($d_6$-DMSO): δ=1.80 (s, 3H); 3.93 (s, 3H); 5.11 (s, 2H); 10.12 (s, 1H) ppm.

136c) 2-bromo-3-(but-2-ynyl)-3,5-dihydro-imidazo[4,5-d]pyridazin-4-one

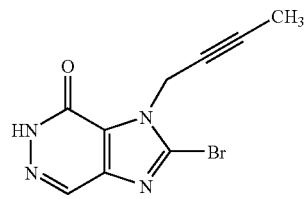

0.31 ml of hydrazine hydrate (99%, 6.31 mmol), dissolved in 1 ml of ethanol, were added dropwise at ambient temperature to a solution of 1.80 g (6.31 mmol) of methyl 2-bromo-3-(but-2-ynyl)-5-formyl-3H-imidazol-4-carboxylate in 25 ml of ethanol. Five minutes later, 1.5 ml of concentrated acetic acid were added and the mixture was refluxed for 30 minutes. After cooling the precipitated solid was suction filtered, washed with 10 ml of ethanol and 20 ml of diethyl ether and dried.

Yield: 74% of theory.

$C_9H_7BrN_4O$ (267.09)

Mass spectrum: $(M+H)^+=267/269$ $^1$H-NMR spectrum ($d_6$-DMSO): δ=1.80 (s, 3H); 5.28 (s, 2H); 8.38 (s, 1H); 12.99 (s, 1H) ppm.

136d) 2-bromo-3-(but-2-ynyl)-5-(4-methyl-quinazolin-2-ylmethyl)-3,5-dihydro-imidazo[4,5-d]pyridazin-4-one

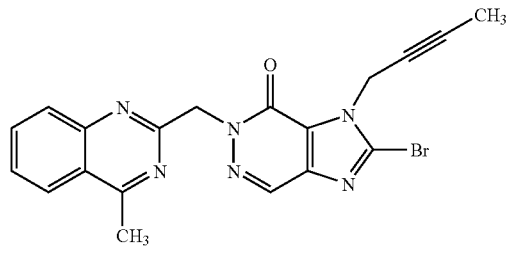

489 mg (1.5 mmol) of caesium carbonate were added to a solution of 300 mg (1.12 mmol) of 2-bromo-3-(but-2-ynyl)-3,5-dihydro-imidazo[4,5-d]pyridazin-4-one and 260.1 mg (1.35 mmol) of 2-chloromethyl-4-methyl-quinazoline in 4.0 ml of dimethylformamide and this mixture was stirred for 2 hours under an argon atmosphere at 80° C. Then it was diluted with 10 ml of water and stirred for 30 minutes at ambient temperature. The crude product precipitated was suction filtered and purified by column chromatography (silica gel; eluant:petroleum ether with 20–50% ethyl acetate).

Yield: 51% of theory.

$C_{19}H_{15}BrN_6O$ (423.28)

136e) tert-butyl {1-[1-(but-2-ynyl)-6-(4-methyl-quinazolin-2-ylmethyl)-7-oxo-6,7-dihydro-1H-imidazo[4,5-d]pyridazin-2-yl]-piperidin-3-yl}-carbaminate

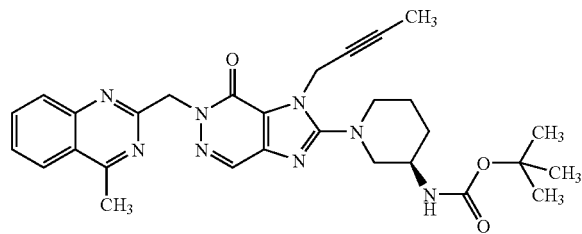

A solution of 240 mg (0.567 mmol) of 2-bromo-3-(but-2-ynyl)-5-(4-methyl-quinazolin-2-ylmethyl)-3,5-dihydro-imidazo[4,5-d]pyridazin-4-one and 140.2 mg (0.70 mmol) of tert-butyl (R)-piperidin-3-yl-carbaminate in 4 ml dimethylsulphoxide was combined with 95 mg (0.9 mmol) of sodium carbonate and stirred for 3 hours at 80° C. Then another 50 mg of tert-butyl piperidin-3-yl-carbaminate were added and the mixture was stirred for a further 2 hours at 80° C. After cooling to ambient temperature it was combined with 10 ml of water and stirred for 30 minutes. The product precipitated was suction filtered, washed with 5 ml of water and dried.

Yield: 81% of theory.

$C_{29}H_{34}N_8O_3$ (542.65)

136f) 2-((R)-3-amino-piperidin-1-yl)-3-(but-2-ynyl)-5-(4-methyl-quinazolin-2-ylmethyl)-3,5-dihydro-imidazo[4,5-d]pyridazin-4-one

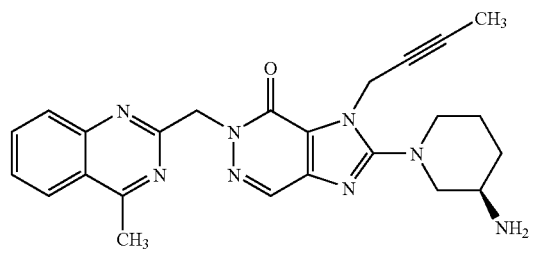

Prepared analogously to 1j from 240 mg (0.442 mmol) of tert-butyl {1-[1-(but-2-ynyl)-6-(4-methyl-quinazolin-2-ylmethyl)-7-oxo-6,7-dihydro-1H-imidazo[4,5-d]pyridazin-2-yl]-piperidin-3-yl}-carbaminate with trifluoroacetic acid in dichloromethane.

Yield: 56% of theory.

$C_{24}H_{26}N_8O$ (442.53)

Rf value: 0.42 (silica gel; dichloromethane/ethanol 9:1 with the addition of 1 drop of conc. ammonia solution)

Mass spectrum: (M+H)$^+$=443

$^1$H-NMR spectrum (d$_6$-DMSO): δ=1.23–1.37 (m, 1H); 1.60–1.95 (m, 6H); 2.75–3.10 (m, 6H); 3.58–3.72 (m, 2H); 5.10 (s, 2H); 5.61 (s, 2H); 7.70 (t, 1H); 7.93 (t, 1H); 8.28 (d, 1H); 8.30 (s, 1H); ppm (exchangeable protons not visible).

EXAMPLE 138

2-((R)-3-amino-piperidin-1-yl)-3-(but-2-ynyl)-5-(benzo[d]isothiazol-3-ylmethyl)-3,5-dihydro-imidazo[4,5-d]pyridazin-4-one

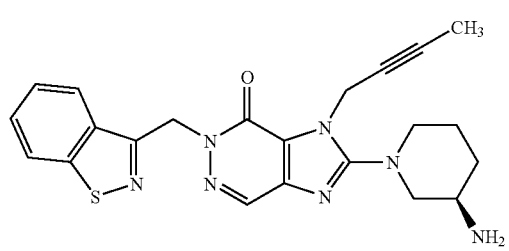

Prepared analogously to Example 1j by cleaving the Boc protective group with trifluoroacetic acid in dichloromethane.

Yield: 83% of theory.

C$_{22}$H$_{23}$N$_7$OS (433.54)

Mass spectrum: (M+H)$^+$=434

Rf value: 0.15 (silica gel; dichloromethane/methanol 9:1)

EXAMPLE 139

2-((R)-3-amino-piperidin-1-yl)-3-(but-2-ynyl)-5-(benzo[d]isoxazol-3-ylmethyl)-3,5-dihydro-imidazo[4,5-d]pyridazin-4-one

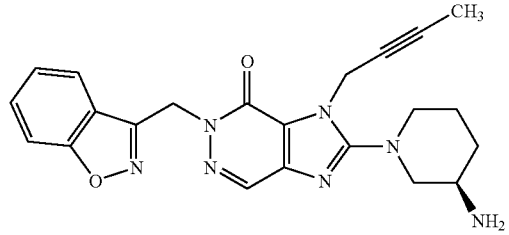

Prepared analogously to Example 1j by cleaving the Boc protective group with trifluoroacetic acid in dichloromethane.

Yield: 67% of theory.

C$_{22}$H$_{23}$N$_7$O$_2$ (417.47)

Mass spectrum: (M+H)$^+$=418

Rf value: 0.40 (silica gel; dichloromethane/methanol/conc. ammonia 9:1:0.1)

EXAMPLE 140

2-((R)-3-amino-piperidin-1-yl)-3-(but-2-ynyl)-5-(1-methyl-1H-indazol-3-ylmethyl)-3,5-dihydro-imidazo[4,5-d]pyridazin-4-one

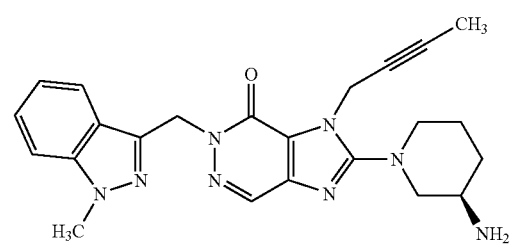

Prepared analogously to Example 1j by cleaving the Boc protective group with trifluoroacetic acid in dichloromethane.

Yield: 90% of theory.

C$_{23}$H$_{26}$N$_8$O (430.52)

Mass spectrum: (M+H)$^+$=431

Rf value: 0.15 (silica gel; dichloromethane/methanol 9:1)

EXAMPLE 178

2-(3-amino-piperidin-1-yl)-3-(but-2-ynyl)-5-(2-oxo-2-phenyl-ethyl)-3,5-dihydro-imidazo[4,5-d]pyridazin-4-one

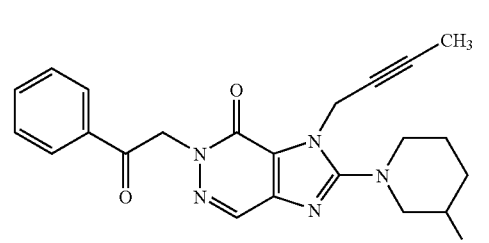

Prepared analogously to Example 1j by cleaving the Boc protective group with trifluoroacetic acid in dichloromethane.

Yield: 79% of theory.

C$_{23}$H$_{28}$N$_6$O$_2$ (420.51)

Mass spectrum: (M+H)$^+$=421

$^1$H-NMR spectrum (d$_6$-DMSO): δ=1.16–1.27 (m, 1H); 1.60–1.95 (m, 9H); 2.65 (dd, 1H); 2.88 (m, 2H); 3.35–3.54 (m, 2H); 4.87 (d, 2H); 5.33 (t, 1H); 5.70 (s, 2H); 7.60 (t, 2H); 7.72 (t, 1H); 8.07 (d, 2H); 8.30 (s, 1H) ppm.

The following compounds may be prepared analogously to the foregoing Examples and other methods known from the literature:

| Ex. | Structure | Ex. | Structure |
|---|---|---|---|
| (1) | 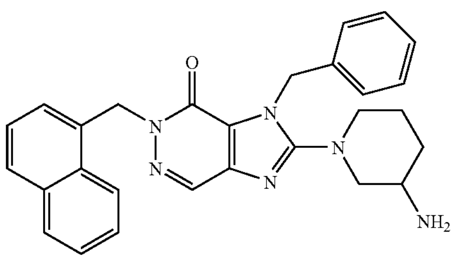 | (2) | 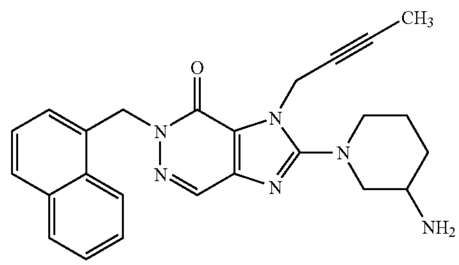 |
| (3) | 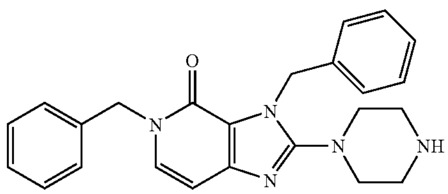 | (4) | 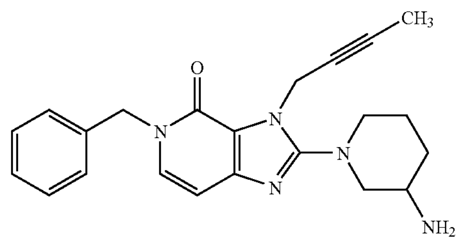 |
| (5) | 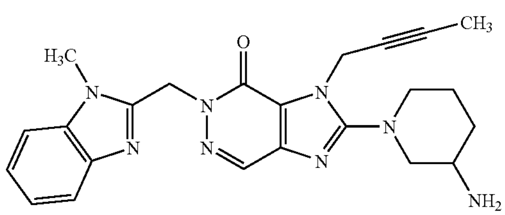 | (6) | 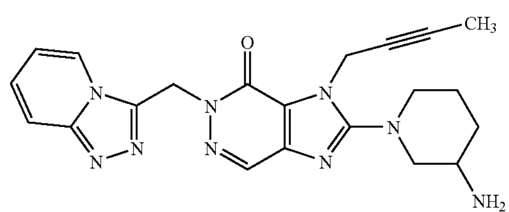 |
| (7) | 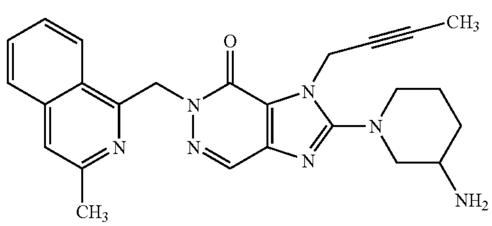 | (8) | 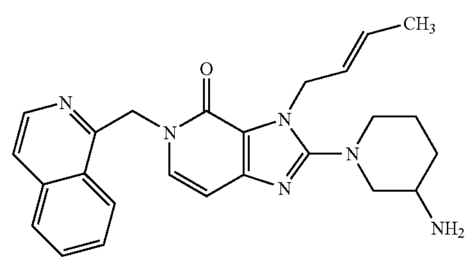 |
| (9) | 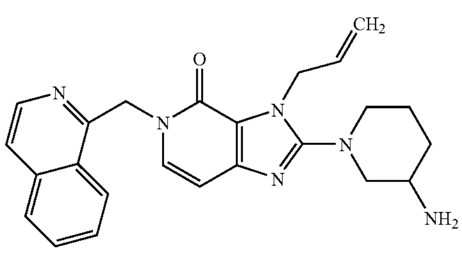 | (10) | 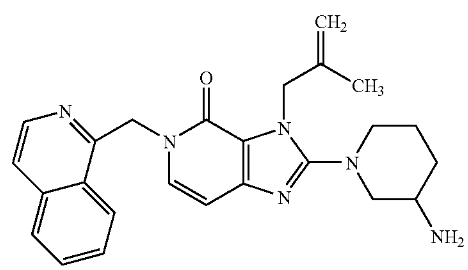 |
| (11) | 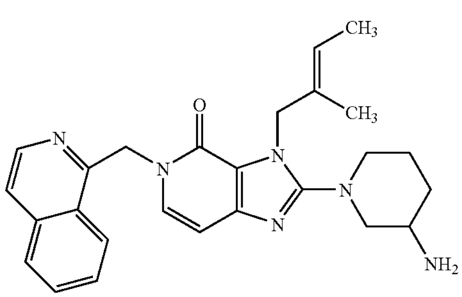 | (12) | 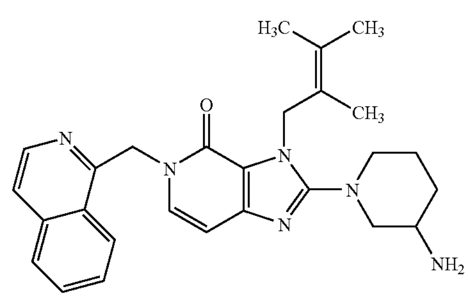 |

-continued
| Ex. | Structure | Ex. | Structure |
|---|---|---|---|
| (13) | 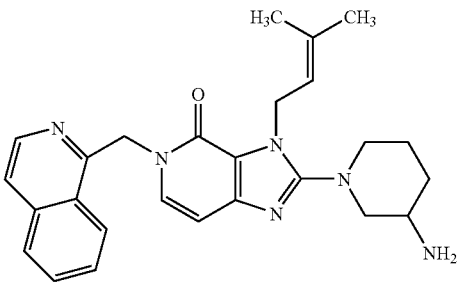 | (14) | 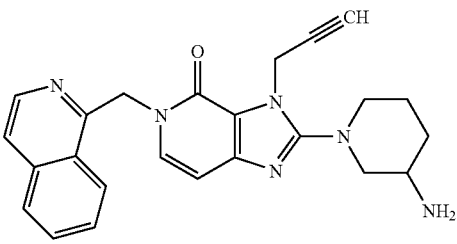 |
| (15) | 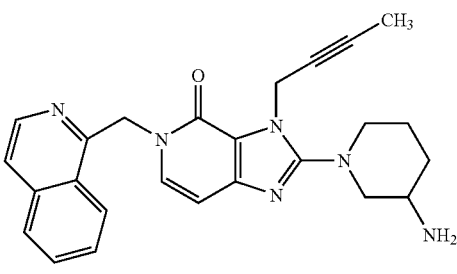 | (16) | 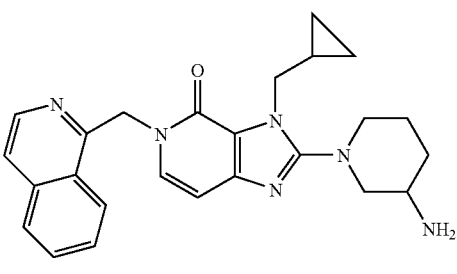 |
| (17) | 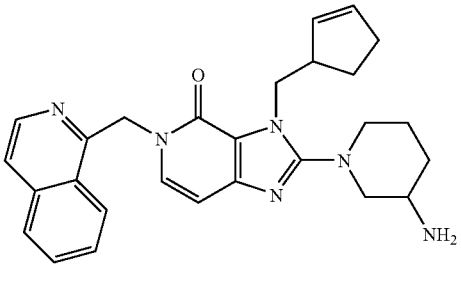 | (18) | 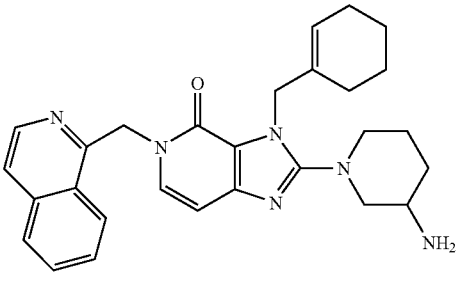 |
| (19) | 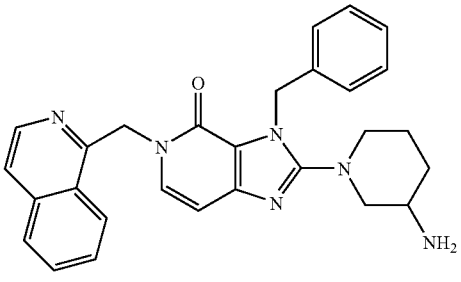 | (20) | 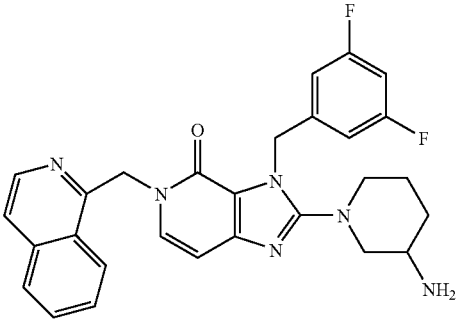 |
| (21) | 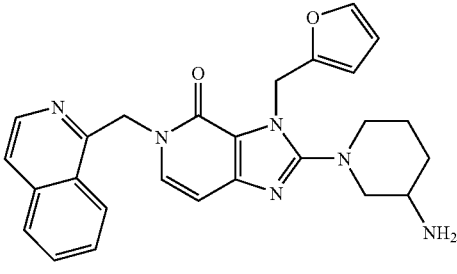 | (22) | 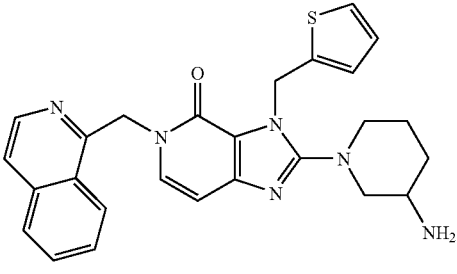 |

-continued
| Ex. | Structure | Ex. | Structure |
|---|---|---|---|
| (23) | 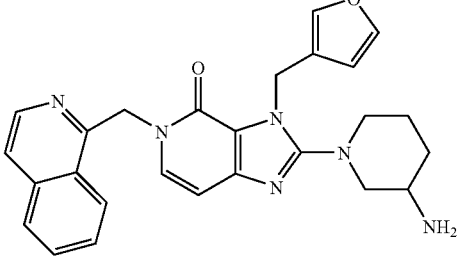 | (24) | 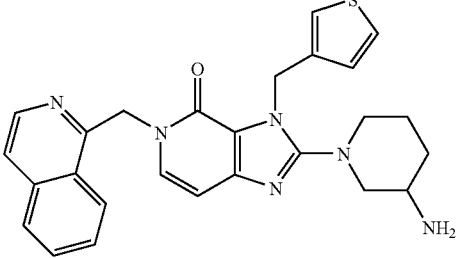 |
| (25) | 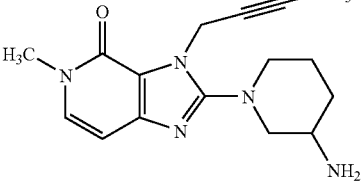 | (26) | 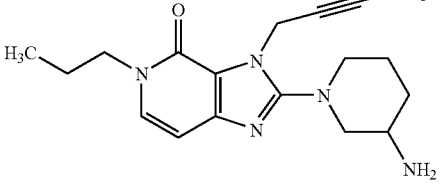 |
| (27) | 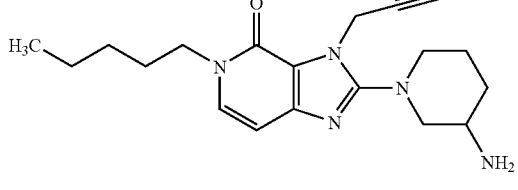 | (28) | 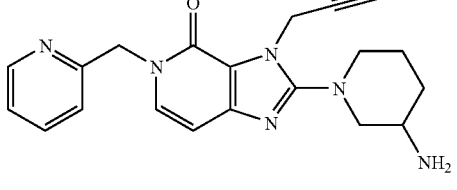 |
| (29) | 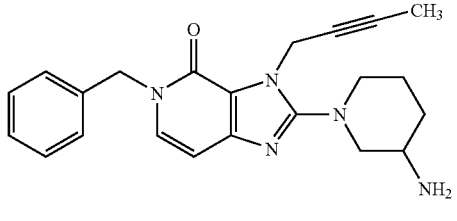 | (30) | 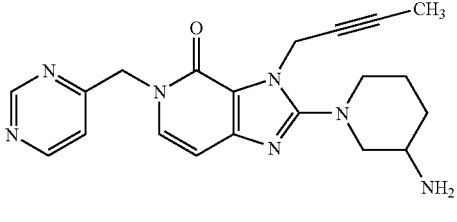 |
| (31) | 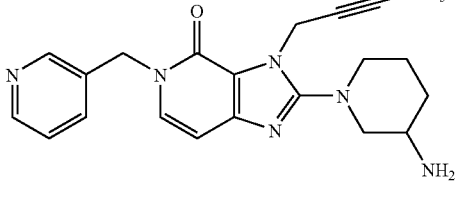 | (32) | 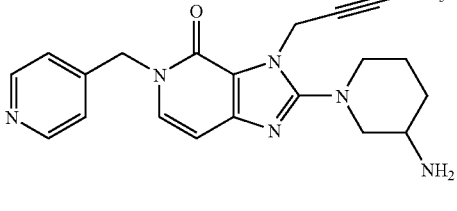 |
| (33) | 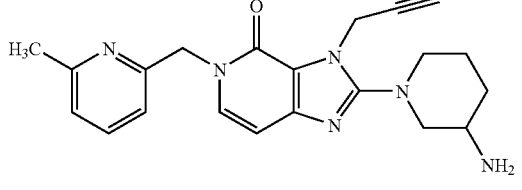 | (34) | 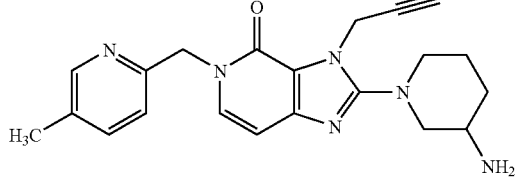 |

-continued

| Ex. | Structure | Ex. | Structure |
|---|---|---|---|
| (35) | 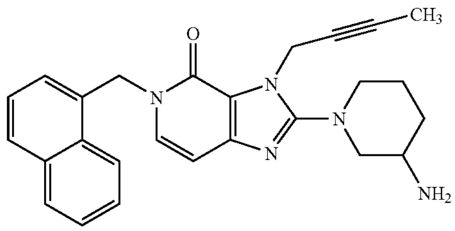 | (36) | 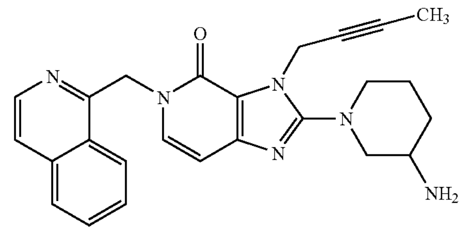 |
| (37) | 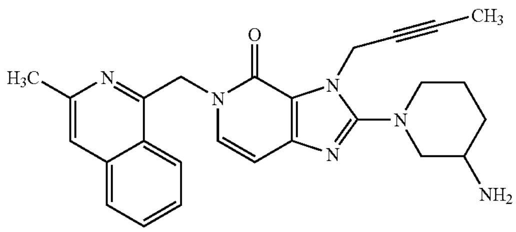 | (38) | 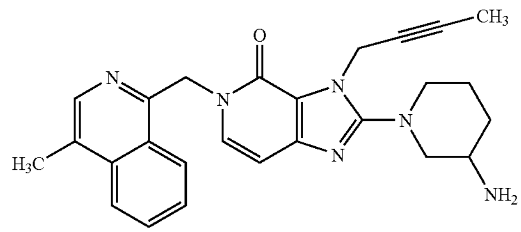 |
| (39) | 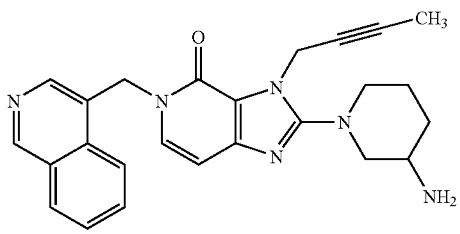 | (40) | 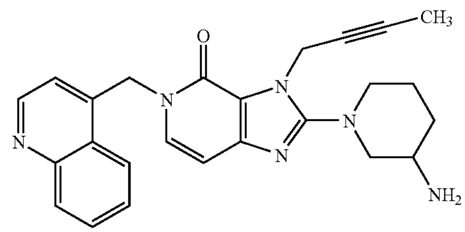 |
| (41) | 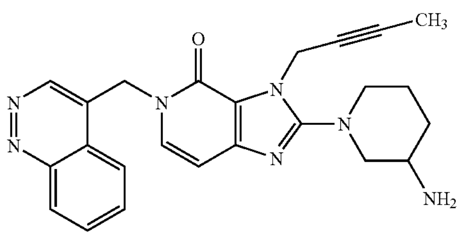 | (42) | 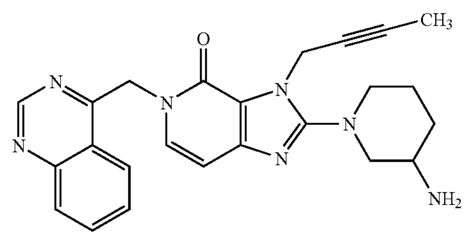 |
| (43) | 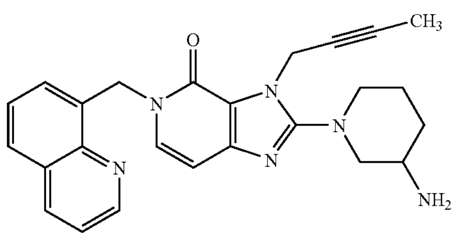 | (44) | 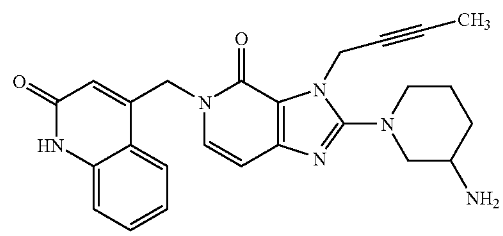 |
| (45) | 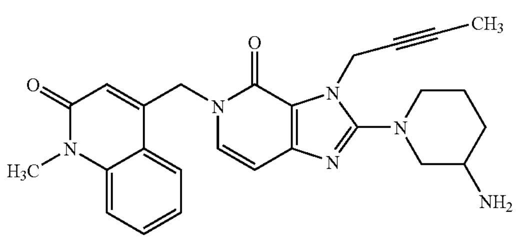 | (46) | 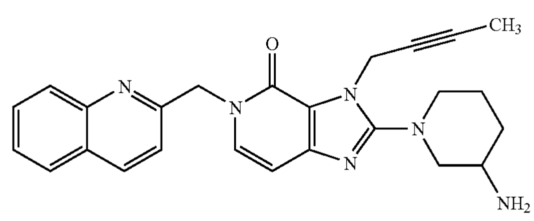 |

-continued

| Ex. | Structure | Ex. | Structure |
|---|---|---|---|
| (47) | 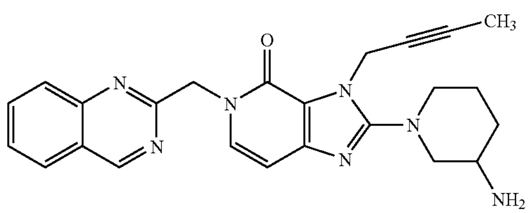 | (48) | 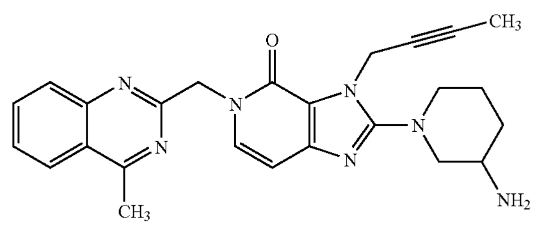 |
| (49) | 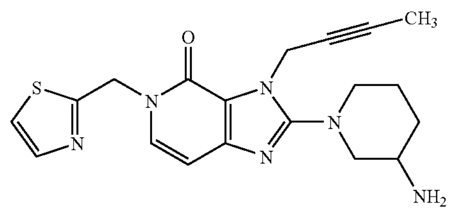 | (50) | 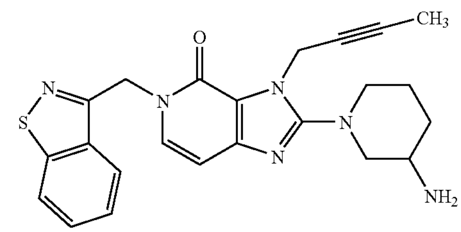 |
| (51) | 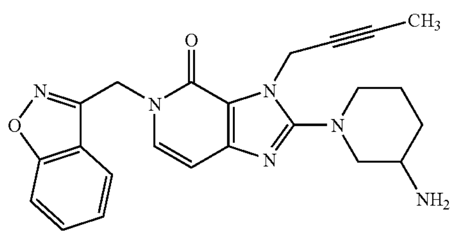 | (52) | 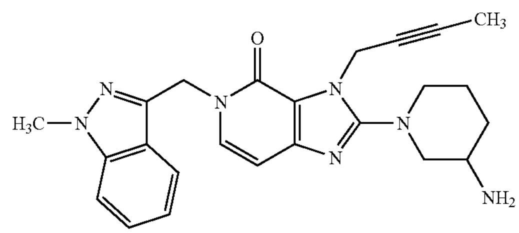 |
| (53) | 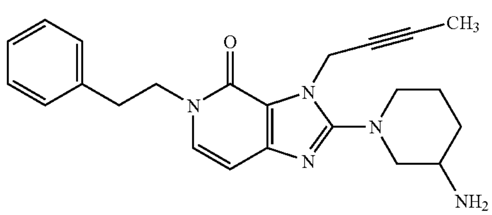 | (54) | 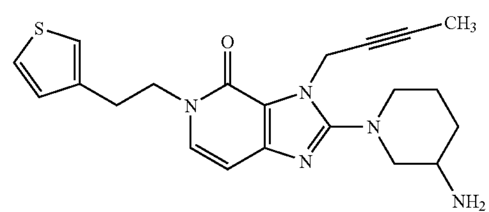 |
| (55) | 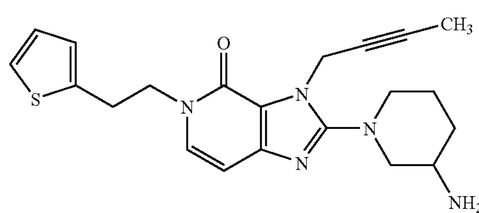 | (56) | 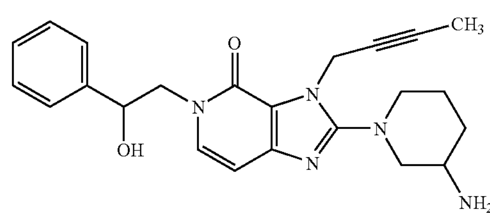 |
| (57) | 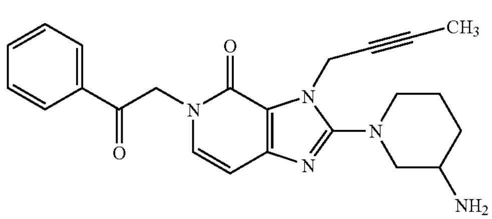 | (58) | 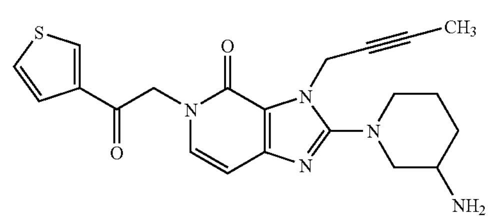 |

-continued

| Ex. | Structure | Ex. | Structure |
|-----|-----------|-----|-----------|
| (59) | 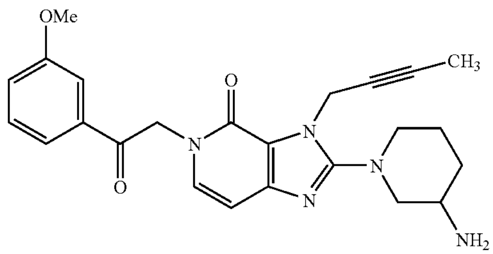 | (60) | 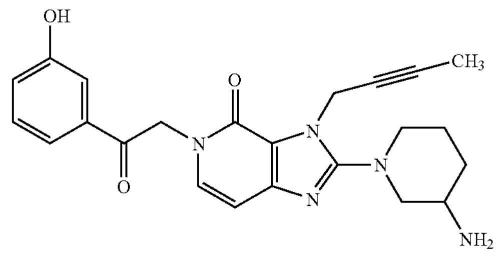 |
| (61) | 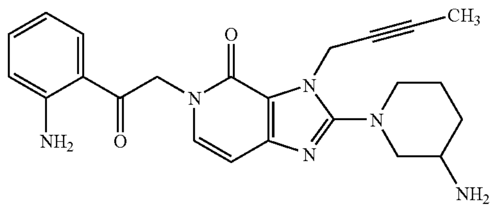 | (62) | 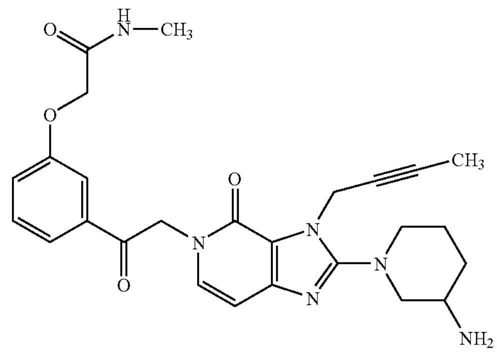 |
| (63) | 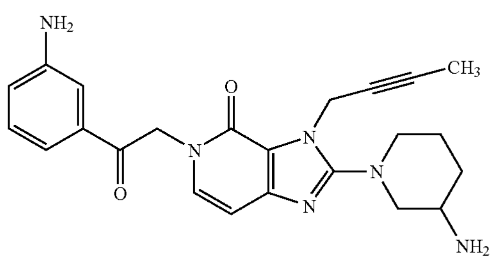 | (64) | 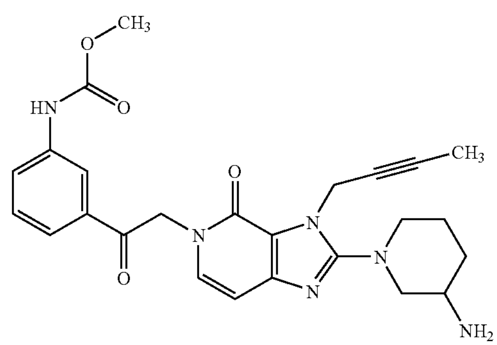 |
| (65) | 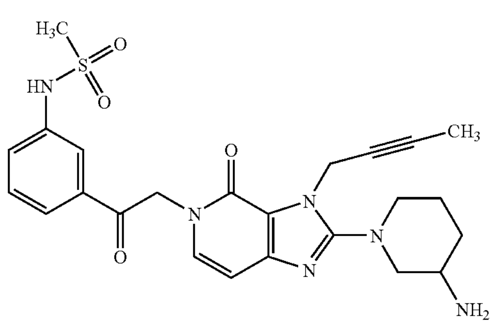 | (66) | 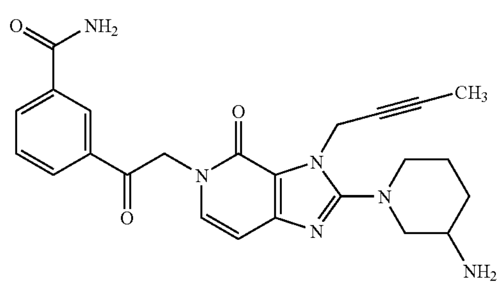 |

-continued

| Ex. | Structure | Ex. | Structure |
| --- | --- | --- | --- |
| (67) | 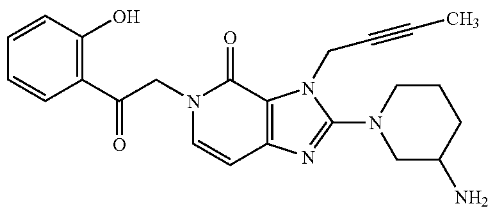 | (68) | 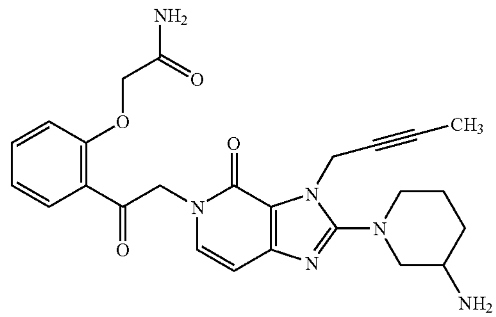 |
| (69) | 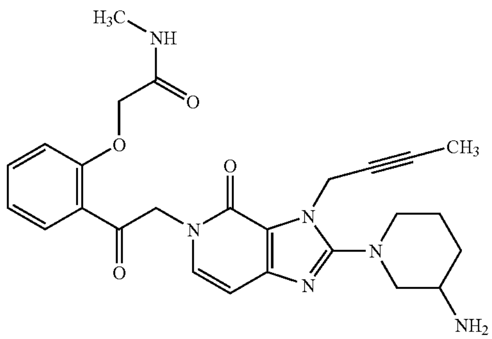 | (70) | 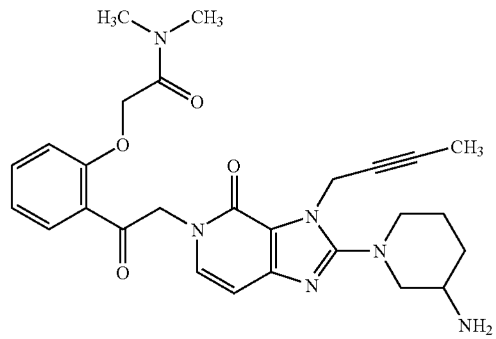 |
| (71) | 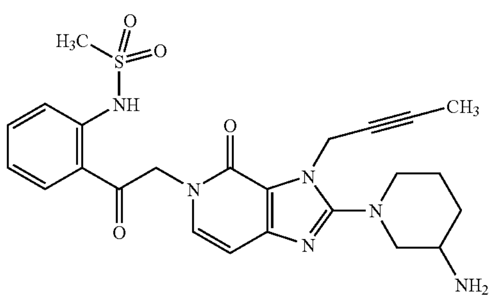 | (72) | 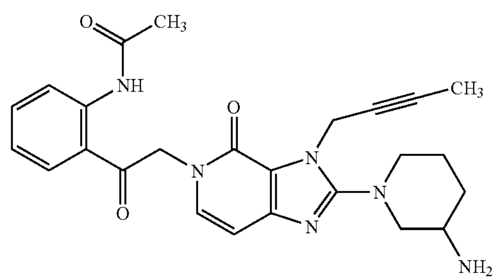 |
| (73) | 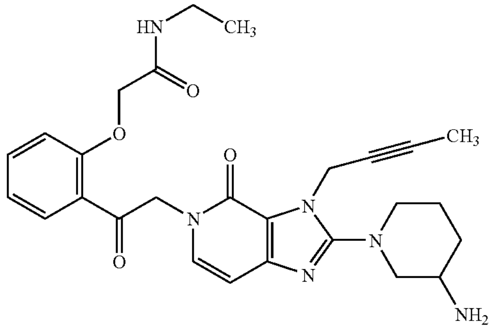 | (74) | 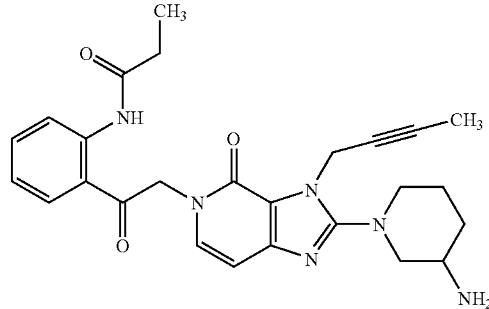 |

-continued

| Ex. | Structure | Ex. | Structure |
| --- | --- | --- | --- |
| (75) | 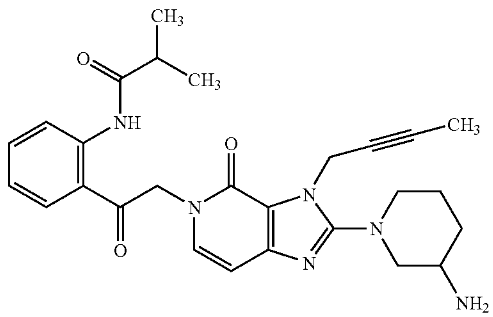 | (76) | 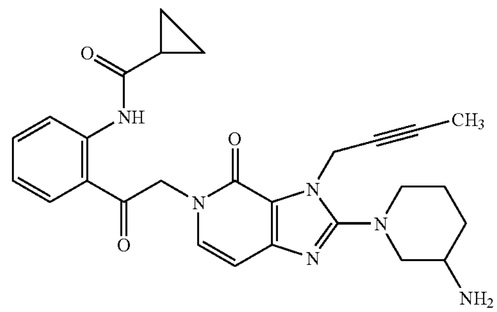 |
| (77) | 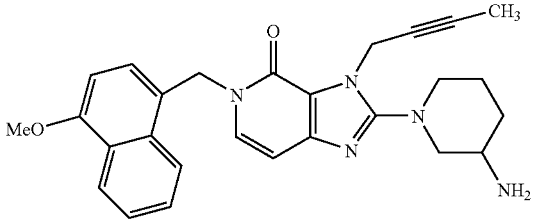 | (78) | 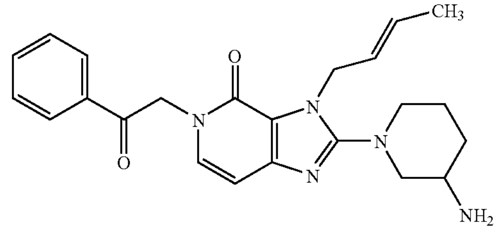 |
| (79) | 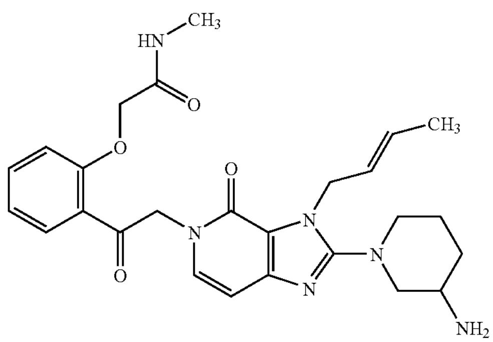 | (80) | 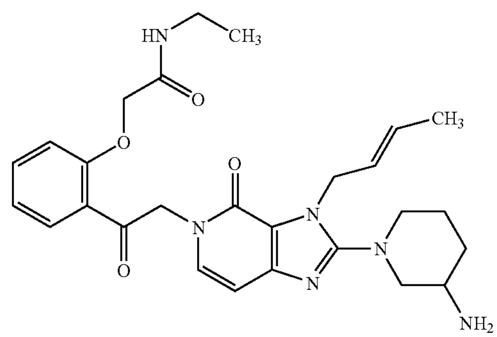 |
| (81) | 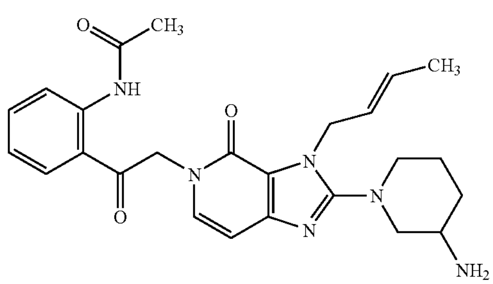 | (82) | 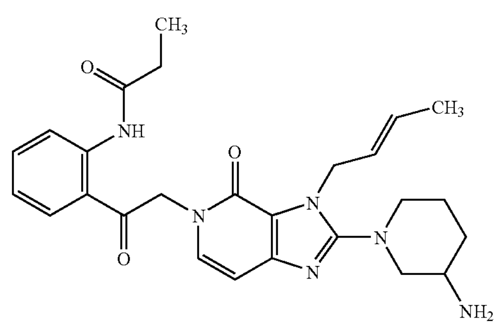 |
| (83) | 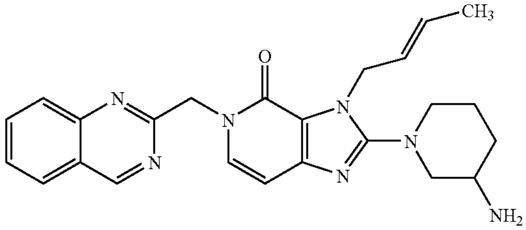 | (84) | 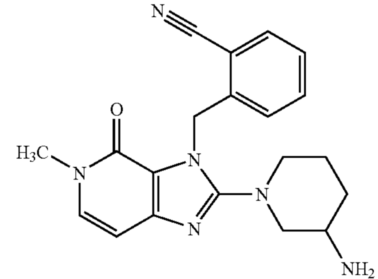 |

-continued

| Ex. | Structure | Ex. | Structure |
|---|---|---|---|
| (85) | 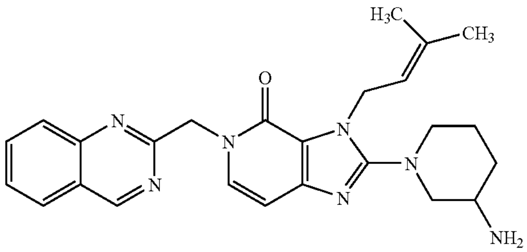 | (86) | 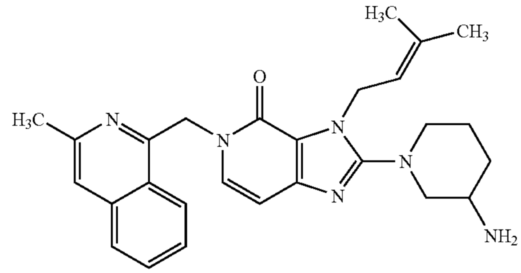 |
| (87) | 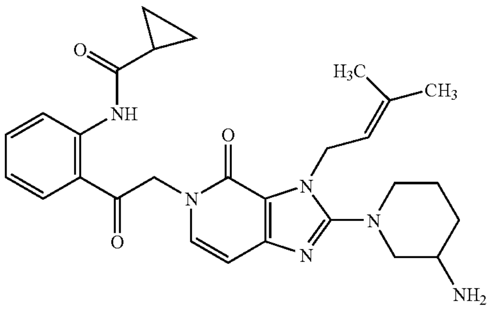 | (88) | 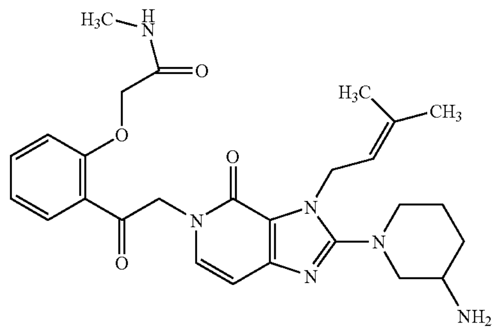 |
| (89) | 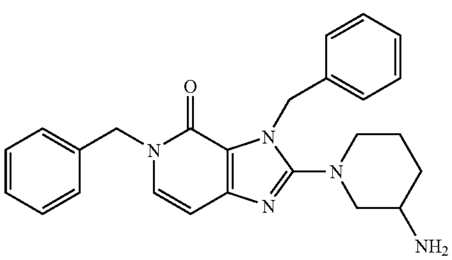 | (90) | 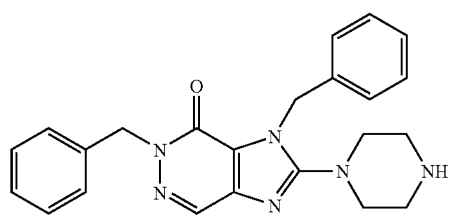 |
| (91) | 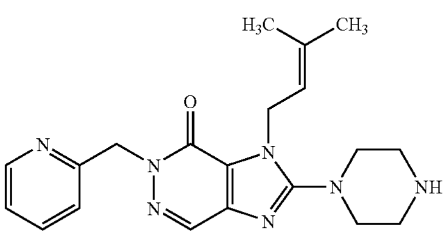 | (92) | 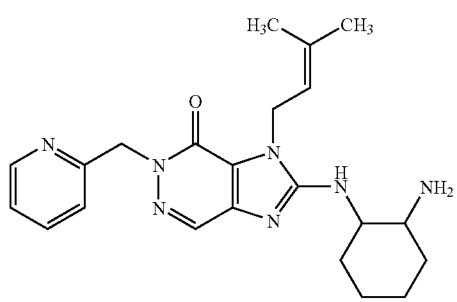 |
| (93) | 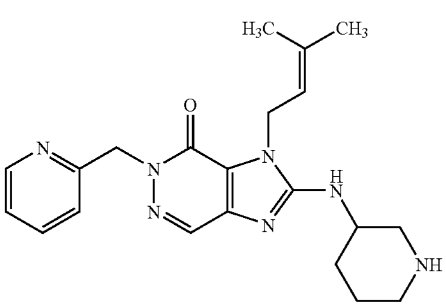 | (94) | 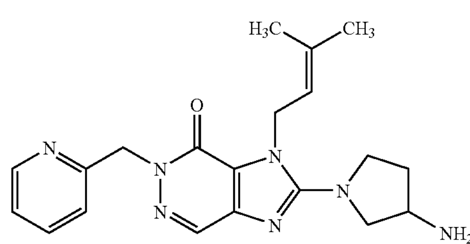 |

-continued

| Ex. | Structure | Ex. | Structure |
|---|---|---|---|
| (95) | 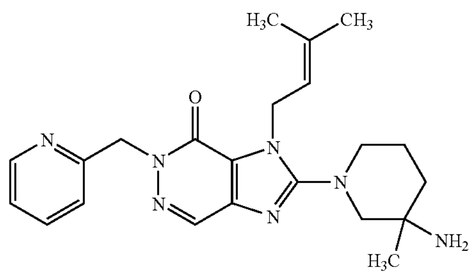 | (96) | 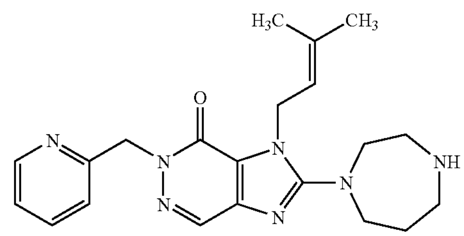 |
| (97) | 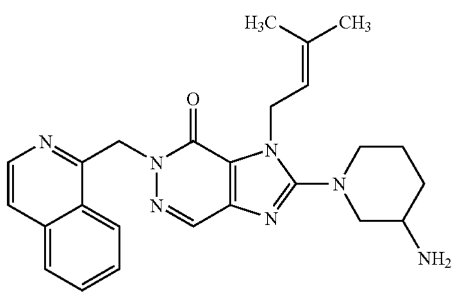 | (98) | 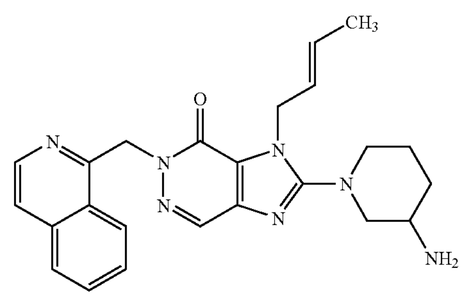 |
| (99) | 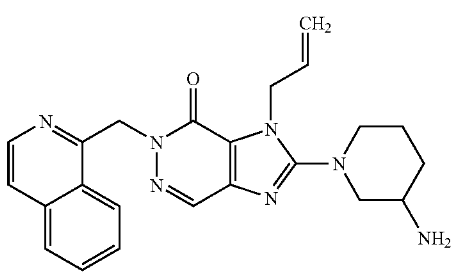 | (100) | 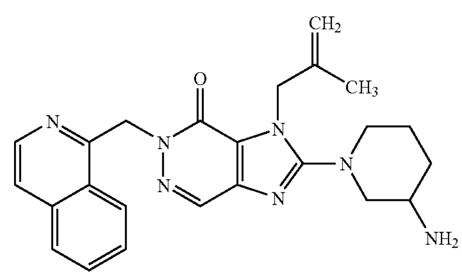 |
| (101) | 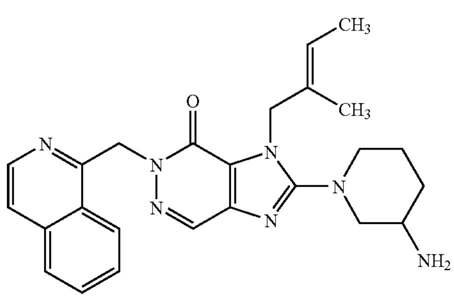 | (102) | 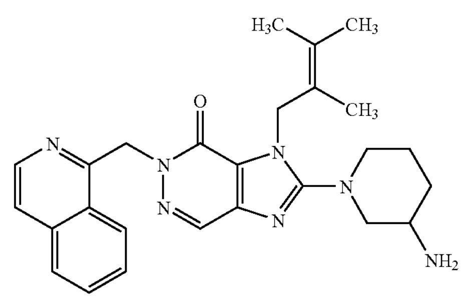 |
| (103) | 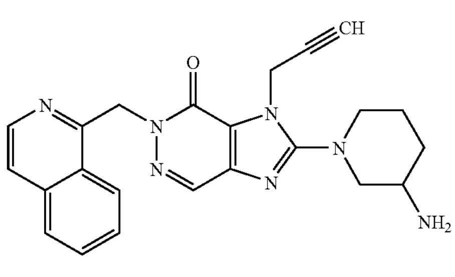 | (104) | 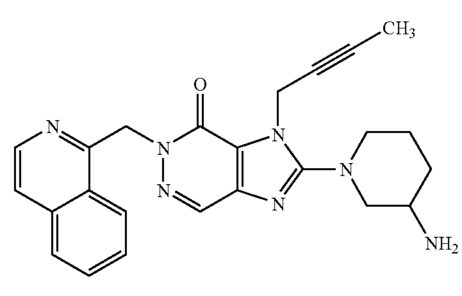 |

-continued

| Ex. | Structure | Ex. | Structure |
|-----|-----------|-----|-----------|
| (105) | 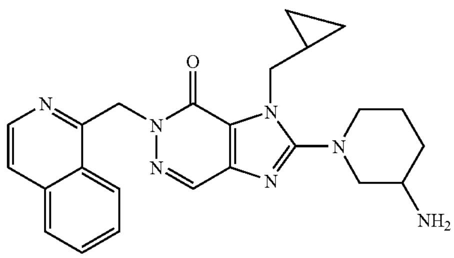 | (106) | 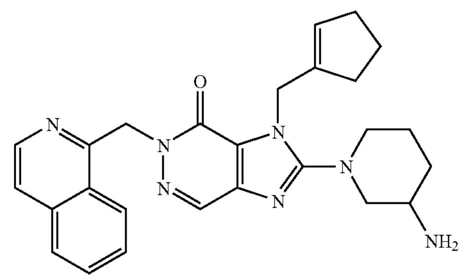 |
| (107) | 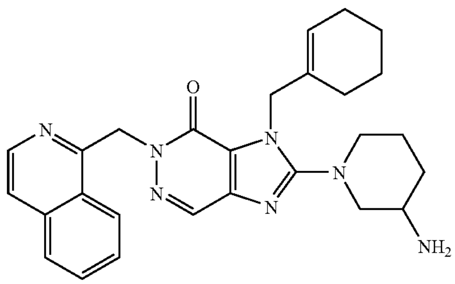 | (108) | 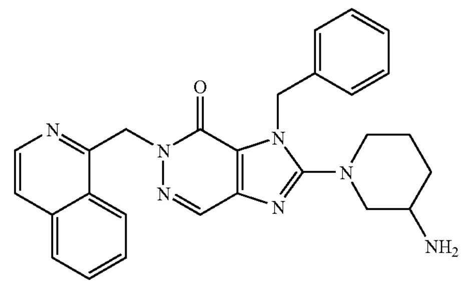 |
| (109) | 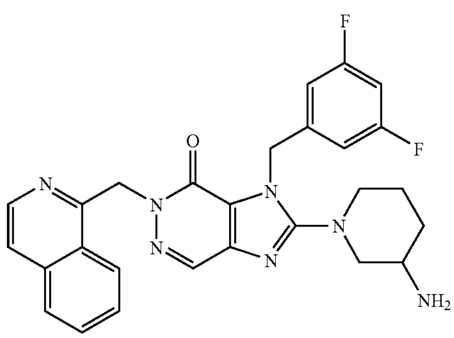 | (110) | 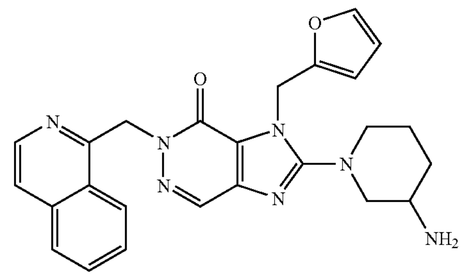 |
| (111) | 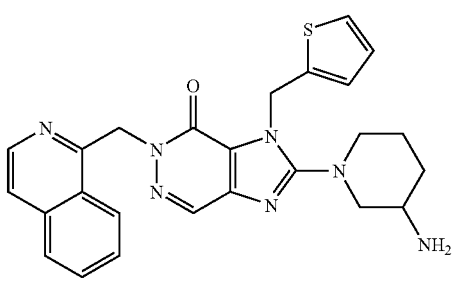 | (112) | 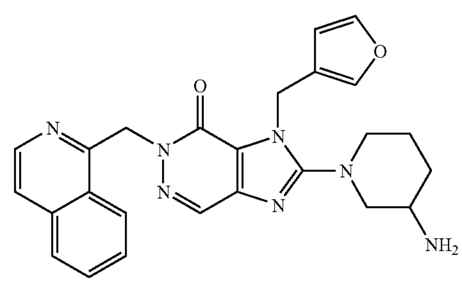 |
| (113) | 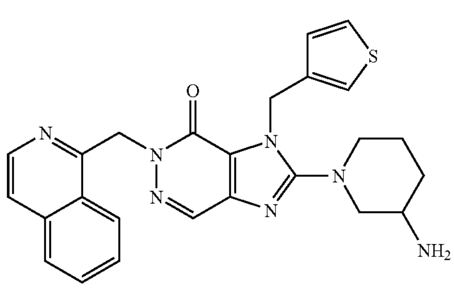 | (114) | 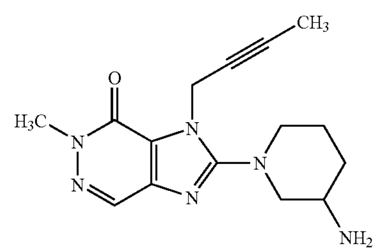 |

-continued

| Ex. | Structure | Ex. | Structure |
|---|---|---|---|
| (115) | 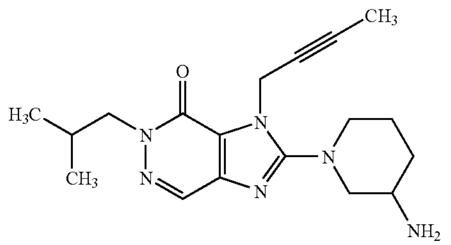 | (116) | 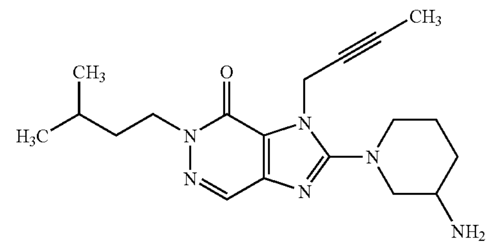 |
| (117) | 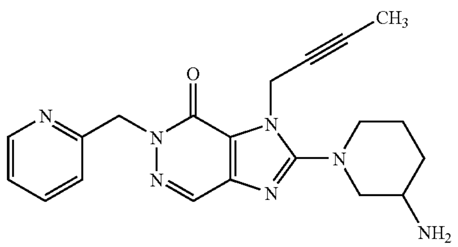 | (118) | 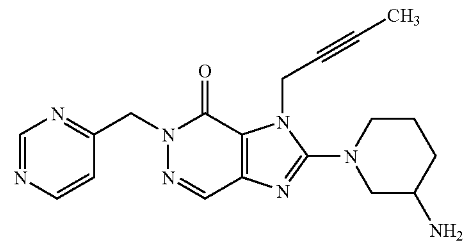 |
| (119) | 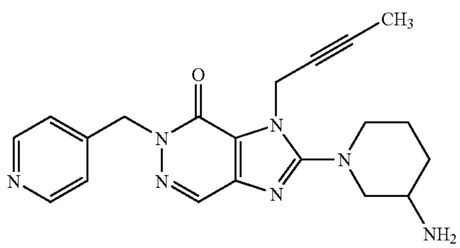 | (120) | 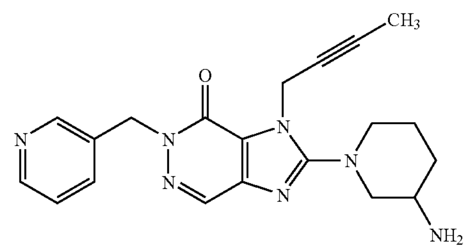 |
| (121) | 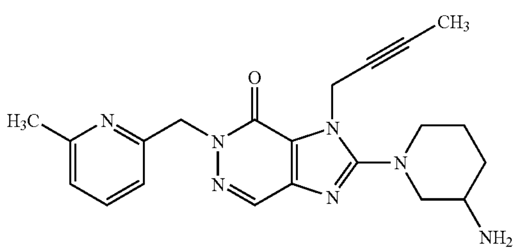 | (122) | 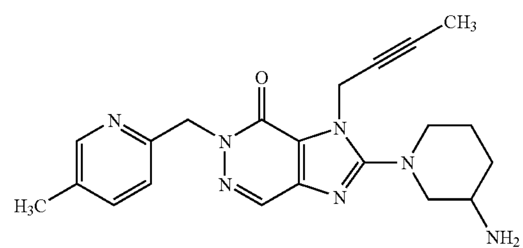 |
| (123) | 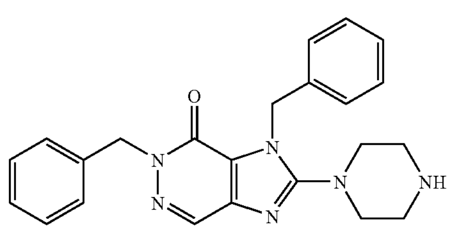 | (124) | 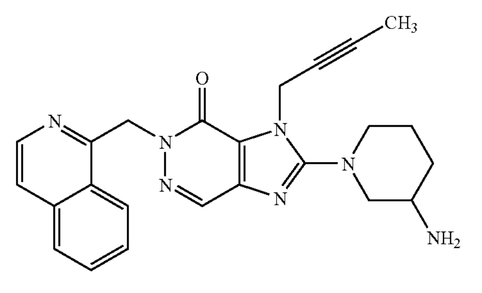 |
| (125) | 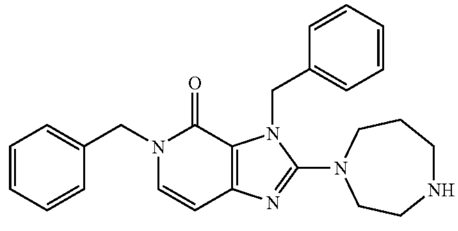 | (126) | 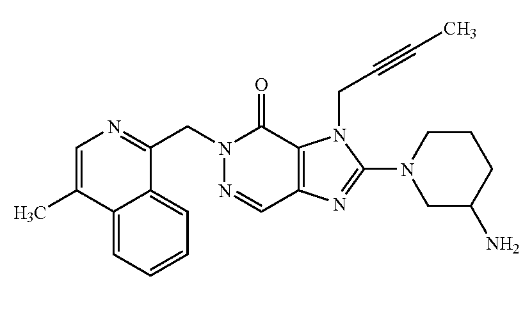 |

-continued

| Ex. | Structure | Ex. | Structure |
|---|---|---|---|
| (127) | 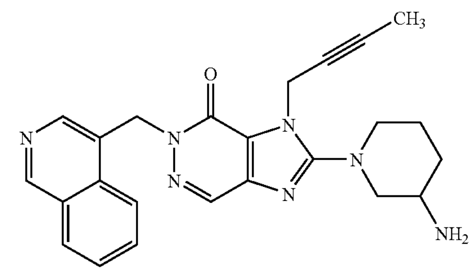 | (128) | 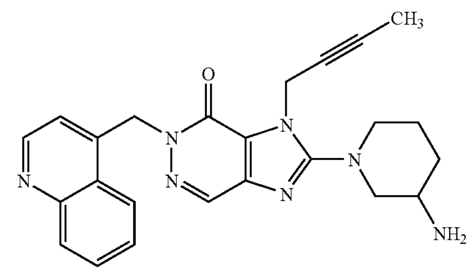 |
| (129) | 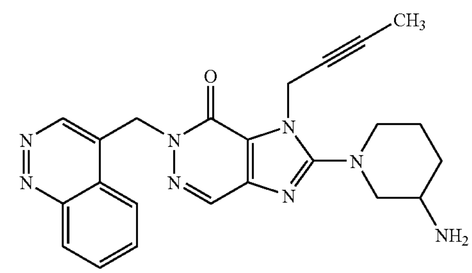 | (130) | 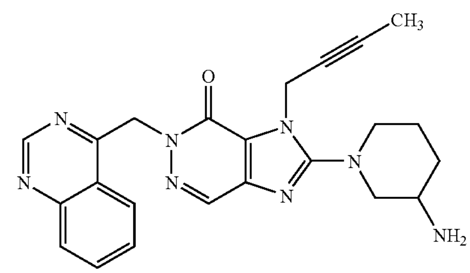 |
| (131) | 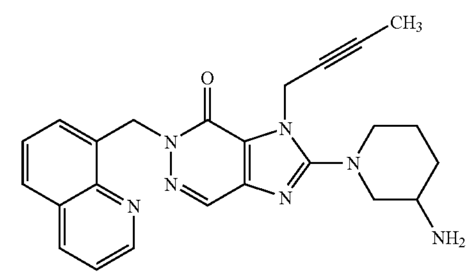 | (132) | 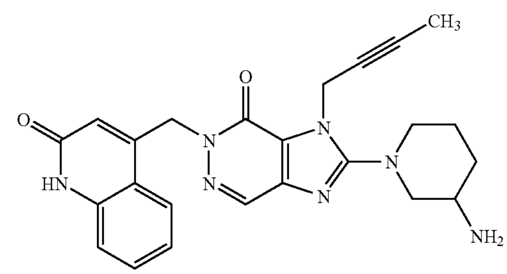 |
| (133) | 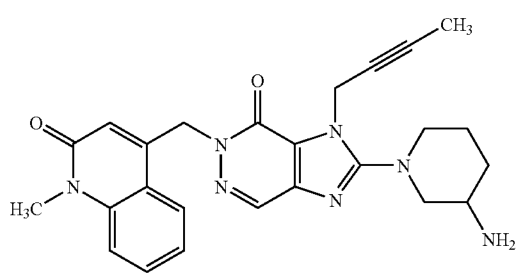 | (134) | 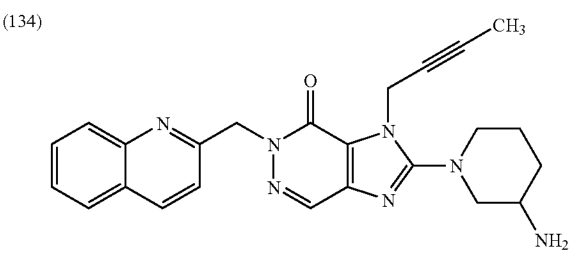 |
| (135) | 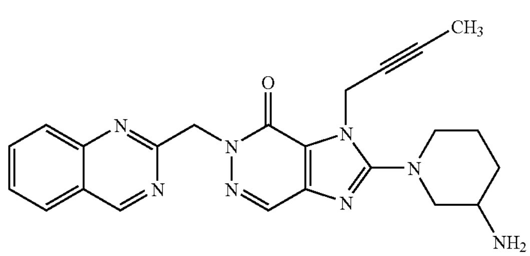 | (136) | 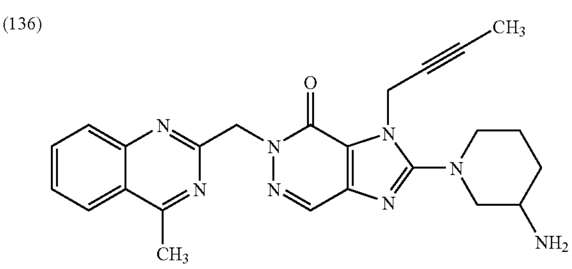 |

-continued

| Ex. | Structure | Ex. | Structure |
|---|---|---|---|
| (137) | 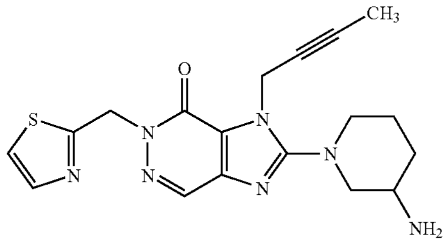 | (138) | 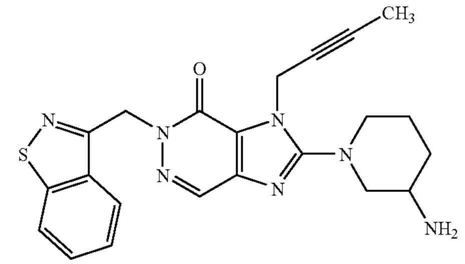 |
| (139) | 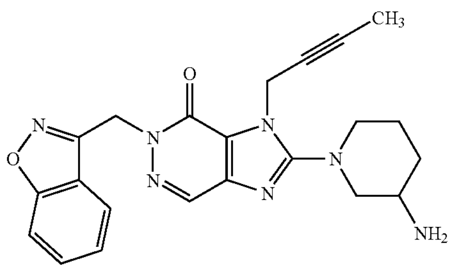 | (140) | 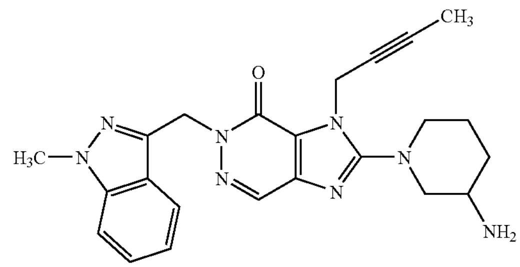 |
| (141) | 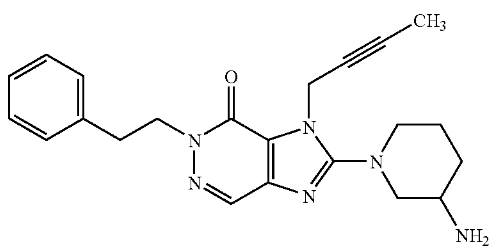 | (142) | 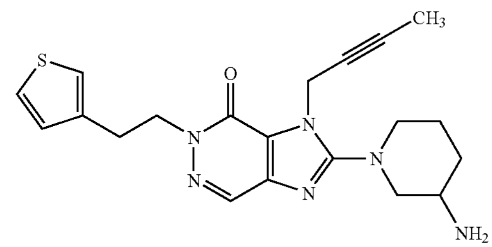 |
| (143) | 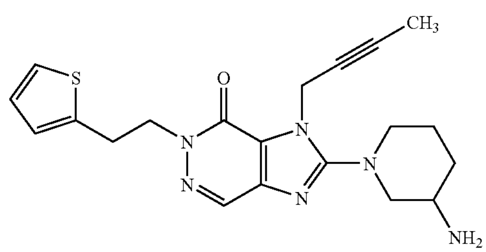 | (144) | 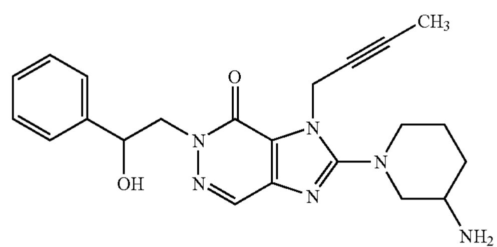 |
| (145) | 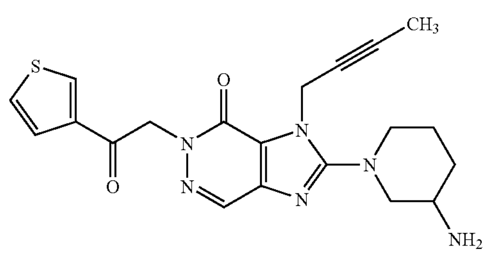 | (146) | 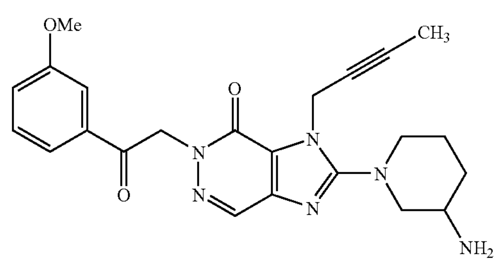 |
| (147) | 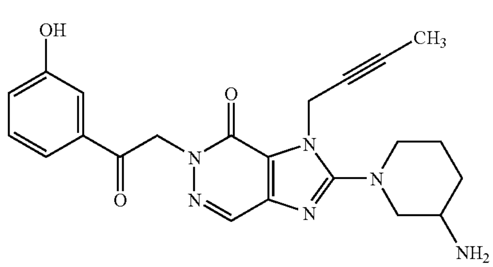 | (148) | 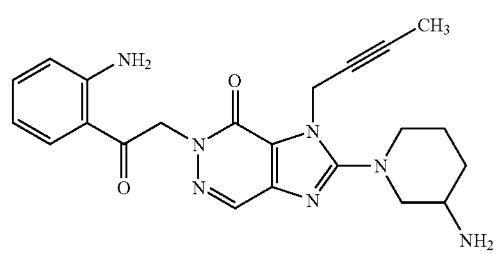 |

-continued

| Ex. | Structure | Ex. | Structure |
|---|---|---|---|
| (149) | 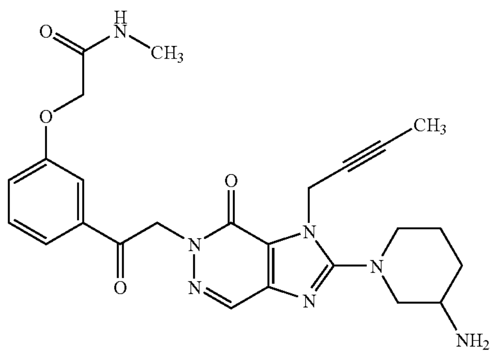 | (150) | 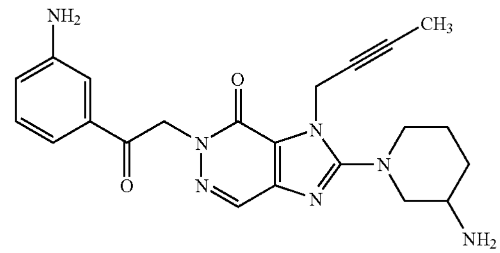 |
| (151) | 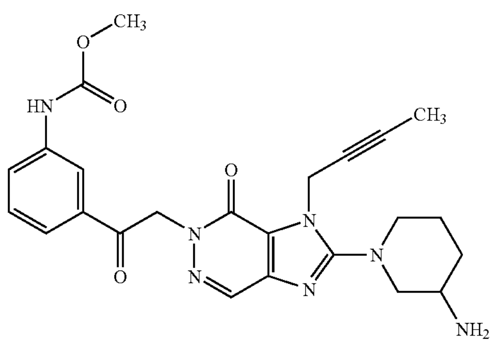 | (152) | 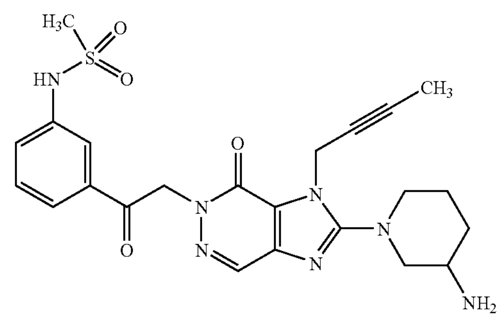 |
| (153) | 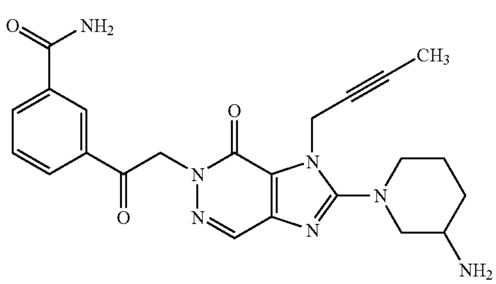 | (154) | 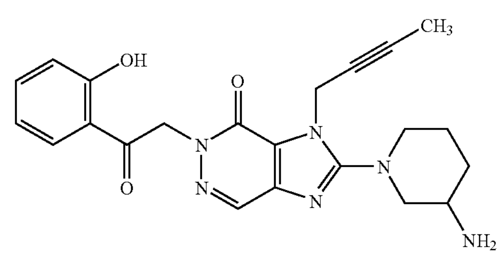 |
| (155) | 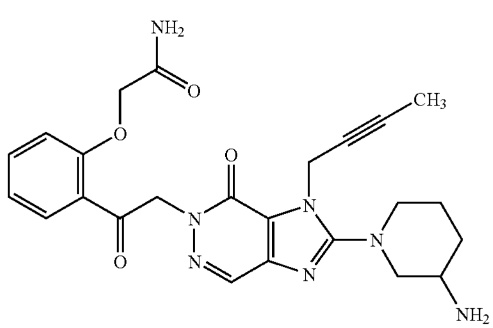 | (156) | 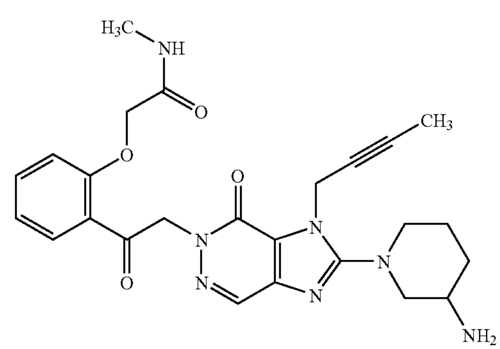 |

-continued

| Ex. | Structure | Ex. | Structure |
|---|---|---|---|
| (157) | 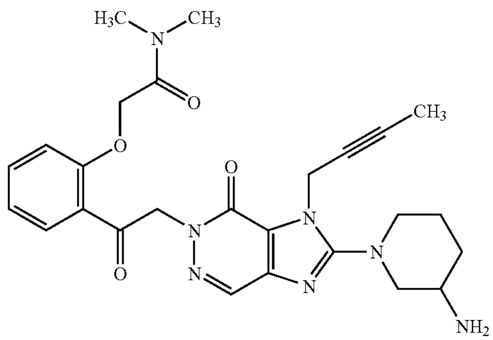 | (158) | 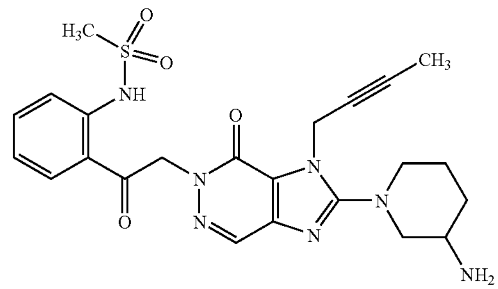 |
| (159) | 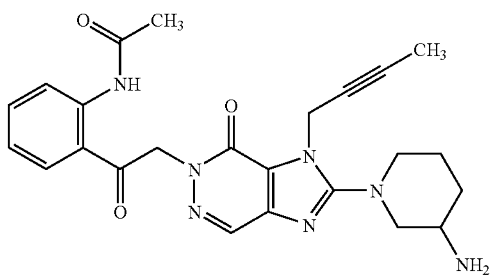 | (160) | 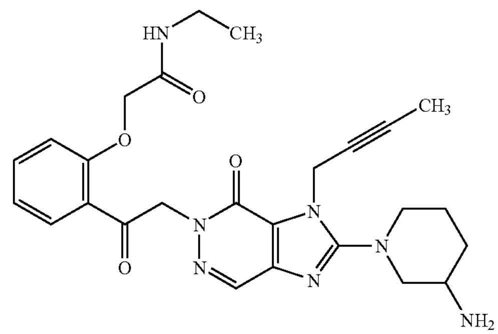 |
| (161) | 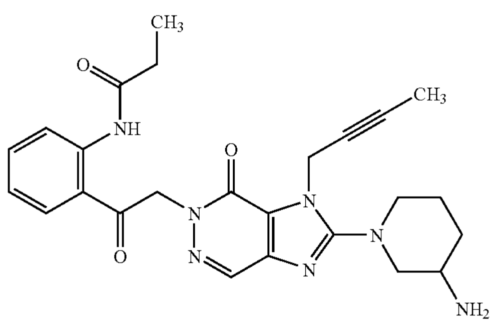 | (162) | 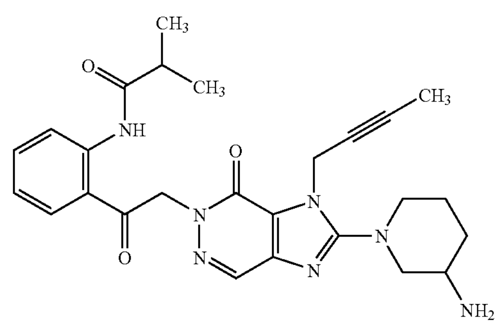 |
| (163) | 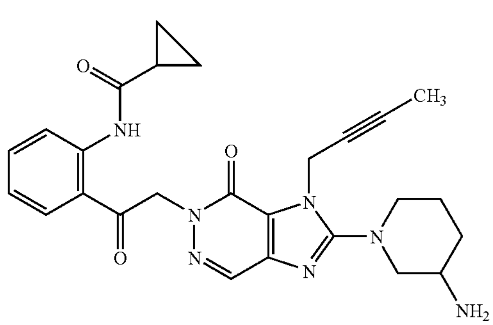 | (164) | 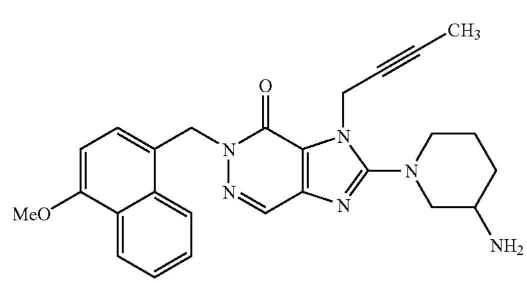 |

-continued

| Ex. | Structure | Ex. | Structure |
|---|---|---|---|
| (165) | 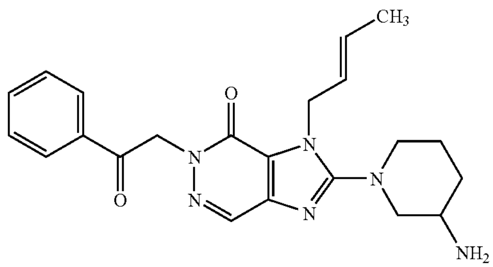 | (166) | 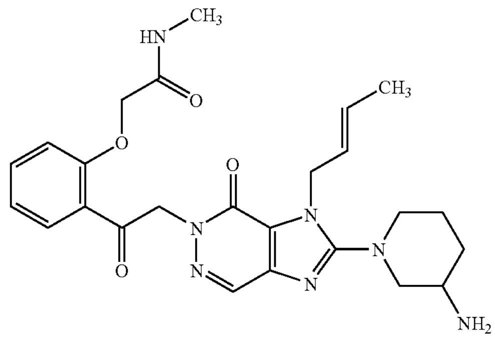 |
| (167) | 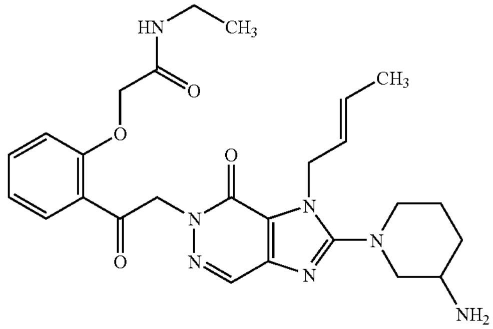 | (168) | 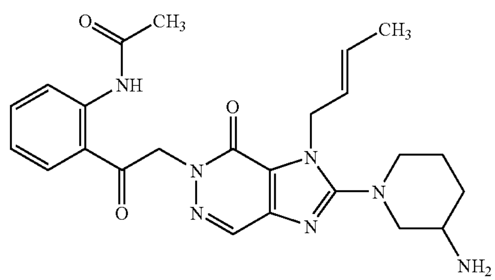 |
| (169) | 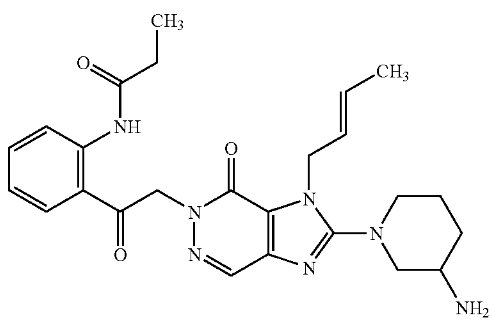 | (170) | 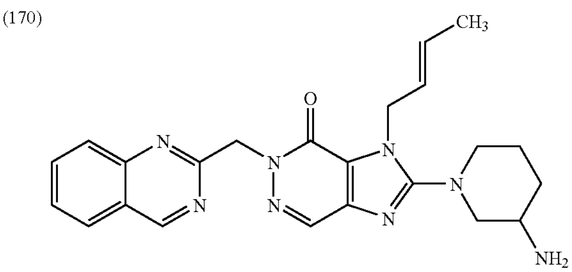 |
| (171) | 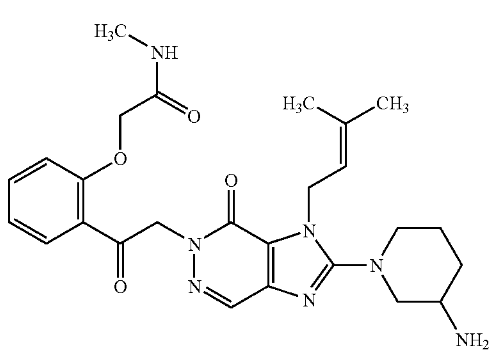 | (172) | 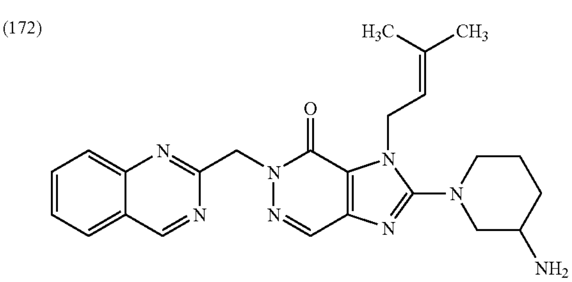 |

-continued

| Ex. | Structure | Ex. | Structure |
|---|---|---|---|
| (173) | 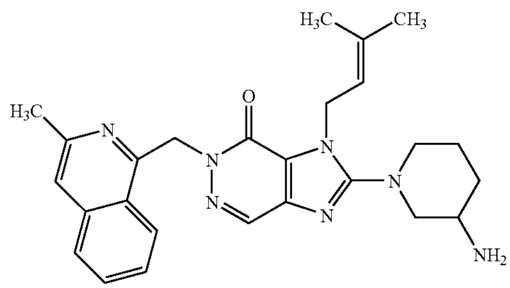 | (174) | 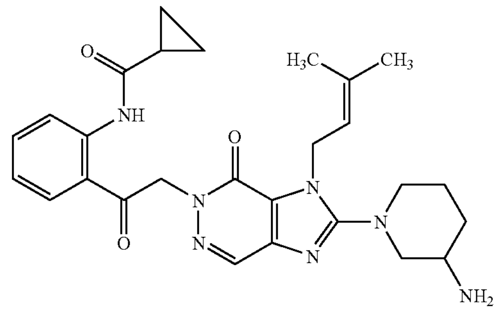 |
| (175) | 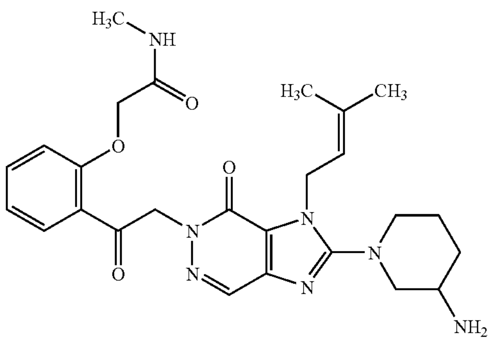 | (176) | 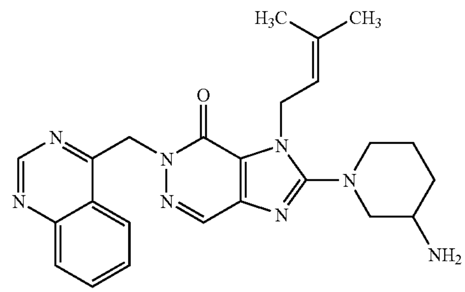 |
| (177) | 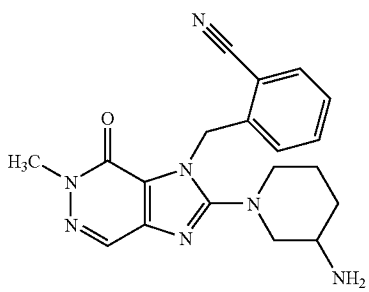 | (178) | 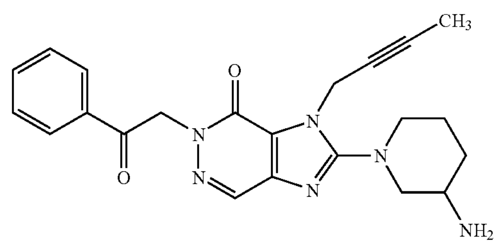 |
| (179) | 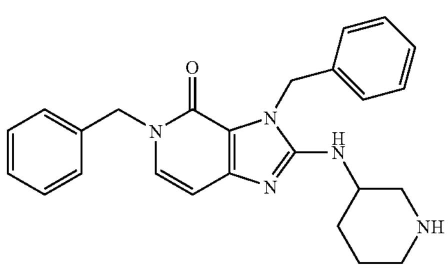 | (180) | 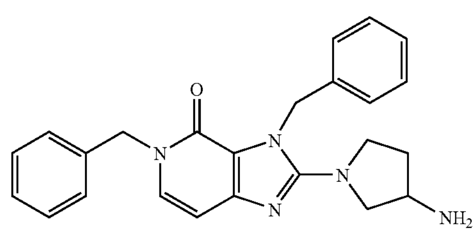 |
| (181) | 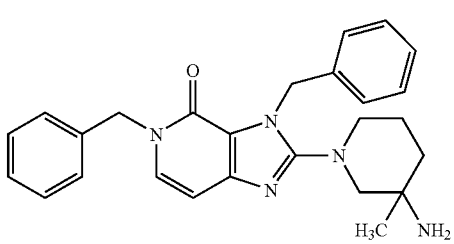 | | |

EXAMPLE 182

2-(3-amino-piperidin-1-yl)-3-(but-2-ynyl)-5-(quinoxalin-6-ylmethyl)-3,5-dihydro-imidazo[4,5-d]pyridazin-4-one

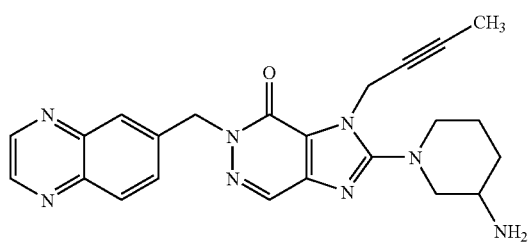

Prepared analogously to Example 1j by cleaving the Boc protective group with trifluoroacetic acid in dichloromethane.

Yield: 69% of theory.

$C_{23}H_{24}N_8O$ (428.50)

Mass spectrum: $(M+H)^+=429$ $^1$H-NMR spectrum ($d_6$-DMSO): δ=1.22–1.33 (m, 1H); 1.60–1.94 (m 5H); 2.75–3.08 (m, 3H); 3.53–3.70 (m, 2H); 5.10 (s, 2H); 5.60 (s, 2H); 7.79 (dd, 1H); 7.90 (s, 1H); 8.08 (d, 1H); 8.32 (s, 1H); 8.92 (s, 2H) ppm (exchangeable protons not visible).

EXAMPLE 183

2-(3-amino-piperidin-1-yl)-3-(but-2-ynyl)-5-(4-methyl-pyridin-2-ylmethyl)-3,5-dihydro-imidazo[4,5-d]pyridazin-4-one

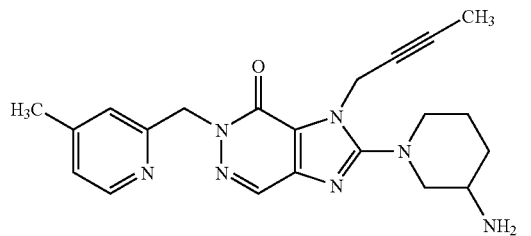

Prepared analogously to Example 1j by cleaving the Boc protective group with trifluoroacetic acid in dichloromethane.

Yield: 90% of theory.

$C_{21}H_{25}N_7O \times 2$ HCl (464.40)

Rf value: 0.43 (silica gel; dichloromethane/methanol 7:3)

Mass spectrum: $(M+H)^+=392$ $^1$H-NMR spectrum ($d_6$-DMSO): δ=1.65–1.80 (m, 2H); 1.80 (s, 3H); 1.90–2.10 (m, 2H); 3.15–3.43 (m, 3H); 3.45–3.55 (m, 1H); 3.72–3.82 (m, 1H); 5.18 (q, 2H); 5.70 (s, 2H); 7.58 (s, 1H); 7.79 (d, 1H); 8.39 (s, 1H); 8.60 (broad s; 2H); 8.73 (d, 1H) ppm.

EXAMPLE 184

2-((R)-3-amino-piperidin-1-yl)-3-(but-2-ynyl)-5-(4-phenyl-quinazolin-2-ylmethyl)-3,5-dihydro-imidazo[4,5-d]pyridazin-4-one

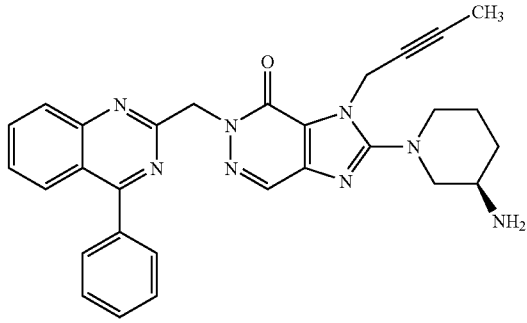

Prepared analogously to Example 1j by cleaving the Boc protective group with trifluoroacetic acid in dichloromethane.

Yield: 63% of theory.

$C_{29}H_{28}N_8O$ (504.60)

Mass spectrum: $(M+H)^+=505$ $^1$H-NMR spectrum ($d_6$-DMSO): δ=1.22–1.33 (m, 1H); 1.60–1.95 (m, 5H); 2.78 (dd, 1H); 2.85–3.06 (m, 2H); 3.56–3.72 (m, 2H); 5.11 (s, 2H); 5.72 (s, 2H); 7.56–7.75 (m, 6H); 7.90–8.03 (m, 2H); 8.08 (d, 1H); 8.30 (s, 1H) ppm.

EXAMPLE 185

2-((R)-3-amino-piperidin-1-yl)-3-(but-2-ynyl)-5-(quinoxalin-2-ylmethyl)-3,5-dihydro-imidazo[4,5-d]pyridazin-4-one

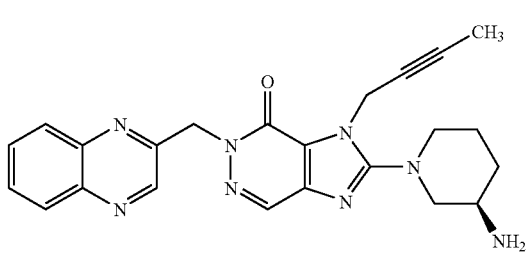

Prepared analogously to Example 1j by cleaving the Boc protective group with trifluoroacetic acid in dichloromethane.

Yield: 88% of theory.

$C_{23}H_{24}N_8O \times HCl$ (464.96)

Mass spectrum: $(M+H)^+=429$ $^1$H-NMR spectrum ($d_6$-DMSO): δ=1.63–1.75 (m, 2H); 1.77 (s, 3H); 1.88–2.10 (m, 2H); 3.13–3.26 (m, 2H); 3.35–3.56 (m, 2H); 3.75 (dd, 1H); 5.15 (q, 2H); 5.71 (s, 2H); 7.80–7.86 (m, 2H); 7.99 (m, 1H); 8.09 (m, 1H); 8.33 (s, 1H); 8.45 (broad s, 2H); 8.92 (s, 1H) ppm.

EXAMPLE 186

2-((R)-3-amino-piperidin-1-yl)-3-(but-2-ynyl)-5-(2,3-dimethyl-quinoxalin-6-ylmethyl)-3,5-dihydro-imidazo[4,5-d]pyridazin-4-one

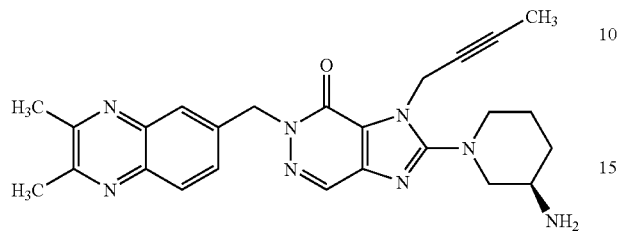

Prepared analogously to Example 1j by cleaving the Boc protective group with trifluoroacetic acid in dichloromethane.

Yield: 52% of theory.

$C_{25}H_{28}N_8O$ (456.56)

Mass spectrum: (M+H)$^+$=457

$^1$H-NMR spectrum (d$_6$-DMSO): δ=1.18–1.31 (m, 1H); 1.58–1.72 (m, 1H); 1.73–1.93 (m, 5H); 2.66 (s, 3H); 2.68 (s, 3H); 2.75 (dd, 1H); 2.83–3.05 (m, 1H); 3.55–3.68 (m, 2H); 5.10 (s, 2H); 5.53 (s, 2H); 7.62 (dd, 1H); 7.70 (s, 1H); 7.92 (d, 1H); 8.31 (s, 1H) ppm.

EXAMPLE 187

2-((R)-3-amino-piperidin-1-yl)-3-(but-2-ynyl)-5-(4-cyano-naphthalen-1-ylmethyl)-3,5-dihydro-imidazo[4,5-d]pyridazin-4-one

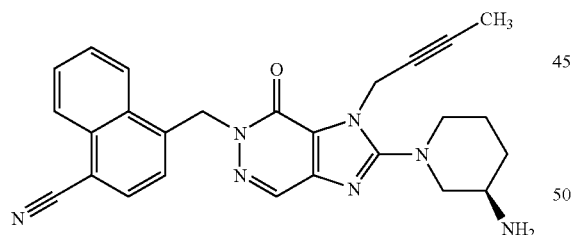

Prepared analogously to Example 1j by cleaving the Boc protective group with trifluoroacetic acid in dichloromethane.

Yield: 62% of theory.

$C_{26}H_{25}N_7O$ (451.53)

Mass spectrum: (M+H)$^+$=452

$^1$H-NMR spectrum (d$_6$-DMSO): δ=1.22–1.32 (m, 1H); 1.58–1.71 (m, 1H); 1.75–1.93 (m, 5H); 2.77 (dd, 1H); 2.83–3.05 (m, 2H); 3.55–3.70 (m, 2H); 5.60 (s, 2H); 5.88 (s, 2H); 7.28 (d, 1H); 7.76–7.88 (m, 2H); 8.10 (d, 1H); 8.17 (d, 1H); 8.30 (s, 1H); 8.47 (d, 1H) ppm.

EXAMPLE 188

2-(3-amino-piperidin-1-yl)-3-(3-methyl-but-2-enyl)-5-(2-oxo-2-phenyl-ethyl)-3,5-dihydro-imidazo[4,5-c]pyridin-4-one

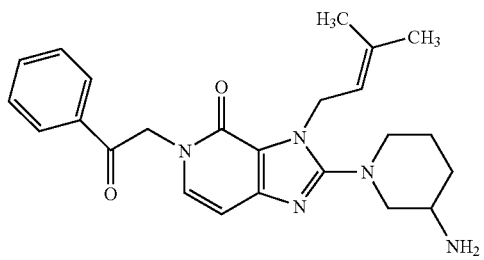

Prepared analogously to Example 1j by cleaving the Boc protective group with trifluoroacetic acid in dichloromethane.

Yield: 69% of theory.

$C_{24}H_{29}NO_2$ (419.53)

Mass spectrum: (M+H)$^+$=420

$^1$H-NMR spectrum (d$_6$-DMSO): δ=1.15–1.27 (m, 1H); 1.57–1.92 (m, 9H); 2.55–2.70 (m, 2H); 2.76–2.92 (m, 2H); 3.41 (dt, 1H); 4.80 (d, 2H); 5.32 (t, 1H); 5.04 (s, 2H); 6.51 (d, 1H); 7.34 (d, 1H); 7.60 (t, 2H); 7.70 (t, 1H); 8.08 (d, 2H) ppm.

EXAMPLE 189

2-(3-amino-piperidin-1-yl)-3-(3-methyl-but-2-enyl)-5-(2-oxo-2-phenyl-ethyl)-3,5-dihydro-imidazo[4,5-d]pyridazin-4-one

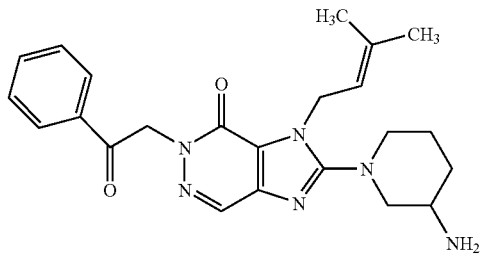

Prepared analogously to Example 1j by cleaving the Boc protective group with trifluoroacetic acid in dichloromethane.

Yield: 88% of theory.

$C_{22}H_{24}N_6O_2$ (404.47)

Mass spectrum: (M+H)$^+$=405

$^1$H-NMR spectrum (d$_6$-DMSO): δ=1.55 (m, 1H); 1.70 (m, 1H); 1.88 (m, 1H); 1.99 (m, 1H); 3.05–3.22 (m, 3H); 3.57 (m, 1H); 3.71 (dt, 1H); 5.11 (s, 2H); 5.70 (s, 2H); 7.60 (t, 2H); 7.72 (t, 1H); 8.08 (d, 2H); 8.32 (s, 1H) ppm.

EXAMPLE 190

2-(3-amino-piperidin-1-yl)-3-(3-methyl-but-2-enyl)-5-(naphthalen-1-ylmethyl)-3,5-dihydro-imidazo[4,5-c]pyridin-4-one

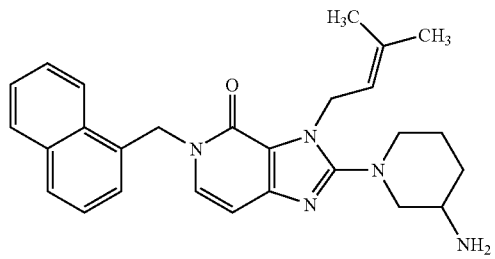

Prepared analogously to Example 1j by cleaving the Boc protective group with trifluoroacetic acid in dichloromethane.

Yield: 86% of theory.

$C_{27}H_{31}N_5O$ (441.58)

Mass spectrum: $(M+H)^+=442$ $^1$H-NMR spectrum ($d_6$-DMSO): δ=1.13–1.75 (m, 1H); 1.57–1.95 (m, 9H); 2.57 (dd, 1H); 2.83 (m, 2H); 3.30–3.47 (m, 2H); 4.87 (d, 2H); 5.39 (t, 1H); 5.68 (s, 2H); 6.50 (d, 1H); 7.09 (d, 1H); 7.32 (d, 1H); 7.42 (t, 1H); 7.58 (m, 2H); 7.89 (d, 1H); 7.98 (d, 1H); 8.21 (d, 1H) ppm.

EXAMPLE 191

2-((R)-3-amino-piperidin-1-yl)-3-(but-2-ynyl)-5-(4-fluoronaphthalen-1-ylmethyl)-3,5-dihydro-imidazo[4,5-d]pyridazin-4-one hydrochloride

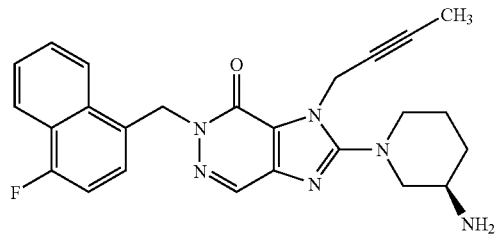

Prepared analogously to Example 1j by cleaving the Boc protective group with trifluoroacetic acid in dichloromethane.

Yield: 88% of theory.

$C_{25}H_{25}FN_6O$ (444.52)

Mass spectrum: $(M+H)^+=445$ $^1$H-NMR spectrum ($d_6$-DMSO): δ=1.70 (m, 2H); 1.81 (s, 3H); 1.94 (m, 1H); 2.03 (m, 1H); 3.19 (m, 2H); 3.40 (m, 1H); 3.50 M, 1H); 3.74 (m, 1H); 5.19 (m, 2H); 5.77 (s, 2H); 7.28 (d, 2H); 7.76 (m, 2H); 8.10 (d, 1H); 8.31 (s, 1H); 8.38 (d, 1H); 8.47 (broad s, 3H) ppm.

EXAMPLE 192

2-((R)-3-amino-piperidin-1-yl)-3-(but-2-ynyl)-5-(6-methylbenzoxazol-2-ylmethyl)-3,5-dihydro-imidazo[4,5-d]pyridazin-4-one hydrochloride

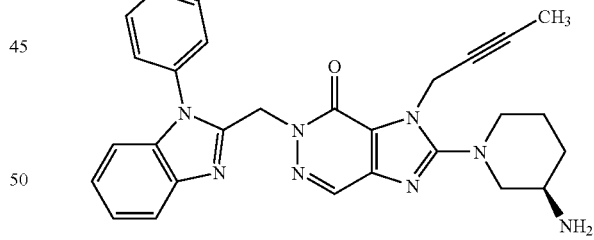

Prepared analogously to Example 1j by cleaving the Boc protective group with trifluoroacetic acid in dichloromethane.

Yield: 81% of theory.

$C_{23}H_{25}N_7O_2$ (431.50)

Mass spectrum: $(M+H)^+=432$ $^1$H-NMR spectrum ($d_6$-DMSO): δ=1.70 (m, 2H); 1.80 (s, 3H); 1.94 (m, 1H); 2.04 (m, 1H); 2.43 (s, 3H); 3.21 (m, 2H); 3.40 (m, 1H); 3.51 (m, 1H); 3.75 (m, 1H); 5.15 (dd, 2H); 5.63 (s, 2H); 7.17 (d, 1H); 7.50 (s, 1H); 7.56 (d, 1H); 8.35 (s, 1H); 8.46 (broad s, 3H) ppm.

EXAMPLE 193

2-((R)-3-amino-piperidin-1-yl)-3-(but-2-ynyl)-5-(1-phenylbenzimidazol-2-ylmethyl)-3,5-dihydro-imidazo[4,5-d]pyridazin-4-one hydrochloride Prepared analogously to Example 1j by cleaving the Boc protective group with trifluoroacetic acid in dichloromethane.

Yield: 62% of theory.

$C_{28}H_{28}N_8O$ (492.59)

Mass spectrum: $(M+H)^+=493$ $^1$H-NMR spectrum ($d_6$-DMSO): δ=1.72 (m, 2H); 1.80 (s, 3H); 1.95 (m, 1H); 2.03 (m, 1H); 3.21 (m, 2H); 3.40 (m, 1H); 3.49 (m, 1H); 5.08 (dd, 2H); 5.75 (s, 2H); 7.31 (d, 1H); 7.45–7.66 (m, 7H); 7.86 (d, 1H); 8.22 (s, 1H); 8.54 (broad s, 3H) ppm.

EXAMPLE 194

2-((R)-3-amino-piperidin-1-yl)-3-(but-2-ynyl)-5-(4-methylbenzoxazol-2-ylmethyl)-3,5-dihydro-imidazo[4,5-d]pyridazin-4-one hydrochloride

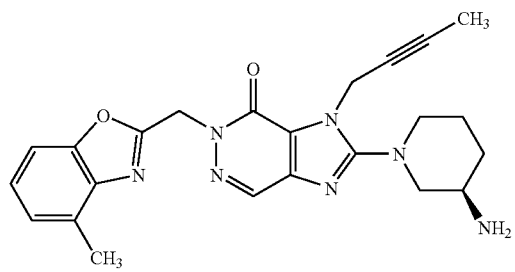

Prepared analogously to Example 1j by cleaving the Boc protective group with trifluoroacetic acid in dichloromethane.

Yield: 83% of theory.

$C_{23}H_{25}N_7O_2$ (431.50)

Mass spectrum: $(M+H)^+=432$ $^1$H-NMR spectrum (d$_6$-DMSO): δ=1.71 (m, 2H); 1.80 (s, 3H); 1.93 (m, 1H); 2.05 (m, 1H); 3.22 (m, 2H); 3.41 (m, 1H); 3.53 (m, 1H); 3.75 (m, 1H); 5.16 (dd, 2H); 5.66 (s, 2H); 7.20 (d, 1H); 7.27 (t, 1H); 7.48 (d, 1H); 8.35 (s, 1H); 8.44 (broad s, 3H) ppm.

EXAMPLE 195

2-((R)-3-amino-piperidin-1-yl)-3-(but-2-ynyl)-5-(5-trifluoromethylbenzothiazol-2-ylmethyl)-3,5-dihydro-imidazo[4,5-d]pyridazin-4-one hydrochloride

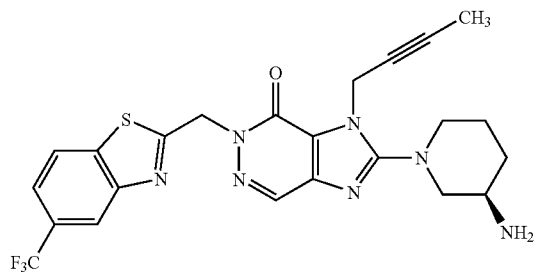

Prepared analogously to Example 1j by cleaving the Boc protective group with trifluoroacetic acid in dichloromethane.

Yield: 98% of theory.

$C_{23}H_{22}F_3N_7OS$ (501.54)

Mass spectrum: $(M+H)^+=502$ $^1$H-NMR spectrum (d$_6$-DMSO): δ=1.70 (m, 2H); 1.80 (s, 3H); 1.95 (m, 1H); 2.05 (m, 1H); 3.22 (m, 2H); 3.40 (m, 1H); 3.52 (m, 1H); 3.77 (m, 1H); 5.19 (dd, 2H); 5.82 (s, 2H); 7.77 (d, 1H); 8.31 (d, 1H); 8.35 (s, 1H); 8.41 (s, 1H); 8.50 (broad s, 3H) ppm.

EXAMPLE 196

2-((R)-3-amino-piperidin-1-yl)-3-(but-2-ynyl)-5-(5-chlorobenzoxazol-2-ylmethyl)-3,5-dihydro-imidazo[4,5-d]pyridazin-4-one hydrochloride

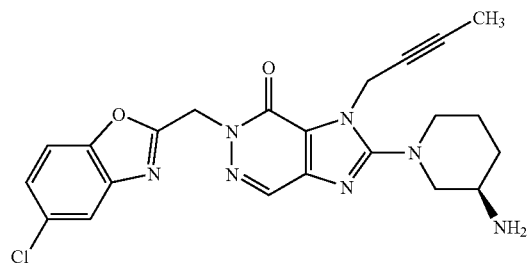

Prepared analogously to Example 1j by cleaving the Boc protective group with trifluoroacetic acid in dichloromethane.

Yield: 77% of theory.

$C_{22}H_{22}ClN_7O_2$ (451.92)

Mass spectrum: $(M+H)^+=452$ $^1$H-NMR spectrum (d$_6$-DMSO): δ=1.71 (m, 2H); 1.80 (s, 3H); 1.94 (m, 1H); 2.05 (m, 1H); 3.22 (m, 2H); 3.41 (m, 1H); 3.53 (m, 1H); 3.75 (m, 1H); 5.16 (dd, 2H); 5.69 (s, 2H); 7.43 (d, 1H); 7.75 (d, 1H); 7.83 (s, 1H); 8.39 (s, 1H); 8.97 (broad s, 3H) ppm.

EXAMPLE 197

2-((R)-3-amino-piperidin-1-yl)-3-(but-2-ynyl)-5-(5-methylbenzoxazol-2-ylmethyl)-3,5-dihydro-imidazo[4,5-d]pyridazin-4-one hydrochloride

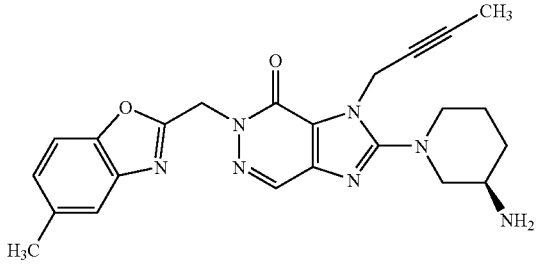

Prepared analogously to Example 1j by cleaving the Boc protective group with trifluoroacetic acid in dichloromethane.

Yield: 57% of theory.

$C_{23}H_{25}N_7O_2$ (431.50)

Mass spectrum: $(M+H)^+=432$ $^1$H-NMR spectrum (d$_6$-DMSO): δ=1.71 (m, 2H); 1.80 (s, 3H); 1.93 (m, 1H); 2.04 (m, 1H); 2.41 (s, 3H); 3.21 (m, 2H); 3.40 (m, 1H); 3.53 (m, 1H); 3.75 (m, 1H); 5.16 (dd, 2H); 5.64 (s, 2H); 7.20 (d, 1H); 7.49 (s, 1H); 7.57 (d, 1H); 8.38 (s, 1H); 8.92 (broad s, 3H) ppm.

EXAMPLE 198

2-((R)-3-amino-piperidin-1-yl)-3-(but-2-ynyl)-5-[1-(pyridin-3-yl)-benzimidazol-2-ylmethyl]-3,5-dihydro-imidazo[4,5-d]pyridazin-4-one hydrochloride

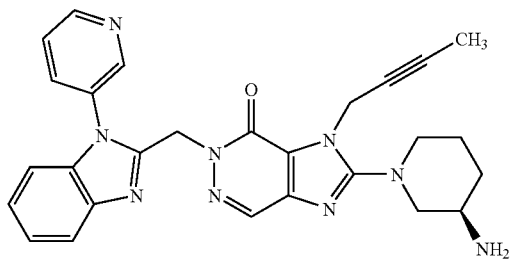

Prepared analogously to Example 1j by cleaving the Boc protective group with trifluoroacetic acid in dichloromethane.

Yield: 37% of theory.

$C_{27}H_{27}N_9O$ (493.58)

Mass spectrum: $(M+H)^+=494$ $^1$H-NMR spectrum ($d_6$-DMSO): δ=1.71 (m, 2H); 1.81 (s, 3H); 1.95 (m, 1H); 2.02 (m, 1H); 3.22 (m, 2H); 3.40 (m, 1H); 3.48 (m, 1H); 3.73 (m, 1H); 5.08 (dd, 2); 5.67 (s, 2H); 7.28 (d, 1H); 7.41 (m, 2H); 7.70 (dd, 1H); 7.28 (d, 1H); 8.17 (d, 1H); 8.22 (s, 1H); 8.43 (broad s, 3H); 8.78 (d, 1H); 8.88 (s, 1H) ppm.

EXAMPLE 199

2-((R)-3-amino-piperidin-1-yl)-3-(but-2-ynyl)-5-(5,7-dimethylbenzoxazol-2-ylmethyl)-3,5-dihydro-imidazo[4,5-d]pyridazin-4-one hydrochloride

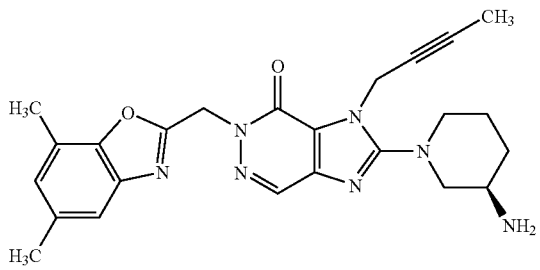

Prepared analogously to Example 1j by cleaving the Boc protective group with trifluoroacetic acid in dichloromethane.

Yield: 86% of theory.

$C_{24}H_{27}N_7O_2$ (445.53)

Mass spectrum: $(M+H)^+=446$ $^1$H-NMR spectrum ($d_6$-DMSO): δ=1.71 (m, 2H); 1.80 (s, 3H); 1.94 (m, 1H); 2.05 (m, 1H); 2.36 (s, 3H); 2.42 (s, 3H); 3.22 (m, 2H); 3.41 (m, 1H); 3.54 (m, 1H); 3.75 (m, 1H); 5.16 (dd, 2H); 5.63 (s, 2H); 7.02 (s, 1H); 7.28 (s, 1H); 8.34 (s, 1H); 8.41 (broad s, 3H) ppm.

EXAMPLE 200

2-((R)-3-amino-piperidin-1-yl)-3-(but-2-ynyl)-5-(4-chloronaphth-1-ylmethyl)-3,5-dihydro-imidazo[4,5-d]pyridazin-4-one

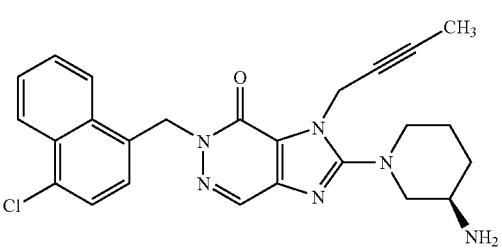

Prepared analogously to Example 1j by cleaving the Boc protective group with trifluoroacetic acid in dichloromethane.

Yield: 54% of theory.

$C_{25}H_{25}ClN_6O$ (460.97)

Mass spectrum: $(M+H)^+=461/3$ $^1$H-NMR spectrum ($d_6$-DMSO): δ=1.22 (m, 1H); 1.62 (m, 1H); 1.73 (m, 1H); 1.80 (s, 3H); 1.87 (m, 1H); 2.73 (m, 1H); 2.99 (m, 1H); 3.60 (m, 2H); 5.12 (s, 2H); 5.80 (s, 2H); 7.22 (d, 1H); 7.65 (d, 1H) 7.72 (m, 2H); 8.23 (d, 1H); 8.30 (s, 1H); 8.39 (d, 1H) ppm.

EXAMPLE 201

2-((R)-3-amino-piperidin-1-yl)-3-(but-2-ynyl)-5-(4-bromonaphth-1-ylmethyl)-3,5-dihydro-imidazo[4,5-d]pyridazin-4-one hydrochloride

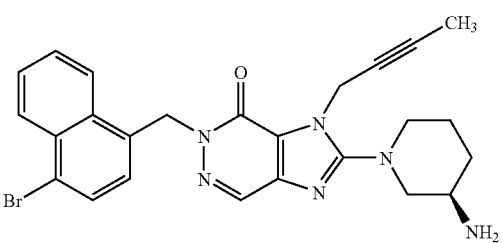

Prepared analogously to Example 1j by cleaving the Boc protective group with trifluoroacetic acid in dichloromethane.

Yield: 67% of theory.

$C_{25}H_{25}BrN_6O$ (505.42)

Mass spectrum: $(M+H)^+=505/7$ $^1$H-NMR spectrum ($d_6$-DMSO): δ=1.70 (m, 2H); 1.80 (s, 3H); 1.93 (m, 1H); 2.04 (m, 1H); 3.20 (m, 2H); 3.40 (m, 1H); 3.51 (m, 1H); 3.74 (m, 1H); 5.17 (dd, 2H); 5.78 (s, 2H); 7.16 (d, 1H); 7.70 (m, 2H); 7.83 (d, 1H); 8.20 (d, 1H); 8.32 (s, 1H); 8.37 (d, 1H); 8.47 (broad s, 3H) ppm.

EXAMPLE 202

2-((R)-3-amino-piperidin-1-yl)-3-(but-2-ynyl)-5-(benzo[1,2,5]oxadiazol-5-ylmethyl)-3,5-dihydro-imidazo[4,5-d]pyridazin-4-one

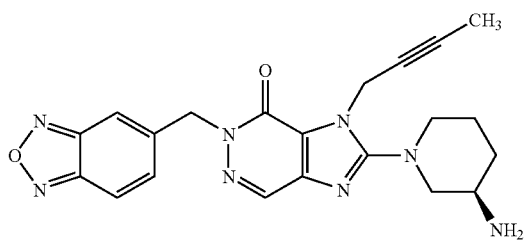

Prepared analogously to Example 1j by cleaving the Boc protective group with trifluoroacetic acid in dichloromethane.

Yield: 83% of theory.

$C_{21}H_{22}N_8O_2$ (418.46)

Mass spectrum: $(M+H)^+=419$ $^1$H-NMR spectrum ($d_6$-DMSO): δ=1.41 (m, 1H); 1.67 (m, 1H); 1.80 (s, 3H); 1.82 (m, 1H); 1.93 (m, 1H); 2.42 (dd, 1H); 3.10 (m, 2H); 3.57 (m, 1H); 3.68 (dd, 1H); 5.11 (s, 2H); 5.47 (s, 2H); 7.53 (d, 1H); 7.76 (s, 1H); 8.04 (d, 1H); 8.3 (s, 1H); ppm

EXAMPLE 203

2-((R)-3-amino-piperidin-1-yl)-3-(but-2-ynyl)-5-(benzo[1,2,5]thiadiazol-4-ylmethyl)-3,5-dihydro-imidazo[4,5-d]pyridazin-4-one

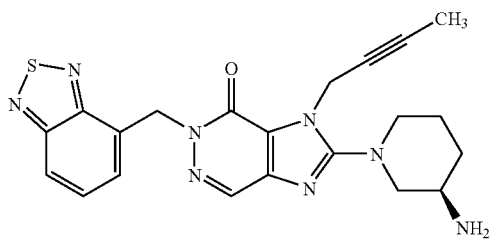

Prepared analogously to Example 1j by cleaving the Boc protective group with trifluoroacetic acid in dichloromethane.

Yield: 73% of theory.

$C_{21}H_{22}N_8OS$ (434.53)

Mass spectrum: $(M+H)^+=435$ $^1$H-NMR spectrum ($d_6$-DMSO): δ=1.30 (m, 1H); 1.65 (m, 1H); 1.79 (s, 3H); 1.82 (m, 1H); 1.90 (m, 1H) 2.82 (dd, 1H); 2.96 (m, 1H); 3.04 (m, 1H); 3.61 (m, 1H); 3.66 (dd, 1H); 5.12 (s, 2H); 5.84 (s, 2H); 7.22 (d, 1H); 7.64 (t, 1H); 8.01 (d, 1H); 8.30 (s, 1H); ppm.

EXAMPLE 204

2-((R)-3-amino-piperidin-1-yl)-3-(but-2-ynyl)-5-(benzo[1,2,5]thiadiazol-5-ylmethyl)-3,5-dihydro-imidazo[4,5-d]pyridazin-4-one

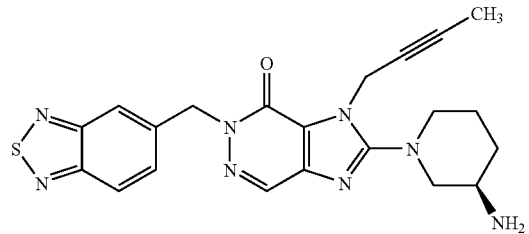

Prepared analogously to Example 1j by cleaving the Boc protective group with trifluoroacetic acid in dichloromethane.

Yield: 81% of theory.

$C_{21}H_{22}N_8OS$ (434.53)

Mass spectrum: $(M+H)^+=435$ $^1$H-NMR spectrum ($d_6$-DMSO): δ=1.30 (m, 1H); 1.65 (m, 1H); 1.79 (s, 3H); 1.81 (m, 1H); 1.90 (m, 1H); 2.32 (dd, 1H); 2.95 (m, 1H); 3.03 (m, 1H); 3.57 (m, 1H); 3.65 (dd, 1H); 5.11 (s, 2H); 5.54 (s, 2H); 7.66 (d, 1H); 7.85 (s, 1H); 8.07 (d, 1H); 8.31 (s, 1H) ppm.

EXAMPLE 205

2-((R)-3-amino-piperidin-1-yl)-3-(2-chlorobenzyl)-5-(3-methyl-isoquinolin-1-ylmethyl)-3,5-dihydro-imidazo[4,5-d]pyridazin-4-one

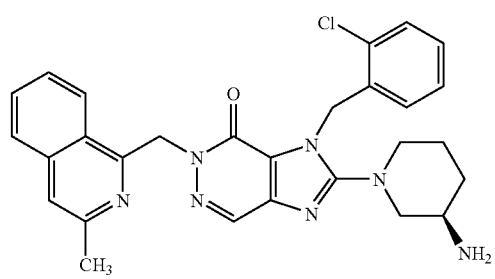

Prepared analogously to Example 1j by cleaving the Boc protective group with trifluoroacetic acid in dichloromethane.

Yield: 70% of theory.

$C_{28}H_{28}ClN_7O$ (514.03)

Mass spectrum: $(M+H)^+=514/6$ $^1$H-NMR spectrum ($d_6$-DMSO): δ=1.14 (m, 1H), 1.46 (m, 1H); 1.64 (m, 1H); 1.79 (m, 1H); 2.44 (s, 3H); 2.62 (dd, 1H); 2.70)m, 1H); 2.85 (m, 1H); 3.20–3.44 (m, 2H); 5.63 (s, 2H); 5.88 (s, 2H); 6.70 (d, 1H); 7.25 (t, 1H); 7.32 (t, 1H); 7.52 (m, 3H); 7.71 (t, 1H); 7.85 (d, 1H); 8.18 (d, 1H); 8.30 (s, 1H) ppm.

EXAMPLE 206

2-((R)-3-amino-piperidin-1-yl)-3-(but-2-ynyl)-5-(2-methyl-naphthalen-1-ylmethyl)-3,5-dihydro-imidazo[4,5-d]pyridazin-4-one

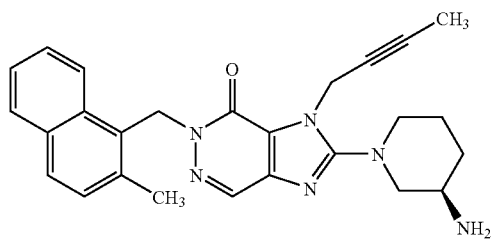

Prepared analogously to Example 1j by cleaving the Boc protective group with trifluoroacetic acid in dichloromethane.

Yield: 56% of theory.
$C_{26}H_{28}N_6O$ (440.55)
Mass spectrum: $(M+H)^+=441$
Rf value: 0.29 (silica gel; dichloromethane/methanol 9:1)

EXAMPLE 207

2-((R)-3-amino-piperidin-1-yl)-3-(but-2-ynyl)-5-(5-methyl-imidazo[1,2-a]pyridin-2-ylmethyl)-3,5-dihydro-imidazo[4,5-d]pyridazin-4-one

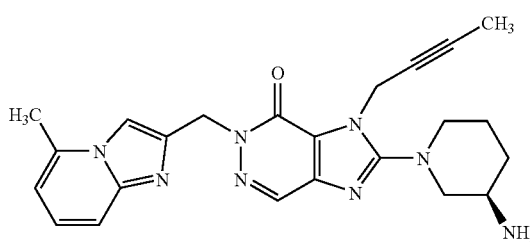

Prepared analogously to Example 1j by cleaving the Boc protective group with trifluoroacetic acid in dichloromethane.

Yield: 86% of theory.
$C_{23}H_{26}N_8O$ (430.52)
Mass spectrum: $(M+H)^+=431$
Rf value: 0.37 (silica gel; dichloromethane/methanol/conc. ammonia 9:1:0.1)

EXAMPLE 208

2-((R)-3-amino-piperidin-1-yl)-3-(but-2-ynyl)-5-(isoquinolin-3-ylmethyl)-3,5-dihydro-imidazo[4,5-d]pyridazin-4-one

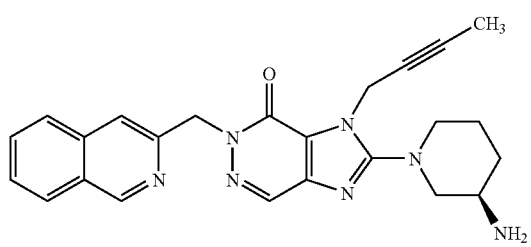

Prepared analogously to Example 1j by cleaving the Boc protective group with trifluoroacetic acid in dichloromethane.

Yield: 97% of theory.
$C_{24}H_{25}N_7O$ (427.51)
Mass spectrum: $(M+H)^+=428$
Rf value: 0.15 (silica gel; dichloromethane/methanol 9:1)

EXAMPLE 209

2-((R)-3-amino-piperidin-1-yl)-3-(but-2-ynyl)-5-(1-methyl-1H-quinolin-2-on-6-ylmethyl)-3,5-dihydro-imidazo[4,5-d]pyridazin-4-one

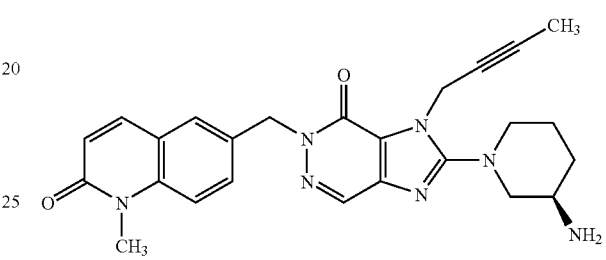

Prepared analogously to Example 1j by cleaving the Boc protective group with trifluoroacetic acid in dichloromethane.

Yield: 32% of theory.
$C_{25}H_{27}N_7O_2$ (457.54)
Mass spectrum: $(M+H)^+=458$
Rf value: 0.11 (silica gel; dichloromethane/methanol 9:1)

EXAMPLE 210

2-((R)-3-amino-piperidin-1-yl)-3-(but-2-ynyl)-5-(2-methyl-2H-indazol-3-ylmethyl)-3,5-dihydro-imidazo[4,5-d]pyridazin-4-one

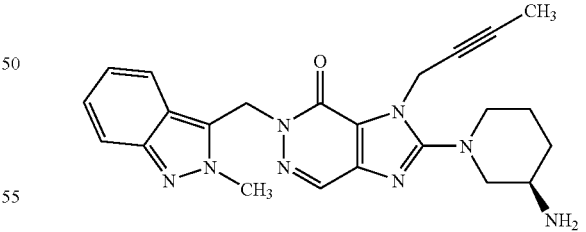

Prepared analogously to Example 1j by cleaving the Boc protective group with trifluoroacetic acid in dichloromethane.

Yield: 84% of theory.
$C_{23}H_{26}N_8O$ (430.52)
Mass spectrum: $(M+H)^+=431$
Rf value: 0.18 (silica gel; dichloromethane/methanol 9:1)

EXAMPLE 211

2-((R)-3-amino-piperidin-1-yl)-3-(but-2-ynyl)-7-methyl-5-(4-phenyl-quinazolin-2-ylmethyl)-3,5-dihydro-imidazo[4,5-d]pyridazin-4-one

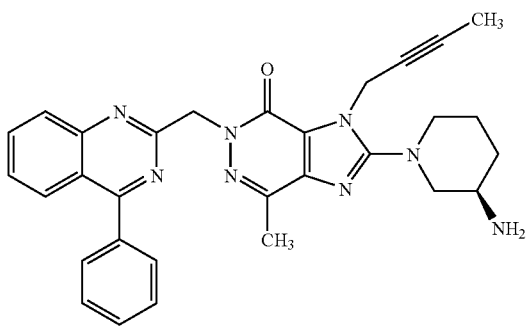

Prepared analogously to Example 1j by cleaving the Boc protective group with trifluoroacetic acid in dichloromethane.

Yield: 29% of theory.
$C_{30}H_{30}N_8O$ (518.63)
Mass spectrum: $(M+H)^+=519$
Rf value: 0.26 (silica gel; dichloromethane/methanol 8:2)

EXAMPLE 212

2-((R)-3-amino-piperidin-1-yl)-3-(but-2-ynyl)-7-methyl-5-(4-methyl-quinazolin-2-ylmethyl)-3,5-dihydro-imidazo[4,5-d]pyridazin-4-one

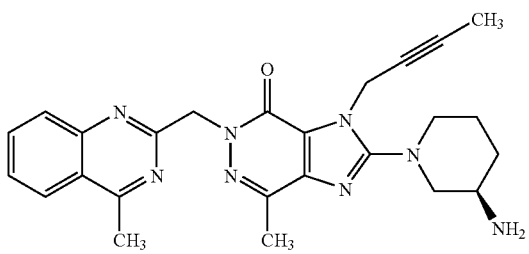

Prepared analogously to Example 1j by cleaving the Boc protective group with trifluoroacetic acid in dichloromethane.

Yield: 61% of theory.
$C_{25}H_{28}N_8O$ (456.55)
Mass spectrum: $(M+H)^+=457$
Rf value: 0.27 (silica gel; dichloromethane/methanol 9:1)

EXAMPLE 213

2-((R)-3-amino-piperidin-1-yl)-3-(but-2-ynyl)-7-methyl-5-(3-methyl-isoquinolin-1-ylmethyl)-3,5-dihydro-imidazo[4,5-d]pyridazin-4-one

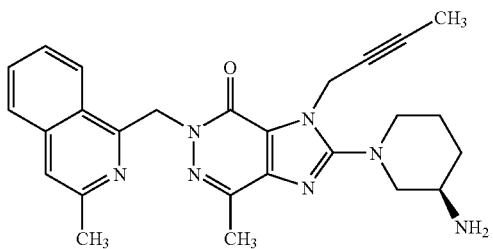

Prepared analogously to Example 1j by cleaving the Boc protective group with trifluoroacetic acid in dichloromethane.

Yield: 56% of theory.
$C_{26}H_{29}N_7O$ (455.57)
Mass spectrum: $(M+H)^+=456$
Rf value: 0.53
(silica gel RP-8; water/acetonitrile/trifluoroacetic acid 50:50:0.1)

EXAMPLE 214

2-((R)-3-amino-piperidin-1-yl)-3-(but-2-ynyl)-5-(1-methyl-1H-indazol-4-ylmethyl)-3,5-dihydro-imidazo[4,5-d]pyridazin-4-one

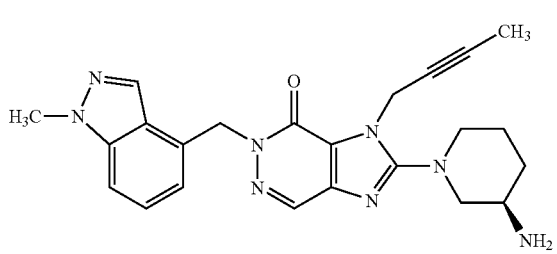

Prepared analogously to Example 1j by cleaving the Boc protective group with trifluoroacetic acid in dichloromethane.

Yield: 45% of theory.
$C_{23}H_{26}N_8O$ (430.52)
Mass spectrum: $(M+H)^+=431$
HPLC analysis:
The HPLC analysis was carried out under the following experimental conditions:
column: Xterra MS18; 3.5 µm; 4.6×50 mm
flow: 1 mL/min
eluant A: water/0.1% trifluoroacetic acid
eluant B: acetonitrile/0.1% trifluoroacetic acid
gradient: 5% B →98% B within 5 min.; maintain 98% B to 7.5 min.
A retention time of 3.13 min. was observed for this substance.

EXAMPLE 215

2-((R)-3-amino-piperidin-1-yl)-3-(but-2-ynyl)-5-(4-methyl-phthalazin-1-ylmethyl)-3,5-dihydro-imidazo[4,5-d]pyridazin-4-one

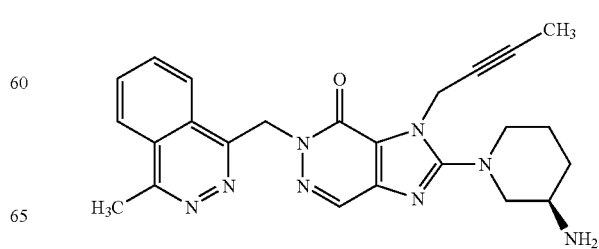

Prepared analogously to Example 1j by cleaving the Boc protective group with trifluoroacetic acid in dichloromethane.

Yield: 48% of theory.
$C_{24}H_{26}N_8O$ (442.53)
Mass spectrum: $(M+H)^+=433$
HPLC analysis (see Example 214):
retention time: 2.53 min.

EXAMPLE 216

2-((R)-3-amino-piperidin-1-yl)-3-(but-2-ynyl)-5-[2-(3-methyl-2-oxo-2,3-dihydro-benzoxazol-4-yl)-2-oxo-ethyl]-3,5-dihydro-imidazo[4,5-d]pyridazin-4-one

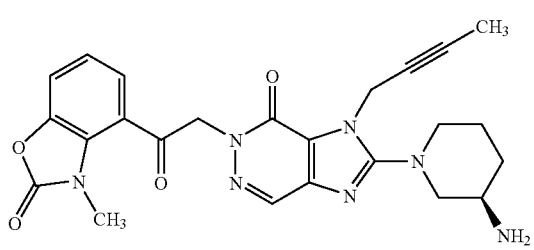

Prepared analogously to Example 1j by cleaving the Boc protective group with trifluoroacetic acid in dichloromethane.

Yield: 36% of theory.
$C_{24}H_{25}N_7O_4$ (475.51)
Mass spectrum: $(M+H)^+=476$
HPLC analysis (see Example 214):
retention time: 3.30 min.

EXAMPLE 217

2-((R)-3-amino-piperidin-1-yl)-3-(but-2-ynyl)-5-(2-methyl-2H-isoquinolin-1-on-4-ylmethyl)-3,5-dihydro-imidazo[4,5-d]pyridazin-4-one

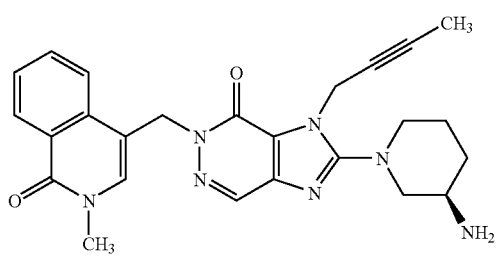

Prepared analogously to Example 1j by cleaving the Boc protective group with trifluoroacetic acid in dichloromethane.

Yield: 18% of theory.
$C_{25}H_{27}N_7O_2$ (457.54)
Mass spectrum: $(M+H)^+=458$
HPLC analysis (see Example 214):
retention time: 2.67 min.

EXAMPLE 218

2-((R)-3-amino-piperidin-1-yl)-3-(but-2-ynyl)-5-(8-methoxy-quinolin-5-ylmethyl)-3,5-dihydro-imidazo[4,5-d]pyridazin-4-one

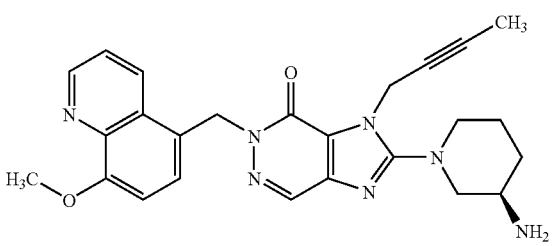

Prepared analogously to Example 1j by cleaving the Boc protective group with trifluoroacetic acid in dichloromethane.

Yield: 33% of theory.
$C_{25}H_{27}N_7O_2$ (457.54)
Mass spectrum: $(M+H)^+=458$
HPLC analysis (see Example 214):
retention time: 3.18 min.

EXAMPLE 219

2-((R)-3-amino-piperidin-1-yl)-3-(but-2-ynyl)-5-([1,5]naphthyridin-2-ylmethyl)-3,5-dihydro-imidazo[4,5-d]pyridazin-4-one

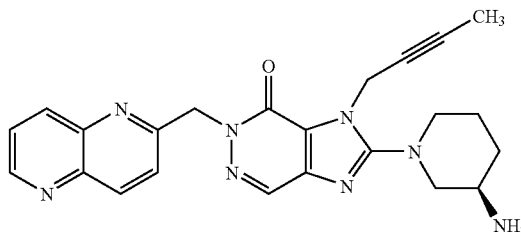

Prepared analogously to Example 1j by cleaving the Boc protective group with trifluoroacetic acid in dichloromethane.

Yield: 25% of theory.
$C_{23}H_{24}N_8O$ (428.50)
Mass spectrum: $(M+H)^+=429$
HPLC analysis (see Example 214):
retention time: 2.06 min.

EXAMPLE 220

2-((R)-3-amino-piperidin-1-yl)-3-(but-2-ynyl)-5-(2,3,8-trimethyl-quinoxalin-6-ylmethyl)-3,5-dihydro-imidazo[4,5-d]pyridazin-4-one

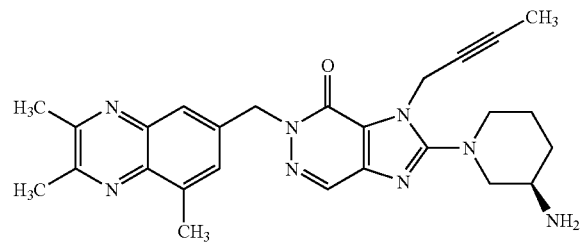

Prepared analogously to Example 1j by cleaving the Boc protective group with trifluoroacetic acid in dichloromethane.

Yield: 76% of theory.

$C_{26}H_{30}N_8O$ (470.58)

Mass spectrum: $(M+H)^+=471$

HPLC analysis (see Example 214):

retention time: 3.44 min.

EXAMPLE 221

2-((R)-3-amino-piperidin-1-yl)-3-(but-2-ynyl)-5-(4-morpholin-4-yl-quinazolin-2-ylmethyl)-3,5-dihydro-imidazo[4,5-d]pyridazin-4-one

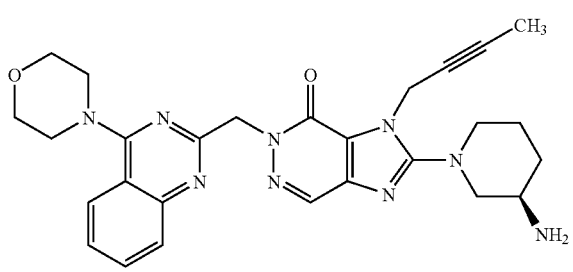

Prepared analogously to Example 1j by cleaving the Boc protective group with trifluoroacetic acid in dichloromethane.

Yield: 71% of theory.

$C_{27}H_{31}N_9O_2$ (513.61)

Mass spectrum: $(M+H)^+=514$

HPLC analysis (see Example 214):

retention time: 1.76 min.

EXAMPLE 222

2-((R)-3-amino-piperidin-1-yl)-3-(but-2-ynyl)-5-(3-pentafluorophenyl-allyl)-3,5-dihydro-imidazo[4,5-d]pyridazin-4-one

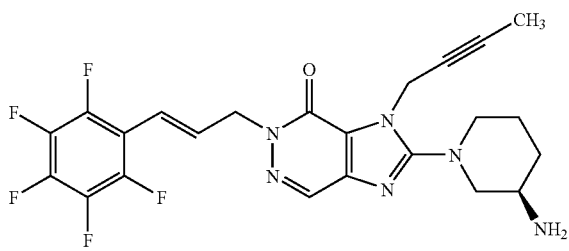

Prepared analogously to Example 1j by cleaving the Boc protective group with trifluoroacetic acid in dichloromethane.

Yield: 89% of theory.

$C_{23}H_{21}F_5N_6O$ (492.46)

Mass spectrum: $(M+H)^+=493$

Rf value: 0.18 (silica gel; dichloromethane/ethanol 9:1)

EXAMPLE 223

2-((R)-3-amino-piperidin-1-yl)-3-(but-2-ynyl)-7-methyl-5-(4-cyano-naphthalen-1-ylmethyl)-3,5-dihydro-imidazo[4,5-d]pyridazin-4-one

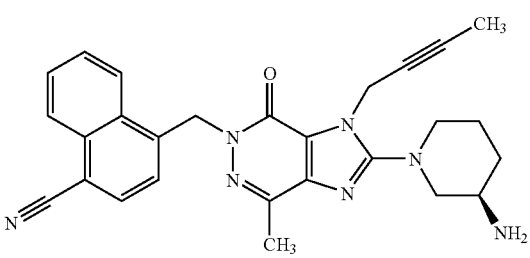

Prepared analogously to Example 1j by cleaving the Boc protective group with trifluoroacetic acid in dichloromethane.

Yield: 66% of theory.

$C_{27}H_{27}N_7O$ (465.56)

Mass spectrum: $(M+H)^+=466$

Rf value: 0.62

(silica gel RP-8; water/acetonitrile/trifluoroacetic acid 50:50:0.1)

EXAMPLE 224

| Coated tablets containing 75 mg of active substance | |
|---|---|
| 1 tablet core contains: | |
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 225

Tablets containing 100 mg of active substance

Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg
Diameter: 10 mm, biplanar, facetted on both sides and notched on one side.

EXAMPLE 226

Tablets containing 150 mg of active substance

Composition:
1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg
die: 10 mm, flat

EXAMPLE 227

Hard gelatine capsules containing 150 mg of active substance 1 capsule contains:

| | | |
|---|---|---|
| active substance | | 150.0 mg |
| corn starch (dried) | approx. | 80.0 mg |

Hard gelatine capsules containing 150 mg of active substance 1 capsule contains:

| | | |
|---|---|---|
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

EXAMPLE 228

Suppositories containing 150 mg of active substance 1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 229

Suspension containing 50 mg of active substance 100 ml of suspension contain:

| | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water ad | 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 230

| Ampoules containing 10 mg active substance | |
|---|---|
| Composition: | |
| active substance | 10.0 mg |
| 0.01 N hydrochloric acid q.s. | |
| double-distilled water ad | 2.0 ml |

Preparation:
The active substance is dissolved in the necessary amount of 0.01 N HCl, made isotonic with common salt, filtered sterile and transferred into 2 ml ampoules.

EXAMPLE 231

| Ampoules containing 50 mg of active substance | |
|---|---|
| Composition: | |
| active substance | 50.0 mg |
| 0.01 N hydrochloric acid q.s. | |
| double-distilled water ad | 10.0 ml |

Preparation:
The active substance is dissolved in the necessary amount of 0.01 N HCl, made isotonic with common salt, filtered sterile and transferred into 10 ml ampoules.

The invention claimed is:

1. A compound of formula

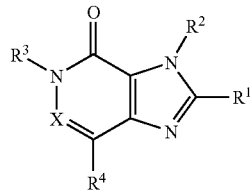

(I)

wherein
X denotes a nitrogen atom or a group of formula C—$R^5$, while $R^5$ denotes a hydrogen atom or a methyl group,
$R^1$ denotes a 5- to 7-membered cycloalkyleneimino group which is substituted by an amino group in the carbon skeleton and may be substituted by a $C_{1-3}$-alkyl group,
a 6- to 7-membered cycloalkyleneimino group wherein the methylene group is replaced by a —NH— group in the 4 position,
or an amino group substituted by a $C_{5-7}$-cycloalkyl group, while the $C_{5-7}$-cycloalkyl group is substituted by an amino group or a carbon atom in the 3 position of the $C_{5-7}$-cycloalkyl group is replaced by an —NH— group,
$R^2$ denotes a benzyl group wherein the phenyl group may be substituted by one or two fluorine, chlorine or bromine atoms or by a cyano group,
a straight-chain or branched $C_{3-8}$-alkenyl group,
a $C_{3-5}$-alkynyl group,
a $C_{3-7}$-cycloalkylmethyl group,
a $C_{5-7}$-cycloalkenylmethyl group,
or a furylmethyl, thienylmethyl, pyrrolylmethyl, thiazolylmethyl, imidazolylmethyl, pyridinylmethyl, pyrimidinylmethyl, pyridazinylmethyl or pyrazinylmethyl group,
$R^3$ denotes a straight-chain or branched $C_{1-6}$-alkyl group,
a phenyl-$C_{1-3}$-alkyl or naphthyl-$C_{1-3}$-alkyl group optionally substituted in the aryl moiety by a halogen atom, a cyano, a $C_{1-3}$-alkyl or a methoxy group,
a 2-phenyl-2-hydroxy-ethyl group,
a phenylcarbonylmethyl group,
wherein the phenyl group may be substituted by a hydroxy, $C_{1-3}$-alkyloxy, amino-carbonyl-$C_{1-3}$-alkoxy, ($C_{1-3}$-alkylamino)-carbonyl-$C_{1-3}$-alkoxy, [di-($C_{1-3}$-alkyl)-amino]-carbonyl-$C_{1-3}$-alkoxy, amino, $C_{1-3}$-alkyl-carbonylamino, $C_{3-6}$-cycloalkyl-carbonylamino, $C_{1-3}$-alkoxy-carbonylamino, $C_{1-3}$-alkylsulphonylamino or aminocarbonyl group,
a (3-methyl-2-oxo-2,3-dihydro-benzoxazolyl)-carbonylmethyl group,
a thienylcarbonylmethyl group,
a heteroaryl-$C_{1-3}$-alkyl group,
wherein said heteroaryl $C_{1-3}$-alkyl group is a monocyclic 5- or 6-membered heteroaryl group optionally substituted by one or two $C_{1-3}$-alkyl groups or by a morpholin-4-yl, pyridyl or phenyl group, while
said 6-membered heteroaryl group contains one, two or three nitrogen atoms and
said 5-membered heteroaryl group contains an imino group optionally substituted by a $C_{1-3}$-alkyl or phenyl-$C_{1-3}$-alkyl group, or an oxygen or sulphur atom or
an imino group optionally substituted by a $C_{1-3}$-alkyl or phenyl-$C_{1-3}$-alkyl group or an oxygen or sulphur atom and additionally contains a nitrogen atom or
an imino group optionally substituted by a $C_{1-3}$-alkyl or phenyl-$C_{1-3}$-alkyl group or an oxygen or sulphur atom and additionally contains two or three nitrogen atoms,
and additionally a phenyl ring, which may optionally be substituted by a halogen atom, by one or two $C_{1-3}$-alkyl groups or by a trifluoromethyl or methoxy group, may be fused to the above-mentioned monocyclic heteroaryl groups via two adjacent carbon atoms
and the bond may be formed via an atom of the heterocyclic moiety or of the fused-on phenyl ring,
a bicyclic heteroarylmethyl group according to one of the formulae

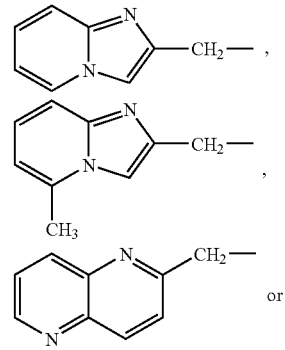

or

-continued

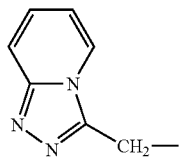

a group of formula

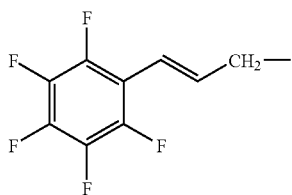

or a group of formulae

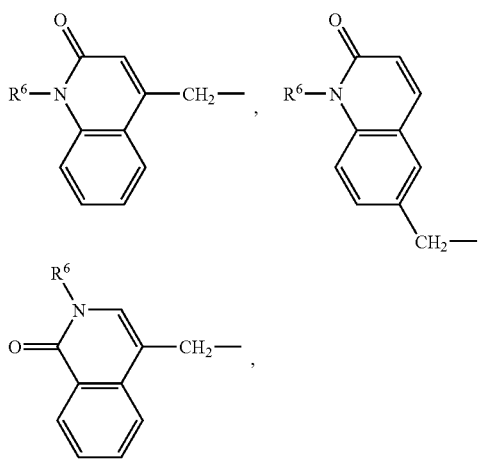

wherein R⁶ in each case denotes a hydrogen atom or a methyl group,
and R⁴ denotes a hydrogen atom or a $C_{1-3}$-alkyl group,
while unless otherwise stated the alkyl and alkoxy groups listed in the definitions which have more than two carbon atoms may be straight-chain or branched,
and the hydrogen atoms of the methyl or ethyl groups listed in the definitions may be wholly or partly replaced by fluorine atoms,
the tautomers, the enantiomers, the diastereomers, the mixtures thereof and the salts thereof.

2. Compounds of formula I according to claim 1, wherein
X denotes a nitrogen atom or a methyne group,
$R^1$ denotes a piperazin-1-yl, 3-amino-piperidin-1-yl, 3-amino-3-methyl-piperidin-1-yl, 3-amino-pyrrolidin-1-yl, 1,4-diazepan-1-yl, (2-amino-cyclohexyl)-amino or piperidin-3-yl-amino group,
$R^2$ denotes a benzyl group wherein the phenyl group may be substituted by one or two fluorine atoms, by a chlorine or bromine atom or by a cyano group,
a straight-chain or branched $C_{3-8}$-alkenyl group,
a propyn-3-yl or but-2-yn-4-yl group,
a cyclopropylmethyl group,
a $C_{5-7}$-cycloalkenylmethyl group,
or a furylmethyl or thienylmethyl group,
$R^3$ denotes a straight-chain or branched $C_{1-6}$-alkyl group,
a phenyl-$C_{1-2}$-alkyl or naphthyl-$C_{1-2}$-alkyl group optionally substituted in the aryl moiety by a fluorine, chlorine or bromine atom or by a cyano, $C_{1-3}$-alkyl or methoxy group,
a 2-phenyl-2-hydroxy-ethyl group,
a phenylcarbonylmethyl group,
wherein the phenyl group may be substituted by a hydroxy, $C_{1-3}$-alkyloxy, amino-carbonyl-$C_{1-3}$-alkoxy, ($C_{1-3}$-alkylamino)-carbonyl-$C_{1-3}$-alkoxy, [di-($C_{1-3}$-alkyl)-amino]-carbonyl-$C_{1-3}$-alkoxy, amino, $C_{1-3}$-alkyl-carbonylamino, $C_{3-6}$-cycloalkyl-carbonylamino, $C_{1-3}$-alkoxy-carbonylamino, $C_{1-3}$-alkylsulphonylamino or aminocarbonyl group,
a (3-methyl-2-oxo-2,3-dihydro-benzoxazolyl)-carbonylmethyl group,
a thienylcarbonylmethyl group,
a heteroaryl-methyl group,
while by the phrase a "heteroaryl group" is meant a pyridinyl, pyrimidinyl, pyridazinyl, pyrazinyl, thiazolyl, oxazolyl, isothiazolyl, isoxazolyl, pyrazolyl, imidazolyl, oxadiazolyl, thiadiazolyl or thienyl group optionally substituted by one or two methyl groups or by a pyridyl or phenyl group,
and while additionally a phenyl ring, which may optionally be substituted by a chlorine atom, by one or two methyl groups or by a trifluoromethyl or methoxy group, may be fused to the above-mentioned monocyclic heteroaryl groups via two adjacent carbon atoms
and the bond may be formed via an atom of the heterocyclic moiety or of the fused-on phenyl ring,
an imidazo[1,2-a]pyridin-2-yl-methyl group of formulae

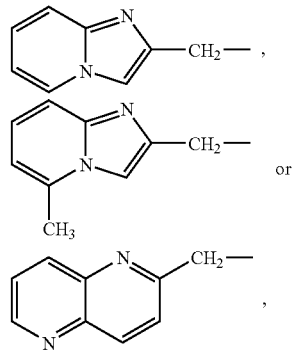

a 1,2,4-triazolo[4,3-a]pyridin-3-yl group of formula

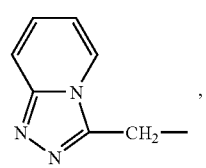

or a group of formulae

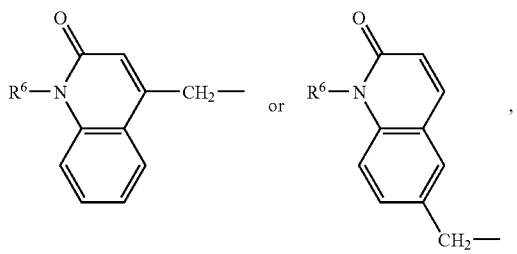

wherein R[6] in each case denotes a hydrogen atom or a methyl group,
and R[4] denotes a hydrogen atom or a methyl group,
while unless otherwise stated the alkyl and alkoxy groups listed in the definitions which have more than two carbon atoms may be straight-chain or branched,
and the hydrogen atoms of the methyl or ethyl groups listed in the definitions may be wholly or partly replaced by fluorine atoms,
the tautomers, the enantiomers, the diastereomers, the mixtures thereof and the salts thereof.

3. Compounds of formula I according to claim 1, wherein X, R[2], R[3] and R[4] are defined as in claim 2 and R[1] denotes a 3-amino-piperidin-1-yl group,
the tautomers, the enantiomers, the diastereomers, the mixtures thereof and the salts thereof.

4. Compounds of formula I according to claim 2 and R[2] denotes a 3-methylallyl, a 3,3-dimethylallyl or a but-2-yn-4-yl group,
the tautomers, the enantiomers, the diastereomers, the mixtures thereof and the salts thereof.

5. A compound selected from the group consisting of:

(1)  2-(3-amino-piperidin-1-yl)-3-(but-2-ynyl)-5-(naphthalen-1-ylmethyl)-3,5-dihydro-imidazo[4,5-d]pyridazin-4-one

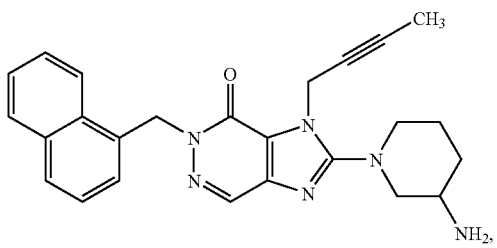

(2) 2-(3-amino-piperidin-1-yl)-3-but-2-ynyl-5-(3-methyl-isoquinolin-1-ylmethyl)-3,5-dihydro-imidazo[4,5-d]pyridazin-4-one,

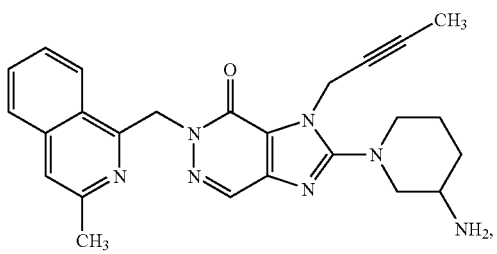

(3)  2-(3-amino-piperidin-1-yl)-3-(but-2-ynyl)-5-(quinazolin-2-ylmethyl)-3,5-dihydro-imidazo[4, 5-d]pyridazin-4-one

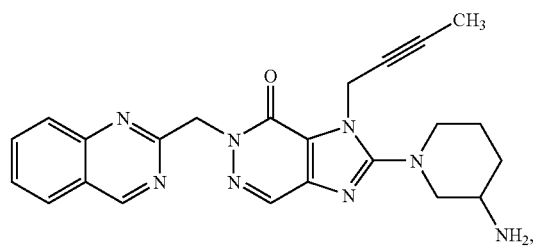

(4)  2-((R)-3-amino-piperidin-1-yl)-3-(but-2-ynyl)-5-(4-methyl-quinazolin-2-yl-methyl)-3,5-dihydro-imidazo[4,5-d]pyridazin-4-one

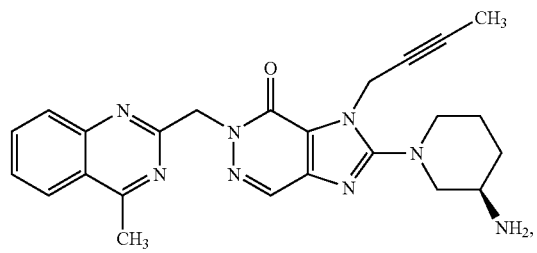

(5)  2-((R)-3-amino-piperidin-1-yl)-3-(but-2-ynyl)-5-(4-cyano-naphthalen-1-yl-methyl)-3,5-dihydro-imidazo[4,5-d]pyridazin-4-one

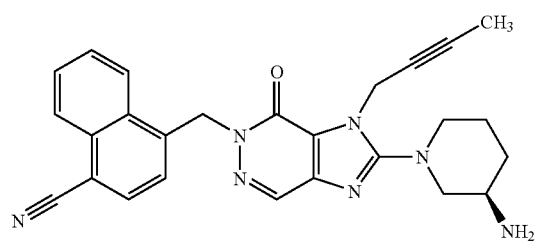

(6)  2-((R)-3-amino-piperidin-1-yl)-3-(but-2-ynyl)-5-(4-bromonaphth-1-ylmethyl)-3,5-dihydro-imidazo[4,5-d]pyridazin-4-one

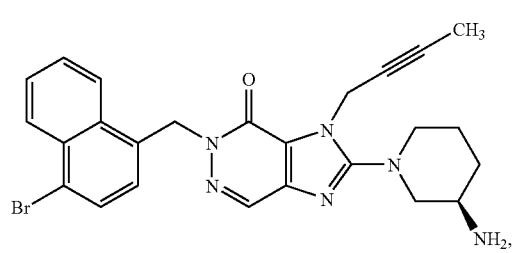

(7) 2-((R)-3-amino-piperidin-1-yl)-3-(but-2-ynyl)-5-(benzo[1,2,5]thiadiazol-5-yl-methyl)-3,5-dihydro-imidazo[4,5-d]pyridazin-4-one

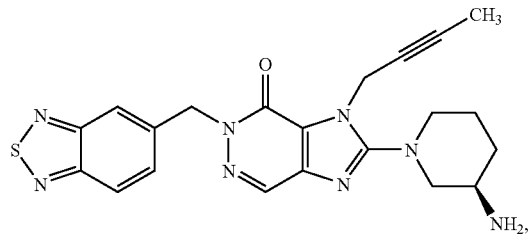

(8) 2-((R)-3-amino-piperidin-1-yl)-3-(2-chlorobenzyl)-5-(3-methyl-isoquinolin-1-ylmethyl)-3,5-dihydro-imidazo[4,5-d]pyridazin-4-one

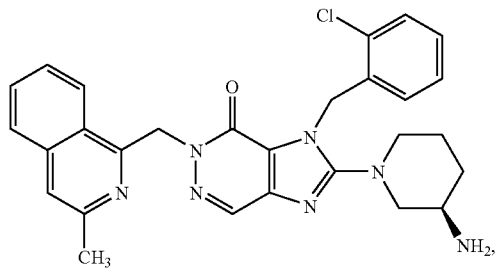

(9) 2-(3-amino-piperidin-1-yl)-3-(but-2-ynyl)-5-(quinoxalin-6-ylmethyl)-3,5-dihydro-imidazo[4,5-d]pyridazin-4-one

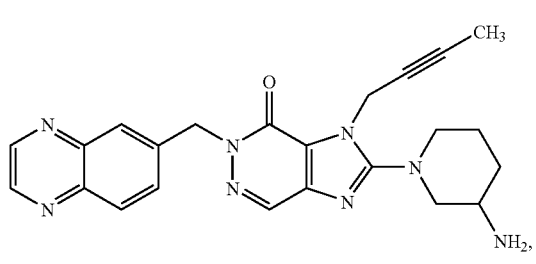

(10) 2-((R)-3-amino-piperidin-1-yl)-3-(but-2-ynyl)-5-(2,3-dimethyl-quinoxalin-6-yl-methyl)-3,5-dihydro-imidazo[4,5-d]pyridazin-4-one

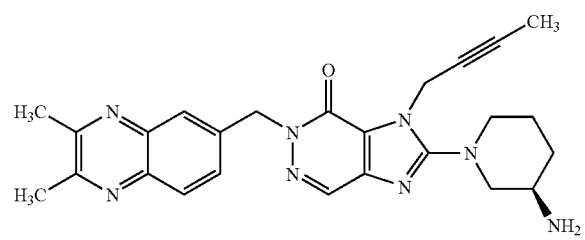

(11) 2-((R)-3-amino-piperidin-1-yl)-3-(but-2-ynyl)-5-(5-methyl-imidazo[1,2-a]pyridin-2-ylmethyl)-3,5-dihydro-imidazo[4,5-d]pyridazin-4-one

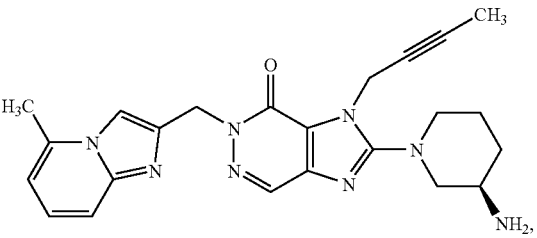

(12) 2-((R)-3-amino-piperidin-1-yl)-3-(but-2-ynyl)-5-(1-methyl-1H-quinolin-2-on-6-ylmethyl)-3,5-dihydro-imidazo[4,5-d]pyridazin-4-one

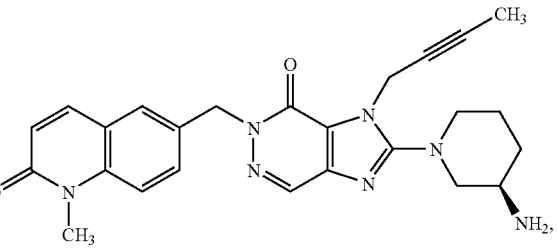

(13) 2-((R)-3-amino-piperidin-1-yl)-3-(but-2-ynyl)-5-(4-methyl-phthalazin-1-yl-methyl)-3,5-dihydro-imidazo[4,5-d]pyridazin-4-one

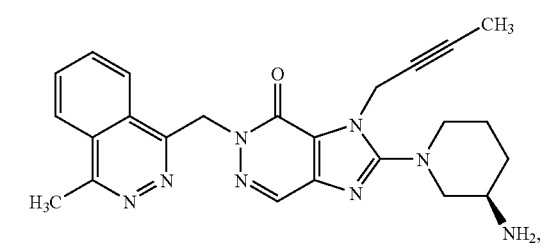

(14) 2-((R)-3-amino-piperidin-1-yl)-3-(but-2-ynyl)-5-([1,5]naphthyridin-2-ylmethyl)-3,5-dihydro-imidazo[4,5-d]pyridazin-4-one

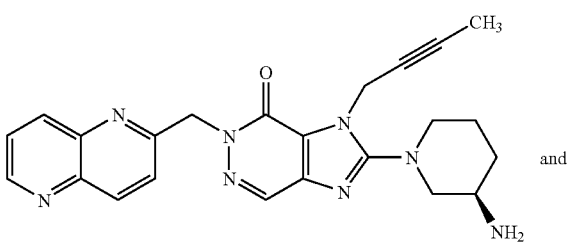

and

(15) 2-((R)-3-amino-piperidin-1-yl)-3-(but-2-ynyl)-5-(2,3,8-trimethyl-quinoxalin-6-yl-methyl)-3,5-dihydro-imidazo[4,5-d]pyridazin-4-one

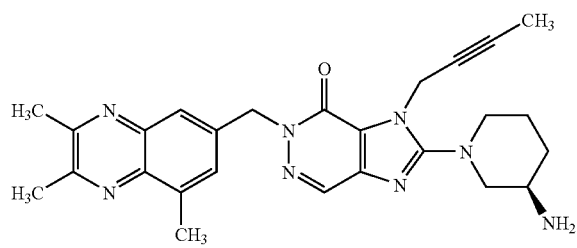

and the enantiomers and the salts thereof.

6. Physiologically acceptable salts of the compounds according to claim 1 with inorganic or organic acids.

7. Pharmaceutical compositions containing a compound according to claim 6 together with one or more inert carriers and/or diluents.

8. Pharmaceutical compositions containing a compound according to claim 1 together with one or more inert carriers and/or diluents.

9. A method of treating a disease selected from the list consisting of type I and type II diabetes mellitus and obesity, in a mammal in need thereof, by administration of a pharmaceutically acceptable amount of a compound according to claim 1.

* * * * *